(12) United States Patent
Lim et al.

(10) Patent No.: US 10,131,650 B2
(45) Date of Patent: Nov. 20, 2018

(54) ALPHA-HELIX ANALOG HAVING TRIAZINE-PIPERAZINE BACKBONE AND METHOD FOR PREPARING SAME

(71) Applicants: POSCO, Pohang-si, Gyeongsangbuk-do (KR); POSTECH ACADEMY-INDUSTRY FOUNDATION, Pohang-si, Gyeongsangbuk-do (KR)

(72) Inventors: Hyun-Suk Lim, Pohang-si (KR); Misook Oh, Pohang-si (KR); Quyen Q. Hoang, Carmel, IN (US); Wei Wang, Indianapolis, IN (US)

(73) Assignees: POSCO, Pohang-si, Gyeongsangbuk-do (KR); POSTECH ACADEMY-INDUSTRY FOUNDATION, Pohang-si, Gyeongsangbuk-do (KR)

( * ) Notice: Subject to any disclaimer, the term of this patent is extended or adjusted under 35 U.S.C. 154(b) by 0 days.

(21) Appl. No.: 15/326,422

(22) PCT Filed: Dec. 23, 2014

(86) PCT No.: PCT/KR2014/012746
§ 371 (c)(1),
(2) Date: Jan. 13, 2017

(87) PCT Pub. No.: WO2016/010210
PCT Pub. Date: Jan. 21, 2016

(65) Prior Publication Data
US 2017/0204086 A1 Jul. 20, 2017

(30) Foreign Application Priority Data
Jul. 14, 2014 (KR) .................. 10-2014-0088669

(51) Int. Cl.
| C07D 403/04 | (2006.01) |
|---|---|
| C07D 403/14 | (2006.01) |
| A61K 31/53 | (2006.01) |
| A61K 31/496 | (2006.01) |
| A61K 31/497 | (2006.01) |
| C07D 405/14 | (2006.01) |

(52) U.S. Cl.
CPC ........... *C07D 403/14* (2013.01); *A61K 31/497* (2013.01); *A61K 31/53* (2013.01); *C07D 403/04* (2013.01); *C07D 405/14* (2013.01)

(58) Field of Classification Search
CPC .... C07D 403/04; C07D 403/14; A61K 31/53; A61K 31/497
USPC ................ 544/194, 196, 204, 219; 514/245; 644/194, 196, 204, 219, 359
See application file for complete search history.

(56) References Cited

U.S. PATENT DOCUMENTS

2003/0008882 A1    1/2003   Hamilton et al.

FOREIGN PATENT DOCUMENTS

| CN | 86100904 A | 5/1987 |
|---|---|---|
| CN | 1629157 A | 6/2005 |
| CN | 102341394 A | 2/2012 |
| EP | 0415371 A2 | 3/1991 |
| JP | S58-217554 A | 12/1983 |
| WO | 2010-011864 A2 | 1/2010 |
| WO | 2010-042758 A2 | 4/2010 |
| WO | 2010-083501 A2 | 7/2010 |

OTHER PUBLICATIONS

PubChem Compound—pccompound 1-200, create date 2005-2013, Search date Aug. 20, 2017.*
STN-5, search date Aug. 17, 2017.*
International Search Report dated Apr. 13, 2015 issued in International Patent Application No. PCT/KR2014/012746 (with English translation).
M. Oh, et al., "Pharmacological chaperones targeting cancer-associated MCL-1 and Parkinson's disease-associated a-synuclein," PNAS, pp. 1-7.

* cited by examiner

*Primary Examiner* — Venkataraman Balasubramanian
(74) *Attorney, Agent, or Firm* — McDermott Will & Emery LLP

(57) ABSTRACT

The alpha-helix mimetic containing a triazine-piperazine scaffold is provided. The alpha-helix mimetic compound can mimic efficiently the alpha-helix structure of protein secondary structure and act as an inhibitor for the protein interaction being specific to various diseases mediated by alpha-helix. Therefore, the compound can be used as a biological probe and have a high potential of drug treating diseases.

12 Claims, 17 Drawing Sheets

[Fig. 1]
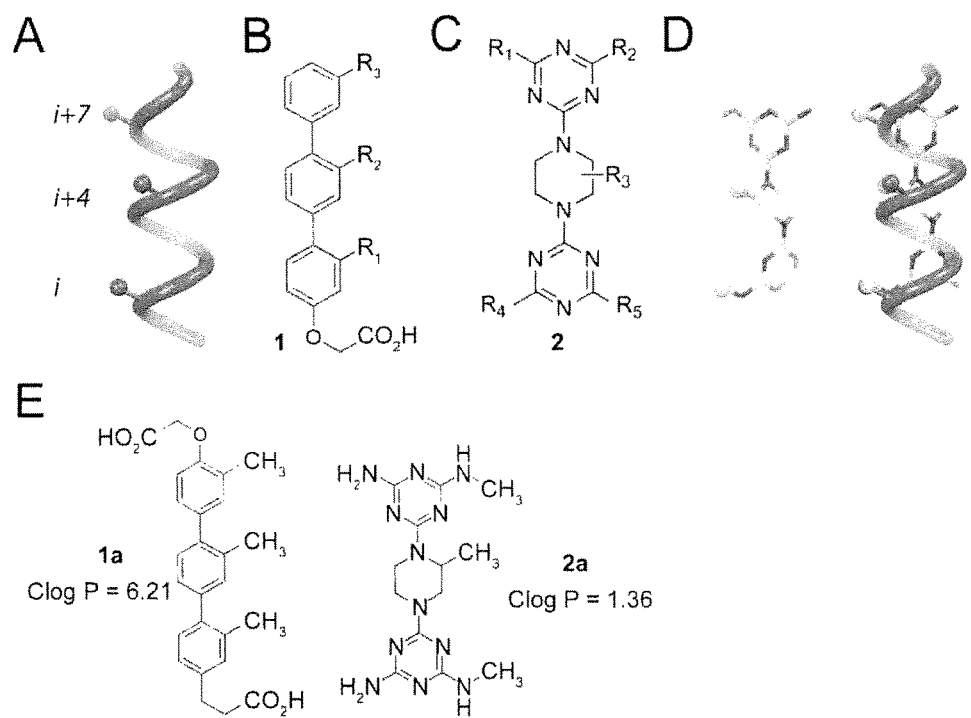

[Fig. 2]
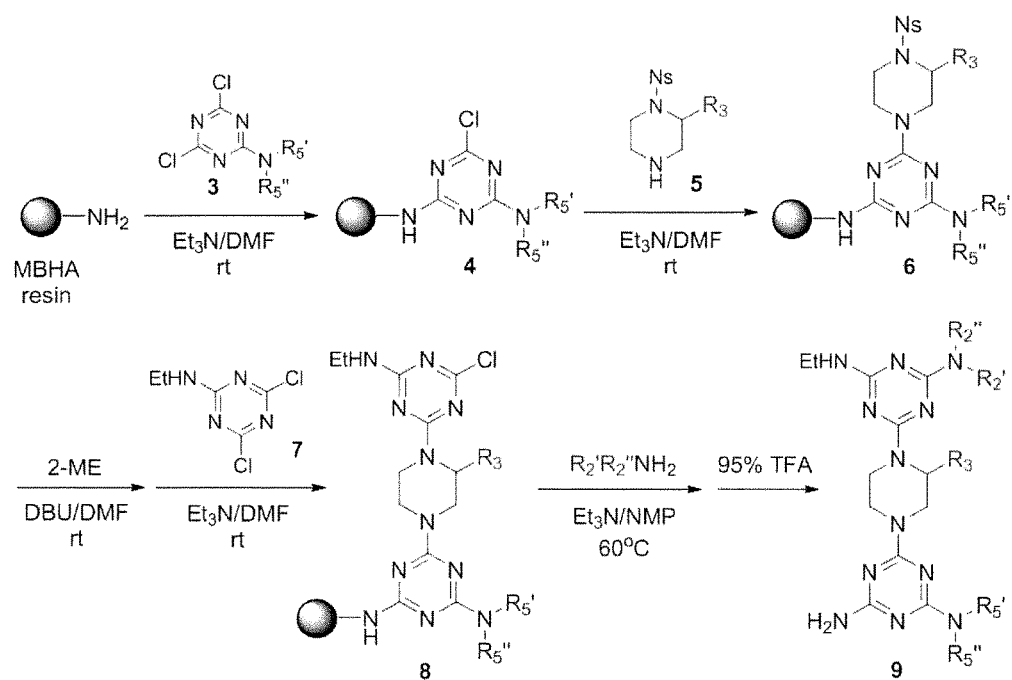

[Fig. 3]
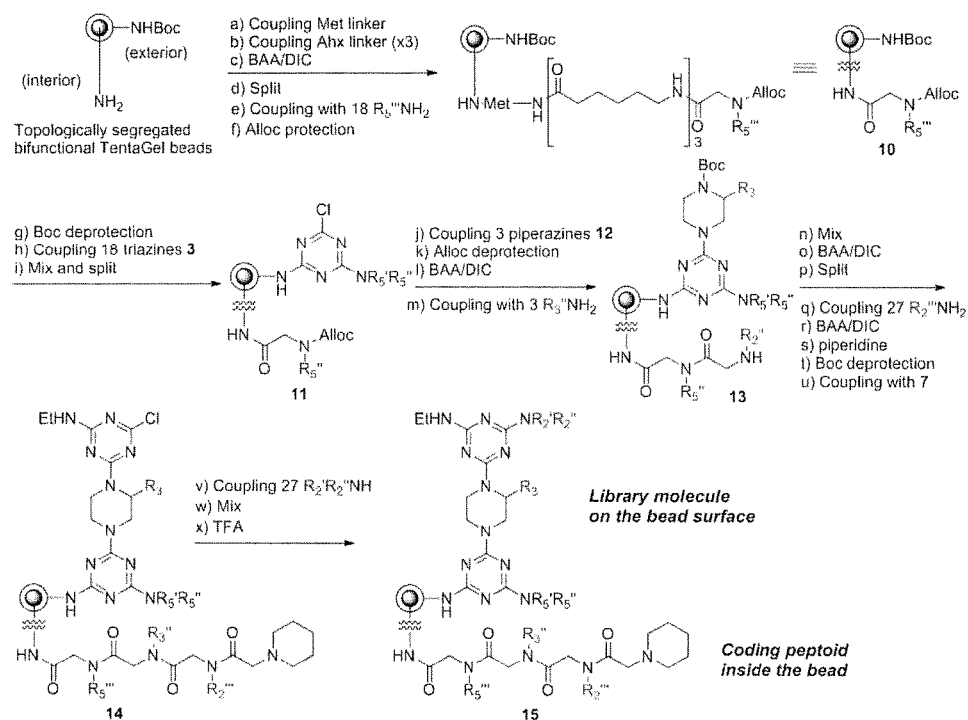
Theoretical diversity: 18 x 3 x 27 = 1,458

[Fig. 4]
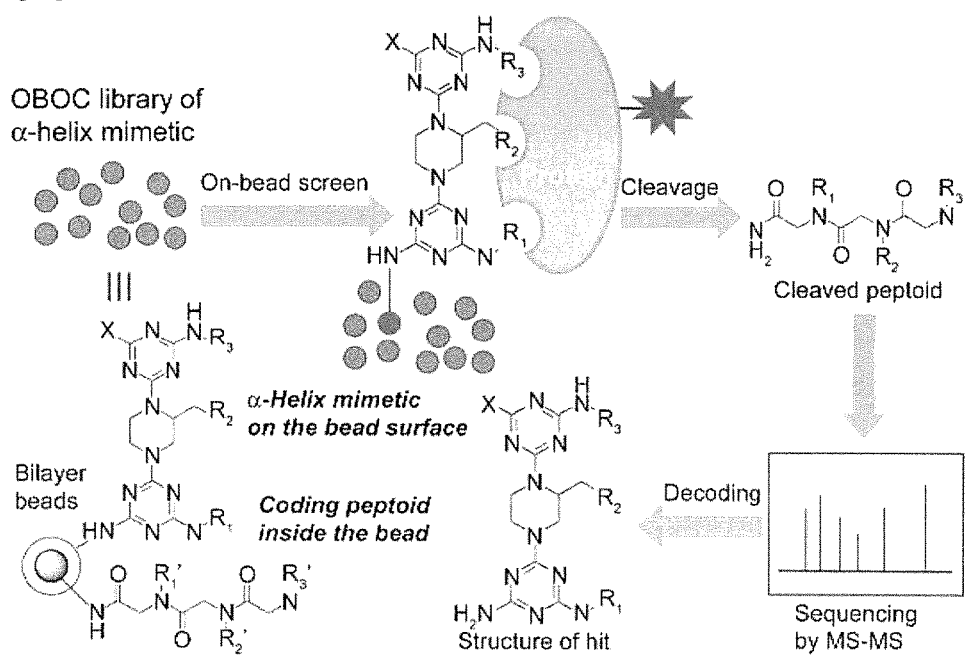

[Fig. 5]
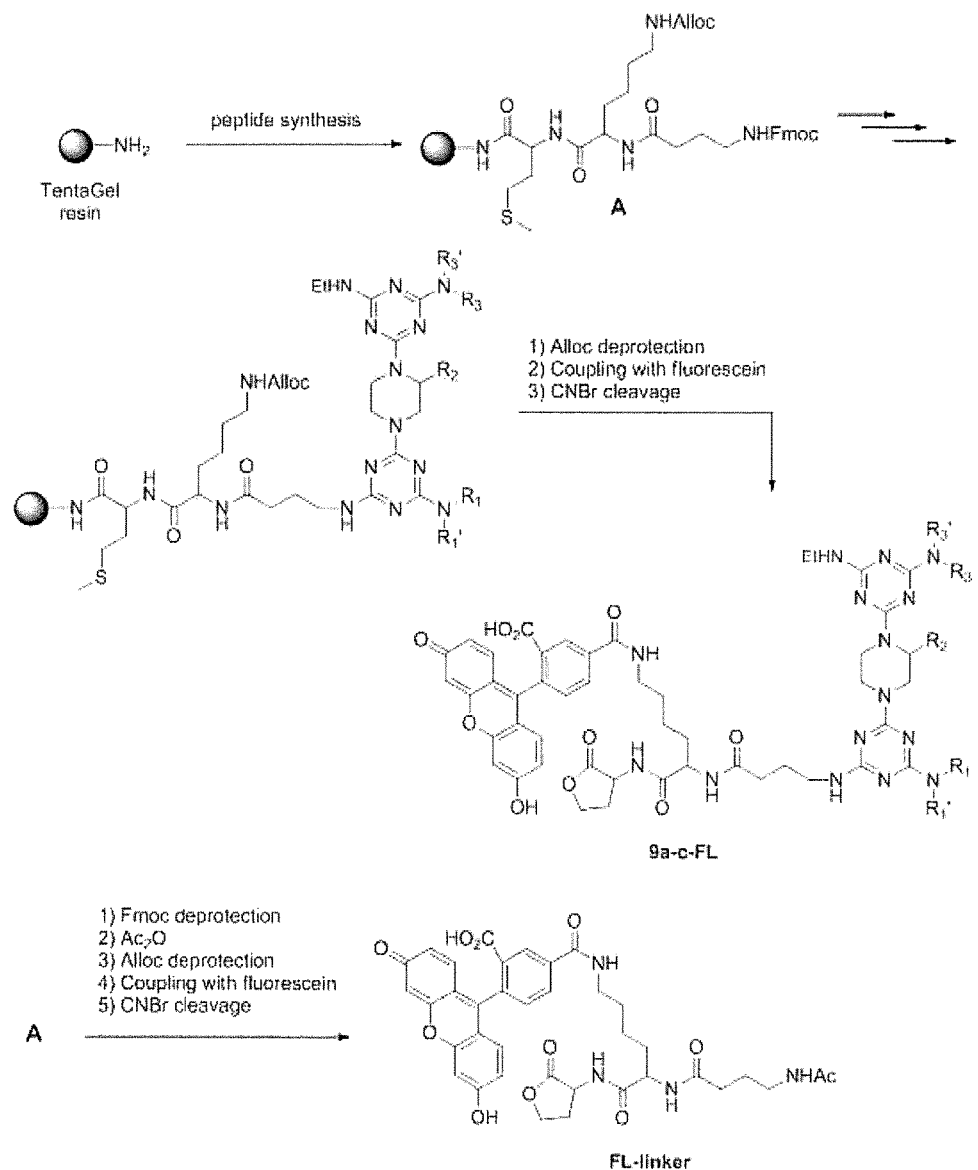

[Fig. 6]
A
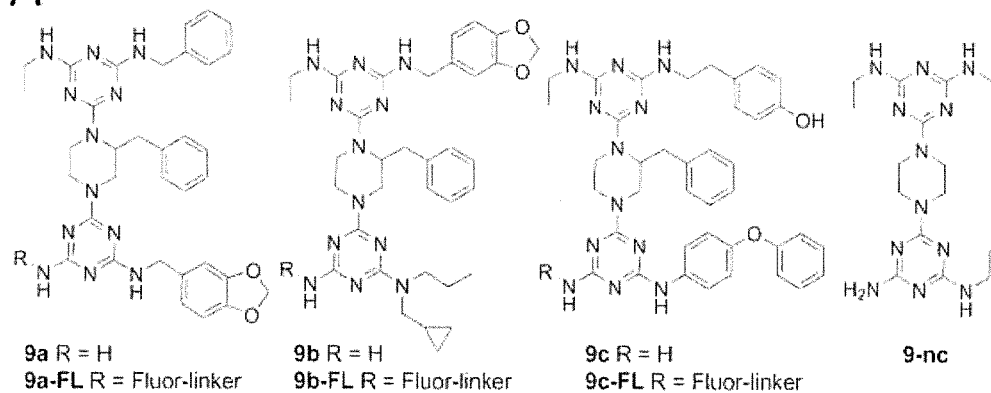
9a R = H
9a-FL R = Fluor-linker
9b R = H
9b-FL R = Fluor-linker
9c R = H
9c-FL R = Fluor-linker
9-nc
B
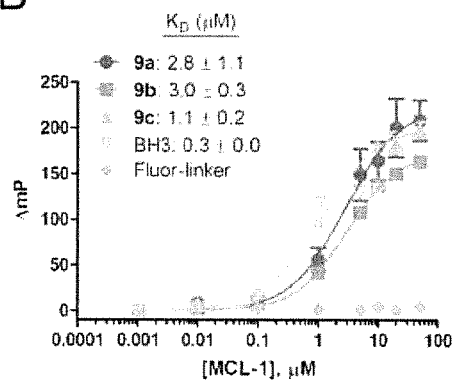
$K_D$ (μM)
- 9a: 2.8 ± 1.1
- 9b: 3.0 ± 0.3
- 9c: 1.1 ± 0.2
- BH3: 0.3 ± 0.0
- Fluor-linker
C
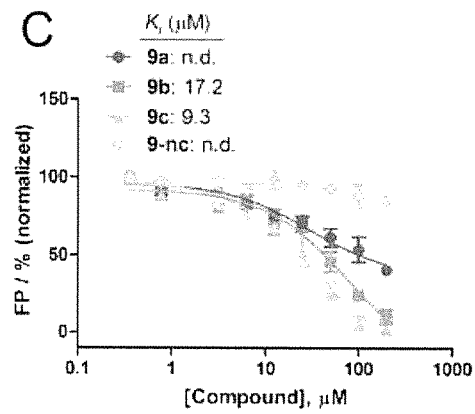
$K_i$ (μM)
- 9a: n.d.
- 9b: 17.2
- 9c: 9.3
- 9-nc: n.d.

[Fig. 7]
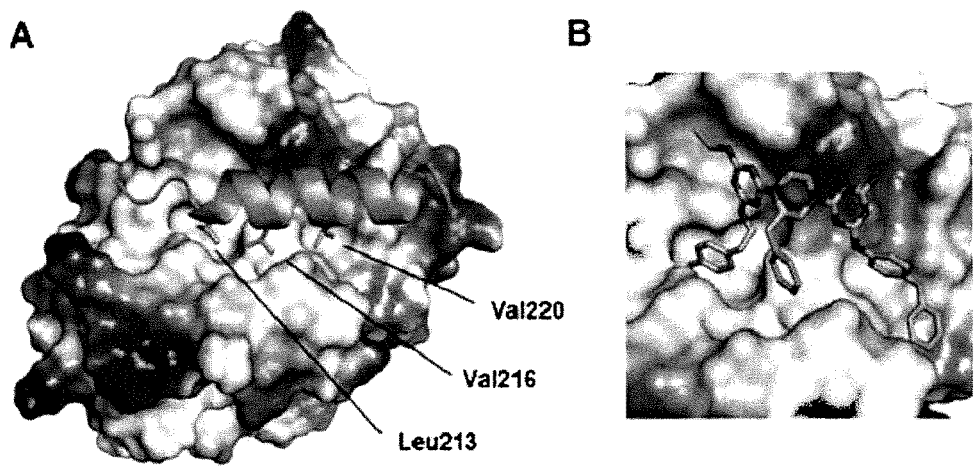

[Fig. 8]
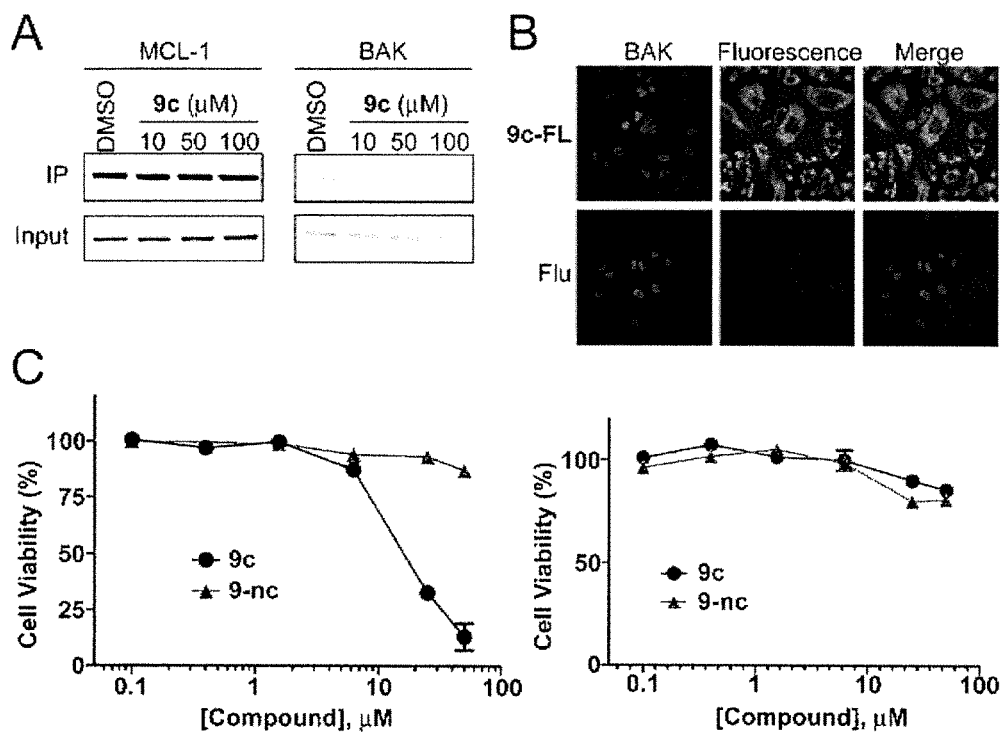

[Fig. 9]
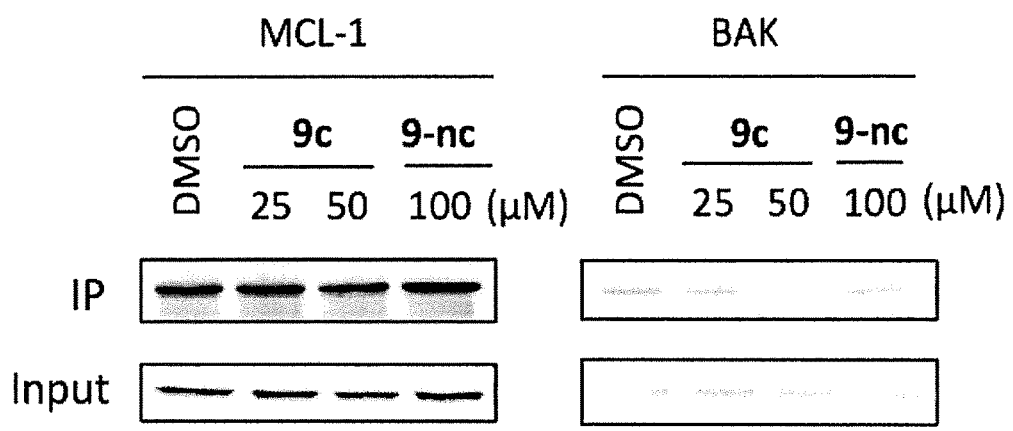

[Fig. 10]
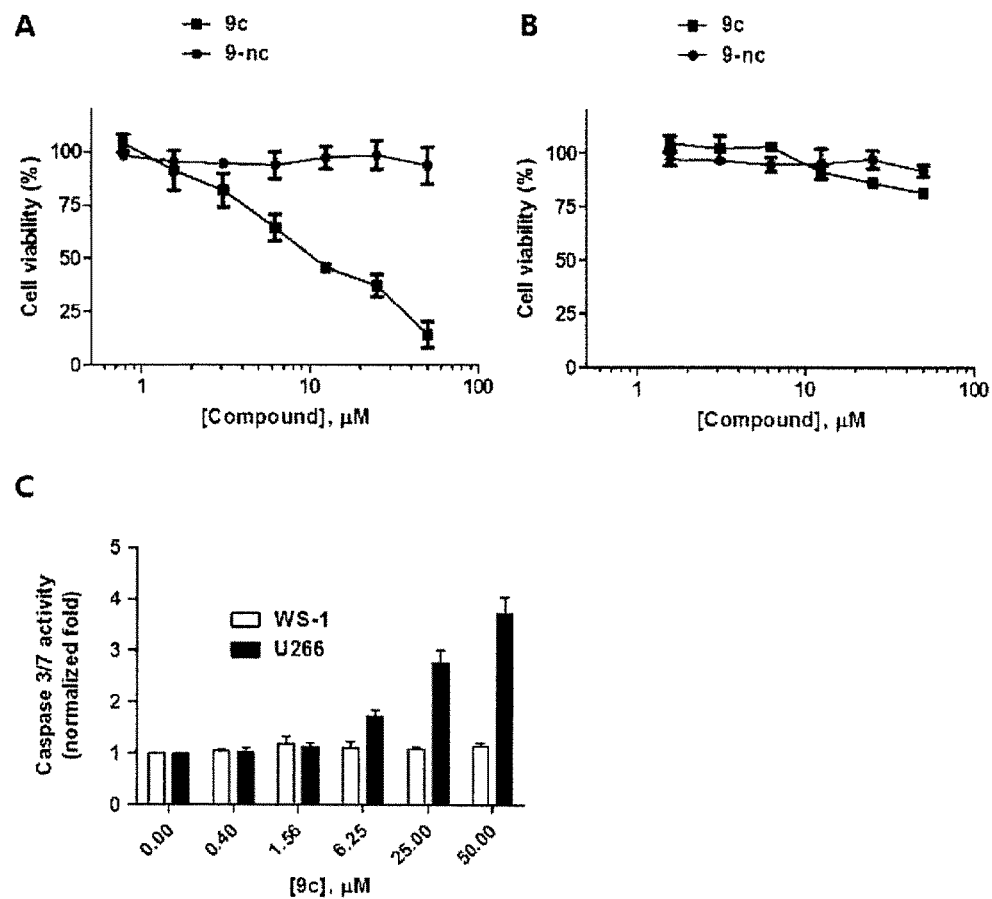

[Fig. 11]
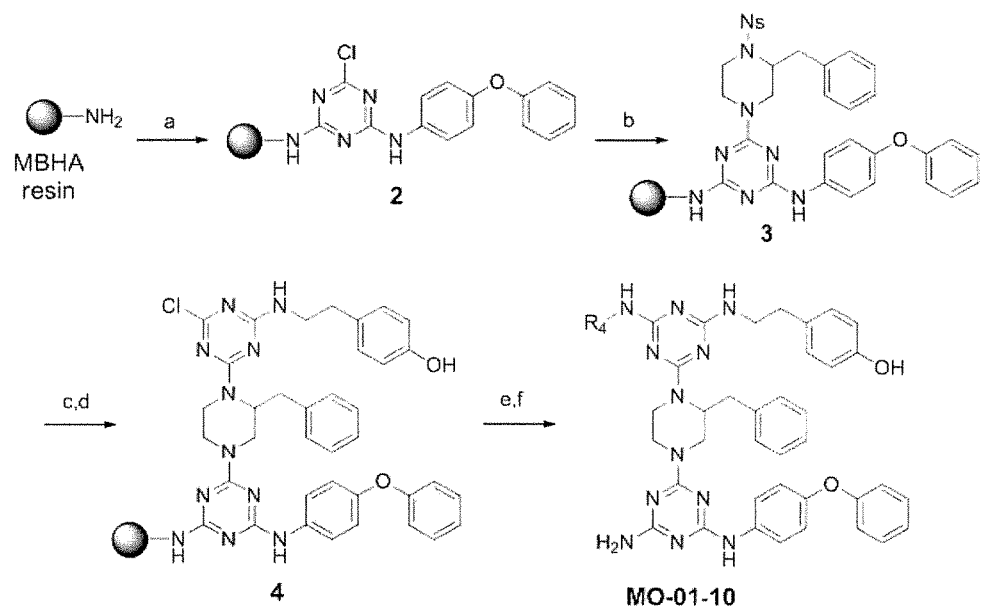

[Fig. 12]
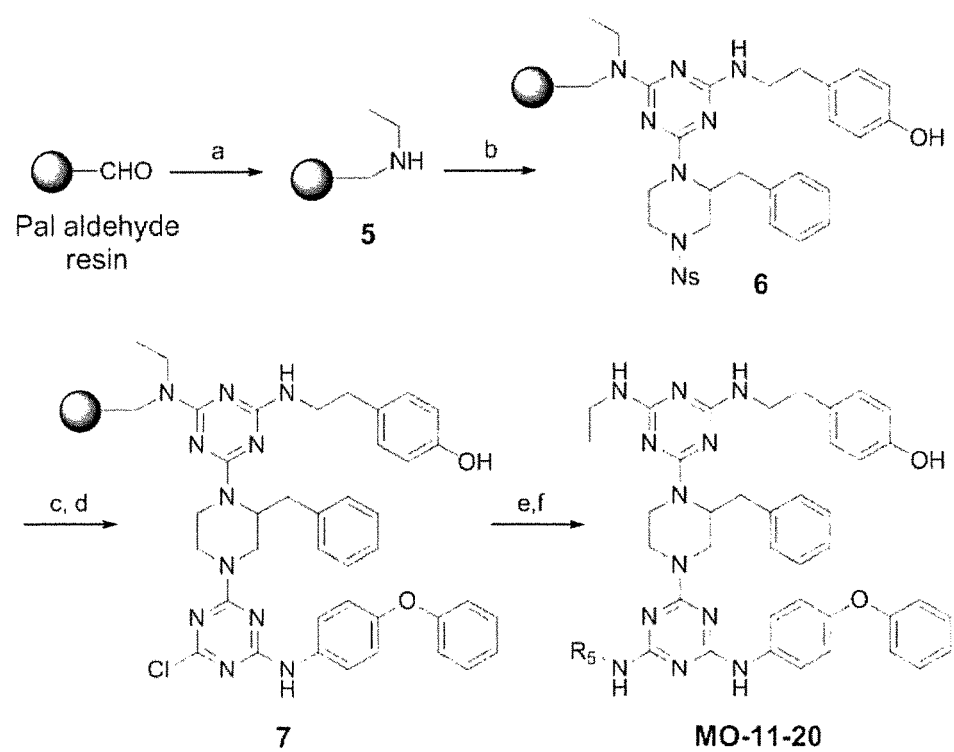

[Fig. 13]
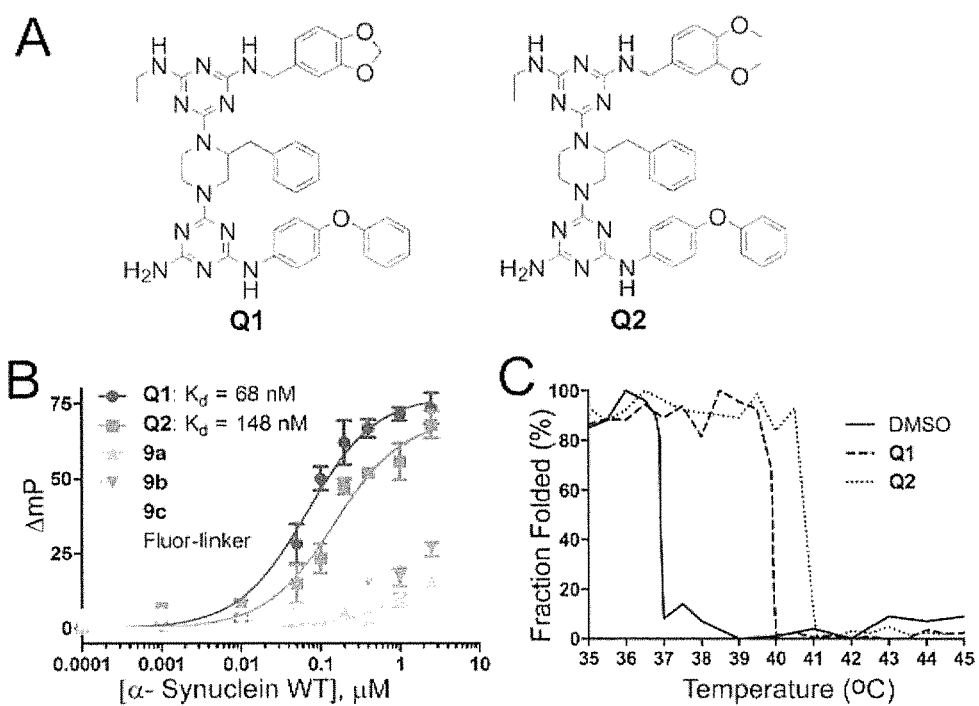

[Fig. 14]
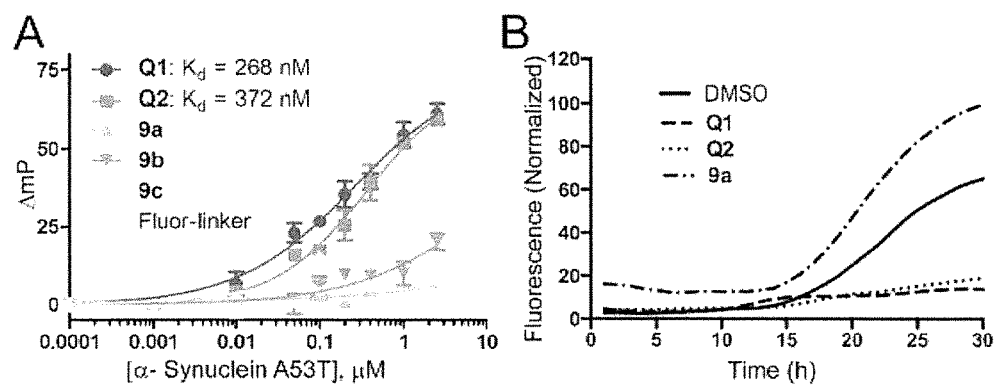

[Fig. 15]
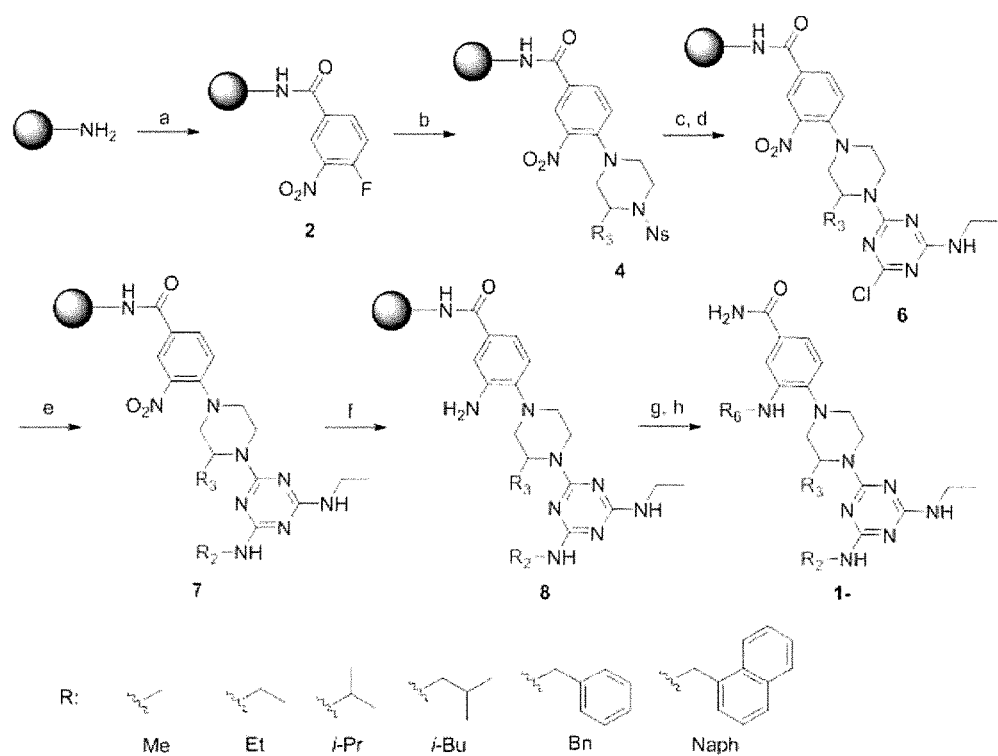

[Fig. 16]
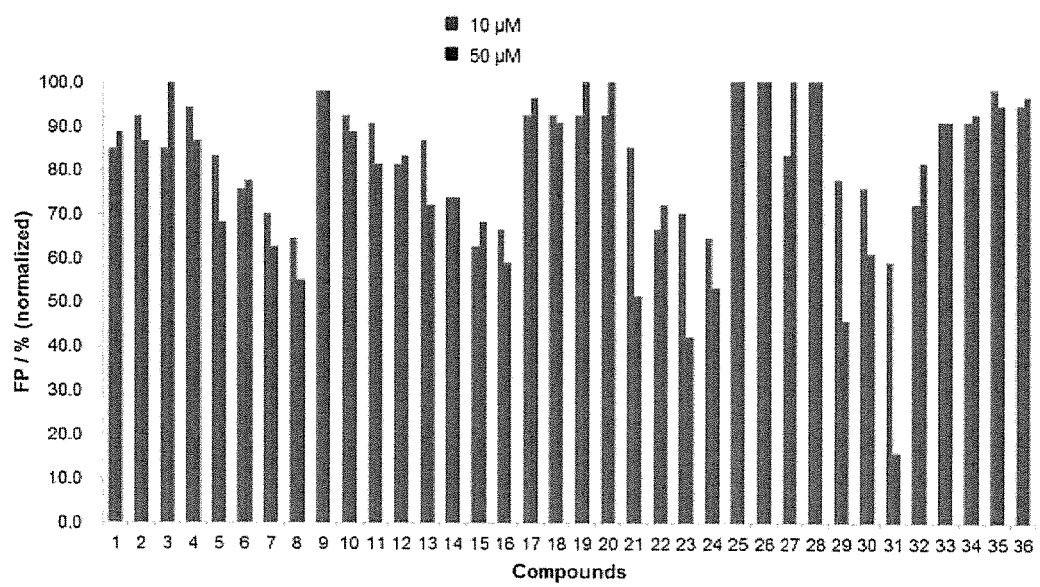

[Fig. 17]
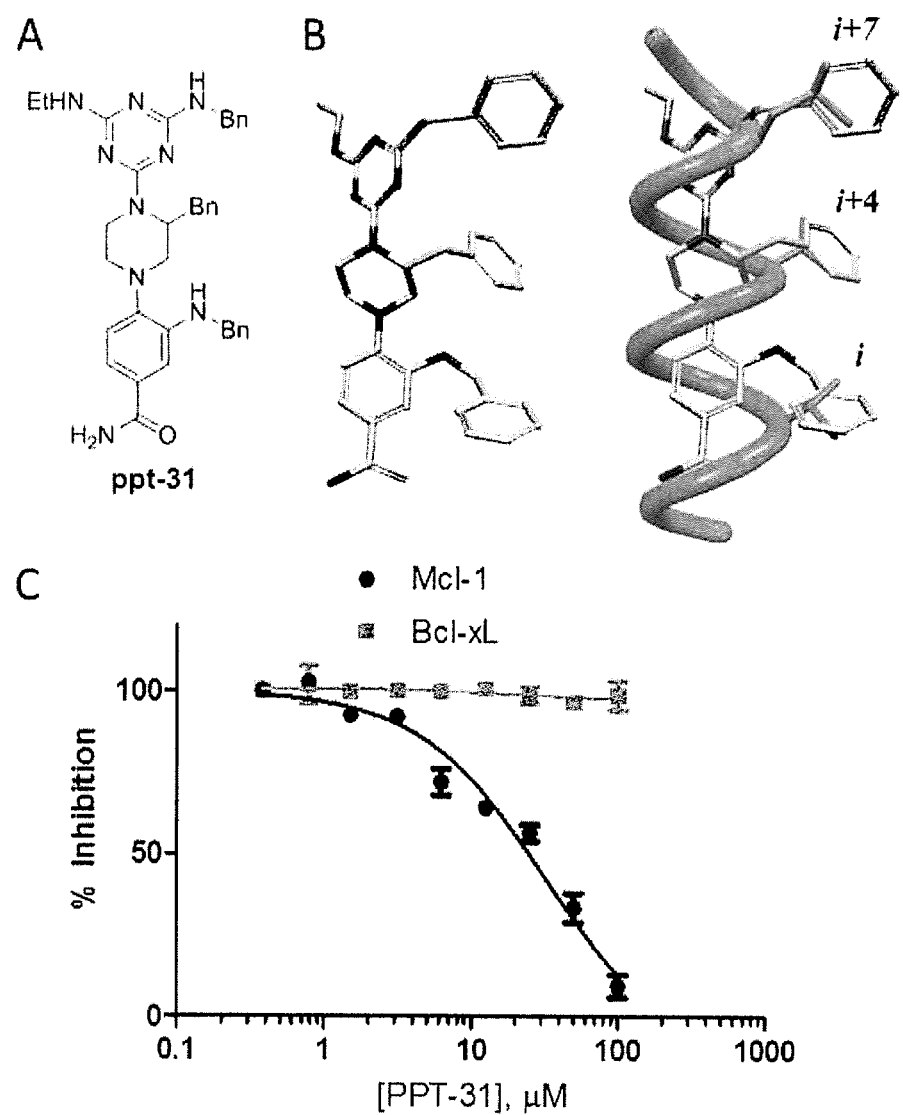

ALPHA-HELIX ANALOG HAVING TRIAZINE-PIPERAZINE BACKBONE AND METHOD FOR PREPARING SAME

RELATED APPLICATIONS

This application is the U.S. National Phase under 35 U.S.C. § 371 of International Application No. PCT/KR2014/012746, filed on Dec. 23, 2014 which in turn claims the benefit of Korean Patent Application No. 10-2014-0088669 filed on Jul. 14, 2014, the disclosures of which applications are incorporated by reference herein.

TECHNICAL FIELD

The present invention relates to a compound having a triazine-piperazine scaffold as an alpha-helix mimetic. The compound mimics the alpha-helix structure of protein secondary structure, and acts as an inhibitor for a protein interaction mediated by alpha-helix which is specific to various diseases. Therefore, the compound can be used as a biological probe and have a high potential of a therapeutic agent for diseases.

RELATED ART

Cells maintain vital functions by performing a variety of biological functions such as gene regulation, cell growth, cell cycle, metabolism, and signal transduction through diverse and complex protein-protein interactions (PPI). In addition, many diseases are known to be associated with abnormal protein-protein interactions or protein misfolding. The understanding of protein-protein interaction and its function in a cell is a cornerstone of understanding life phenomena and an important basis for the development of new drugs and the treatment of diseases.

In many protein interaction, the protein is known to bind to the target protein by recognizing a short alpha-helix (α-helix) with 2 to 3 turns. The alpha-helix structure has a rotation (turn) of about 3.14 amino acid residues and a side chain spatially arranged for every 3 to 4 residues. The spaces arranged by the side chain are called as i, i+3/i+4, i+7 and etc., the amino acid residue located in i, i+3/i+4, and i+7 acts as a recognition motif in binding to the target protein. Thus, low-molecular substances that can mimic the structure of alpha-helix peptides are expected to play a role as inhibitors of protein interactions, and studies on the development of alpha-helix mimetic have been actively conducted.

With respect to the matter, an alpha-helix-like compound having a terphenyl scaffold has been reported (J. Am. Chem. Soc. 2001, 123, 5382-3; Nat. Chem. 2013, 5(3):161-173; Curr. Opin. Chem. Biol. 2010, 14(3):341-346). As described above, the alpha-helix in nature has three amino acid residues (amino acid residues at positions i, i+3/i+4, i+7) being used as a recognition motif in the protein binding. The alpha-helix mimetic compound having a terphenyl scaffold is designed for mimicking the function of alpha-helix, by positioning the substituents respectively connected to the three benzene rings constituting the terphenyl scaffold are located at three-dimensional spatial positions corresponding to the three amino acid residues.

However, the alpha-helix mimetic based on terphenyl structure has many difficulties in being developed as a therapeutic agent, because it is not only difficult to synthesize, but also to have a low solubility in an aqueous solution due to the high hydrophobicity.

DISCLOSURE

Technical Problem

Therefore, it is necessary to develop a low-molecular alpha-helix mimetic having a structure that has a good solubility in an aqueous solution, cell permeability and is easy to synthesize.

Technical Solution

The present inventors have developed a novel alpha-helix mimetic compound having triazine-piperazine as a core structure in order to overcome the problems of alpha-helix mimetic having a terphenyl scaffold. It was also confirmed that the alpha-helix mimetic compound of the present invention successfully mimicked the three-dimensional orientation of three amino acid residues (i, i+3 or i+4, i+7) been essential for alpha-helix. Further, the present inventors have developed a solid phase synthesis method for simply synthesizing an alpha-helix mimetic having a triazine-piperazine scaffold.

Accordingly, an object of the present invention is to provide alpha-helix mimetic compounds and salts thereof having triazine-piperazine as a core structure.

It is another object of the present invention to provide a method for preparing the alpha-helix mimetic compounds.

It is further object of the present invention to provide a composition for inhibiting a protein interaction, including the alpha-helix mimetic compound or salt thereof.

It is further object of the present invention to provide a method for inhibiting a protein interaction, including treating the alpha-helix mimetic compound or a salt thereof.

It is another object of the present invention to provide a composition for detecting a protein interaction, including the alpha-helix mimetic compound or salt thereof.

It is another object of the present invention to provide a pharmaceutical composition for treating a disease associated with alpha-helix-mediated protein interaction, including the alpha-helix mimetic compound or salts thereof.

It is another object of the present invention to provide a method for treating a disease associated with alpha-helix-mediated protein interaction, including administering an effective amount of the alpha-helix mimetic compound or salt thereof to an individual.

Advantageous Effect

The present invention provides an alpha-helix mimetic compound having a triazine-piperazine scaffold. The compound can be used as an inhibitor of alpha-helix mediated protein interaction being specific to various diseases by efficiently mimicking the alpha-helix structure of protein secondary structure.

BRIEF DESCRIPTION OF DRAWINGS

In FIG. 1, A represents the positions of side chain i, i+4, and i+7 in alpha-helix, B represents the structure of the conventional alpha-helix mimetic having terphenyl scaffold, C represents the structure of the alpha-helix mimetic of the present invention having triazine-piperazine-triazine scaffold, D shows the overlayed with the alpha-helix, when the alpha-helix mimetic of the present invention is prepared as an energy-minimized structure (2a) (that is, $R_2$, $R_3$, $R_5$=$CH_3$; $R_1$, $R_4$=H), and FIG. 1E is the comparison result of C log P values, when the alpha-helix mimetic of the present invention and the conventional alpha-helix mimetic having terphenyl scaffold are prepared as an energy-minimized structure (1a, 1b).

FIG. 2 represents the outline of solid phase synthesis method for preparing the alpha-helix mimetic compound having a triazine-piperazine-triazine as core structure.

FIG. 3 represents a procedure of constructing the alpha-helix mimetic chemical library using peptoid as a coding tag.

FIG. 4 represents a procedure of selecting the alpha-helix mimetic compound binding to the target protein from the alpha-helix mimetic chemical library.

FIG. 5 represents a procedure of labeling the compounds 9a, 9b and 9c with a fluorescent material.

In FIG. 6, A represents the structures of the compound 9a (Chemical formula 4), 9b (Chemical formula 5) and 9c (Chemical formula 6), and negative control 9-nc that are selected by binding to MCL-1, B represents a result of fluorescence polarization assay showing that compound 9a, 9b and 9c bind to MCL-1, and C represents the result of comparative fluorescence polarization assay showing that compound 9a, 9b and 9c and the fluorescence-labeled BH-3 peptide bind to MCL-1.

In FIG. 7, A shows the crystal structure of MCL-1 and BH3 peptide complex, indicating that the major binding site of MCL-1 is the side chain of three hydrophobic residues (Leu213, Val216 and Val220) of BH3. B is a result of computer docking assay showing that compound 9c binds to the BH3 binding site of MCL-1.

In FIG. 8, A represents a result of MCL-1 immunoprecipitation and Western blotting showing that MCL-1/BAK interaction is inhibited in Jurkat T cells after treatment of various concentrations of compound 9c (10, 50, 100 μM) or DMSO for 2.5 hours. B shows a result of confocal microscopy after treatment of A549 cells with 1 μM of 9c-FL or 5 (6)-carboxyfuorescein (Flu) for 4 hours. C shows cell viability (%) of Jurkat T cells (left panel) and WS-1 normal fibroblast (right panel) that are treated with various concentrations of compounds 9c and 9-nc (negative control).

FIG. 9 shows a result of MCL-1 immunoprecipitation and Western blotting showing that MCL-1/BAK interaction is inhibited after treatment of Jurkat T cells with compound 9c (25, 50 μM), compound 9-nc (100 μM) or DMSO for 2.5 hours.

In FIG. 10, A represents a cell viability (%) of U266 cells (left panel) that are treated with various concentrations of compounds 9c and 9-nc (negative control) for 24 hours. B represents a cell viability (%) of normal cell that are treated with various concentrations of compounds 9c and 9-nc (negative control) for 24 hours. C shows a result of Caspase activity analysis after treatment of U266 cells and WS-1 cells with compound 9c at the indicated concentrations of DMSO for 16 hours.

FIG. 11 represents a procedure of substituting Et corresponding to $R_1$ position of compound 9c with various hydrophilic groups FIG. 12 represents a procedure of substituting hydrogen corresponding to $R_4$ position of compound 9c with various hydrophilic groups In FIG. 13, A represents the structure of compound Q1 (Chemical formula 7) and compound Q2 (Chemical formula 8), B represents a result of fluorescence polarization assay showing that each compound Q1, Q2, 9a, 9b, 9c and Fluor-linker as negative controls binds to wild type α-synuclein. C shows a result of CD (circular dichroism) thermal denaturation monitoring the unfolding of α-synuclein with or without compound Q1 and Q2.

In FIG. 14, A represents a result of fluorescence polarization assay showing that each compound Q1, Q2, 9a, 9b, 9c and Fluor-linker binds to mutant α-synuclein A53T. B represents a result of Thioflavin-T aggregation assay showing that each compound Q1, Q2 and negative control 9c affects the aggregation of mutant α-synuclein A53T.

FIG. 15 represents an outline of solid phase synthesis method to prepare an alpha-helix mimetic compound having phenyl-piperazine-triazine as core structure. (a) shows reaction of 4-fluoro-3-nitrobenzoic acid, HATU, DIEA, and DMF at a room temperature for 24 hours; (b) show reaction of N-nosyl protected piperazine derivative ("3"), DIEA and DMF at 95° C. for 12 hours; (c) shows reaction of 2-mercaptoethanol, DBU, and DMF at room temperature for 3 hours; (d) shows reaction of 2-ethylamino-4,6-dichloro-[1,3,5]triazine ("5"), DIEA and THF at 60° C., 3 hours; (e) shows reaction of $R_3NH_2$, DIEA and NMP at 80° C. overnight; (f) shows reaction of $SnCl_2.2H_2O$, and DMF at room temperature for 24 hours, (g) shows reaction of $R_1CHO$, $CH(OMe)_3$/DMF/MeOH 9:1:2 (1% HOAc) at 50° C. for 18 hours and then reaction of $NaCNBH_3$ and THF at 50° C. 6 hours, in case of condition A (aromatic aldehyde); and reaction of $R_1CHO$, benzotriazole, $CH(OMe)_3$/DMF/MeOH 9:1:2 (1% HOAc) at room temperature for 18 hours and then reaction of $NaCNBH_3$ and THF at room temperature for 6 hours, in case of condition B (aliphatic aldehyde); and (h) shows reaction of 95% TFA in $CH_2Cl_2$ at room temperature for 3 hours.

FIG. 16 shows a result of competitive fluorescence polarization assay showing that 36 species of alpha-helix mimetic compounds having phenyl-piperazine-triazine as core structure inhibit an interaction between Mcl-1 and BH3 peptide. Blue rod shows the inhibitory effect at 10 μM and red rod shows the inhibitory effect at 50 μM.

In FIG. 17, A shows the structure of compound of Chemical formula 10 designated as PPT-31, B shows a result of molecular modeling with overlaying with BH3 helix peptide and an energy-minimized structure. C shows an inhibition curve of PPT-31 that the fluorescence labeled BH3 peptide inhibits the binding of Mcl-1 (black) and Bcl-XL (gray). The error bar means standard deviation of independent test results at three times.

MODE FOR INVENTION

The present invention relates to alpha-helix mimetic compounds and salts thereof, which have triazine-piperazine as core structure, and uses thereof.

In accordance with the present invention, the alpha-helix mimetic compound having triazine-piperazine as core structure can be represented by the following Chemical formula 1:

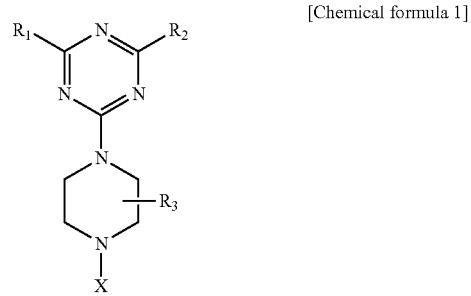

[Chemical formula 1]

In Chemical formula 1,
X is

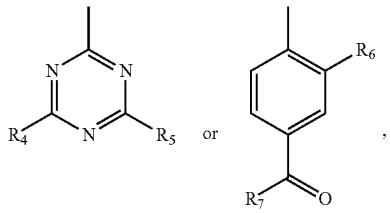

or , $R_1$, $R_2$, $R_4$ and $R_5$ are independently —$NR_8R_9$ or —$OR_{10}$, $R_8$ and $R_9$ are independently hydrogen, ($C_1$-$C_6$) alkyl, ($C_2$-$C_6$) alkenyl, ($C_2$-$C_6$) alkynyl, —$(CH_2)_m$—($C_3$-$C_{10}$) cycloalkyl, —$(CH_2)_m$—($C_4$-$C_{10}$) cycloalkenyl, —$(CH_2)_m$—($C_3$-$C_{10}$) heterocycle, —$(CH_2)_m$—($C_3$-$C_{10}$) aryl, or —$(CH_2)_m$—($C_3$-$C_{10}$) heteroaryl that may be substituted with at least one to 5 substituents independently selected from the group consisting of $C_{1-8}$ alkyl, $C_{2-6}$ alkenyl, $C_{1-4}$alkoxyl, $C_{3-6}$ cycloalkyl, halogen, $C_{1-4}$ haloalkyl, $C_3$-$C_{10}$ heteroaryl, $C_3$-$C_{10}$ heterocyclic, —N—($C_3$-$C_{10}$) aryl, —N—($C_3$-$C_{10}$) heteroaryl, carboxy, guanidyl, hydroxy, nitro, amino, phenyl, phenoxy, oxo and sulfonamide, where m is an integer of 0 to 3, $R_8$ and $R_9$ may be connected to each other to form a ring together with C, N or O, $R_{10}$ is hydrogen, ($C_1$-$C_6$) alkyl, ($C_2$-$C_6$) alkenyl, ($C_2$-$C_6$) alkynyl, —$(CH_2)_n$—($C_3$-$C_{10}$) cycloalkyl, —$(CH_2)_n$—($C_3$-$C_{10}$) heterocycle, —$(CH_2)_n$—($C_3$-$C_{10}$) aryl, or —$(CH_2)_n$—($C_3$-$C_{10}$) heteroaryl that may be substituted with at least one to 5 substituents independently selected from the group consisting of $C_{1-8}$ alkyl, $C_{1-4}$ alkoxyl, $C_{3-6}$ cycloalkyl, halogen, $C_{1-4}$ haloalkyl, carboxy, hydroxy, amino, oxo, phenyl and phenoxy, where n is an integer of 0 to 3, $R_3$ is ($C_1$-$C_6$) alkyl or —$(CH_2)_p$—($C_3$-$C_{10}$) aryl, where p is an integer of 0 to 3, $R_6$ is —$NR_{11}$, wherein $R_{11}$ is hydrogen, ($C_1$-$C_6$) alkyl, ($C_2$-$C_6$) alkenyl, ($C_2$-$C_6$) alkynyl, —$(CH_2)_q$—($C_3$-$C_{10}$) cycloalkyl, —$(CH_2)_m$—($C_4$-$C_{10}$) cycloalkenyl, —$(CH_2)_q$—($C_3$-$C_{10}$) heterocycle, —$(CH_2)_q$—($C_3$-$C_{10}$) aryl, or —$(CH_2)_q$—($C_3$-$C_{10}$) heteroaryl that may be substituted with at least one to 5 substituents independently selected from the group consisting of $C_{1-8}$ alkyl, $C_{2-6}$ alkenyl, $C_{1-4}$ alkoxyl, $C_{3-6}$ cycloalkyl, halogen, $C_{1-4}$ haloalkyl, $C_3$-$C_{10}$ heteroaryl, $C_3$-$C_{10}$ heterocyclic, carboxy, guanidyl, hydroxy, nitro, amino, phenyl, phenoxy, oxo and sulfonamide, where q is an integer of 0 to 3, $R_{11}$ may be connected to each other to form a ring together with C or O, and $R_7$ is —$NH_2$.

The compounds of present invention include stereoisomers, for examples diastereomer and enanthiomer having all basic molecular structure. Particularly, a chiral center can have (R)- or (S)-configuration, substituent on divalent cyclic (partly) saturated radical can have cis- or trans-configuration. A compound including carbon-carbon double bond can have E or Z-notation at the double bond. The stereoisomers of compound shown in Chemical formula 1 is intended to be included in the scope of present invention.

Specifically, the compounds of present invention include a compound having triazine-piperazine-triazine as core structure and a compound having phenyl-piperazine-triazine as core structure.

Hereinafter, the compound provided by the present invention will be described in more detail.

In one embodiment, the present invention relates to alpha-helix mimetic compounds and salts thereof having a core structure of triazine-piperazine-triazine.

A compound having the core structure of triazine-piperazine-triazine can be represented by the following chemical formula 2:

[Chemical formula 2]

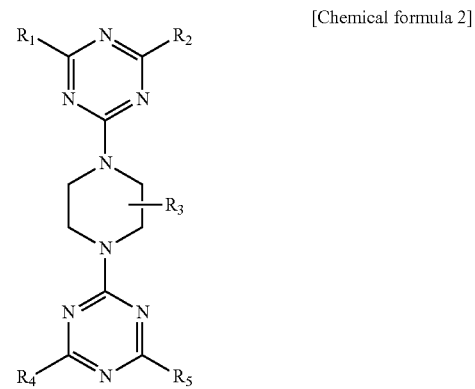

In the Chemical Formula 2, $R_1$, $R_2$, $R_4$ and $R_5$ are independently —$NR_8R_9$ or —$OR_{10}$, $R_8$ and $R_9$ are independently hydrogen, ($C_1$-$C_6$) alkyl, ($C_2$-$C_6$) alkenyl, ($C_2$-$C_6$) alkynyl, —$(CH_2)_m$—($C_3$-$C_{10}$) cycloalkyl, —$(CH_2)_m$—($C_4$-$C_{10}$) cycloalkenyl, —$(CH_2)_m$—($C_3$-$C_{10}$) heterocycle, —$(CH_2)_m$—($C_3$-$C_{10}$) aryl, or —$(CH_2)_m$—($C_3$-$C_{10}$) heteroaryl that may be substituted with at least one to 5 substituents independently selected from the group consisting of $C_{1-8}$ alkyl, $C_{2-6}$ alkenyl, $C_{1-4}$ alkoxyl, $C_{3-6}$ cycloalkyl, halogen, $C_{1-4}$ haloalkyl, $C_3$-$C_{10}$ heteroaryl, $C_3$-$C_{10}$ heterocyclic, —N—($C_3$-$C_{10}$) aryl, —N—($C_3$-$C_{10}$) heteroaryl, carboxy, guanidyl, hydroxy, nitro, amino, phenyl, phenoxy, oxo and sulfonamide, wherein m is an integer of 0 to 3, $R_8$ and $R_9$ may be connected to each other to form a ring together with C, N or O, $R_{10}$ is hydrogen, ($C_1$-$C_6$) alkyl, ($C_2$-$C_6$) alkenyl, ($C_2$-$C_6$) alkynyl, —$(CH_2)_n$—($C_3$-$C_{10}$) cycloalkyl, —$(CH_2)_n$—($C_3$-$C_{10}$) heterocycle, —$(CH_2)_n$—($C_3$-$C_{10}$) aryl, or —$(CH_2)_n$—($C_3$-$C_{10}$) heteroaryl that may be substituted with at least one to 5 substituents independently selected from the group consisting of $C_{1-8}$ alkyl, $C_{1-4}$ alkoxyl, $C_{3-6}$ cycloalkyl, halogen, $C_{1-4}$ haloalkyl, carboxy, hydroxy, amino, oxo, phenyl and phenoxy, wherein n is an integer of 0 to 3, $R_3$ is ($C_1$-$C_6$) alkyl or —$(CH_2)_p$—($C_3$-$C_{10}$) aryl, and p is an integer of 0 to 3.

In specific examples, in Chemical formula 2, $R_1$, $R_2$, $R_4$ and $R_5$ are independently —$NR_8R_9$, in case of $R_1$ and $R_4$, $R_8$ and $R_9$ are independently hydrogen, ($C_1$-$C_6$) alkyl, —$(CH_2)_rNH_2$, —$(CH_2)_rN(H)C(=NH)NH_2$, or —$(CH_2)_rC(=O)OH$, or —$(CH_2)_rOH$ which may be substituted with $C_{1-4}$ alkoxyl, hydroxy or phenoxy, and r is an integer of 1 to 6; or in case of $R_2$ and $R_5$, $R_8$ and $R_9$ are independently hydrogen, ($C_1$-$C_6$) alkyl, —$(CH_2)_m$—($C_3$-$C_{10}$) cycloalkyl, $(CH_2)_m$—($C_3$-$C_{10}$) aryl, or —$(CH_2)_m$—($C_3$-$C_{10}$) heteroaryl which may be substituted with $C_{1-4}$ alkoxyl, hydroxy or phenoxy, and m is an integer of 0 to 3, and $R_3$ is ($C_1$-$C_6$) alkyl or benzyl.

In another example, in Chemical formula 2, $R_1$, $R_2$, $R_4$ and $R_5$ are independently —$NR_8R_9$, in case of $R_1$ and $R_4$, $R_8$ and $R_9$ are independently hydrogen or ($C_1$-$C_6$) alkyl, or in case of $R_2$ and $R_5$, $R_8$ and $R_9$ are independently $C_1$-$C_6$ alkyl, —$(CH_2)_m$-phenyl, —$(CH_2)_m$-phenoxyphenyl, —$(CH_2)_m$-benzodioxole, —$(CH_2)_m$-dialkoxylbenzene, —$(CH_2)_m$-dimethoxyphenyl, —$(CH_2)_m$-hydroxyphenyl, or —$(CH_2)_m$—($C_3$-$C_6$) cycloalkyl, and $R_3$ is ($C_1$-$C_6$) alkyl or benzyl.

In another example, in Chemical formula 2, $R_1$, $R_2$, $R_4$ and $R_5$ are independently —$NR_8R_9$, in case of $R_1$ and $R_4$, $R_8$ and $R_9$ are independently hydrogen or ($C_1$-$C_6$) alkyl, or in case of $R_2$ and $R_5$, $R_8$ and $R_9$ are independently $C_1$-$C_6$ alkyl, —$(CH_2)_m$-phenyl, —$(CH_2)_m$-phenoxyphenyl, —$(CH_2)_m$-benzodioxole, —$(CH_2)_m$-dialkoxylbenzene, —$(CH_2)_m$-dimethoxyphenyl, —$(CH_2)_m$-hydroxyphenyl, or —$(CH_2)_m$—($C_3$-$C_6$) cycloalkyl, and $R_3$ is ($C_1$-$C_6$) alkyl or benzyl.

As another embodiment, $R_1$, $R_2$, $R_4$ and $R_5$ in Chemical formula 2 are independently at least one selected from the following groups:

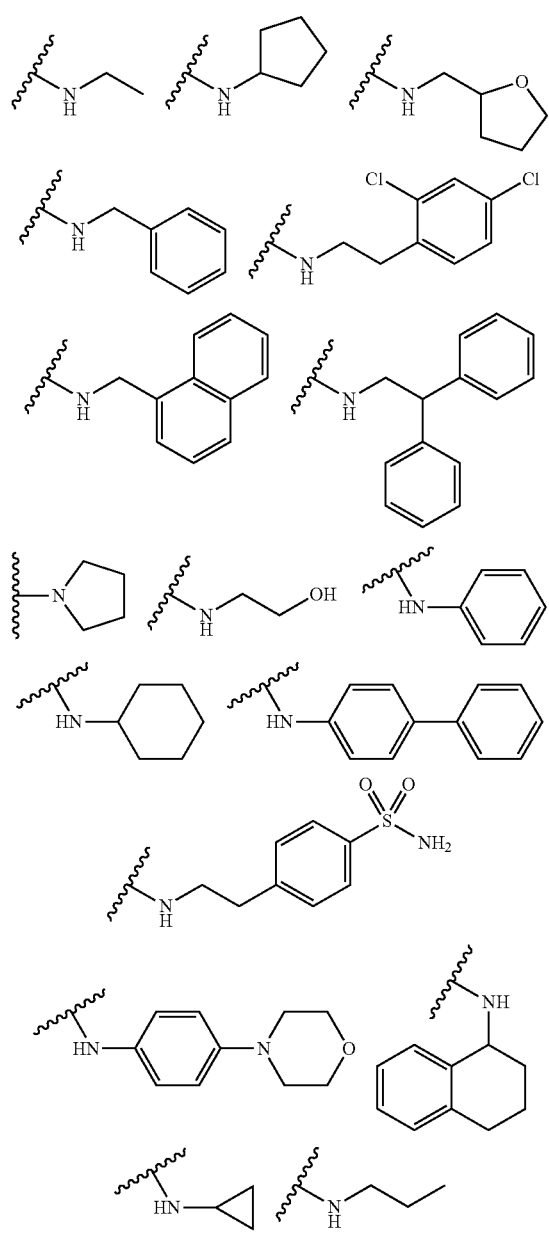

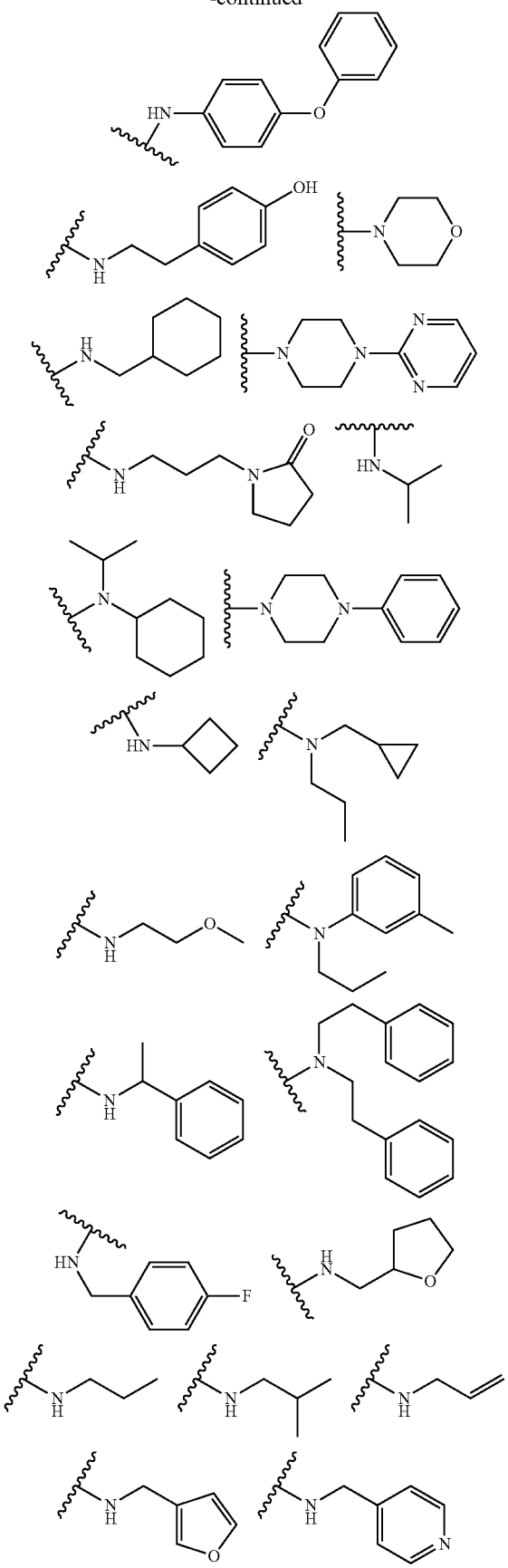

-continued

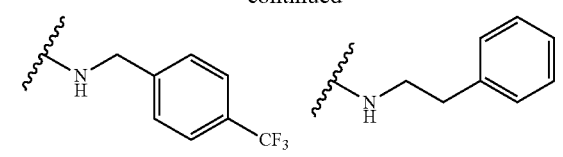
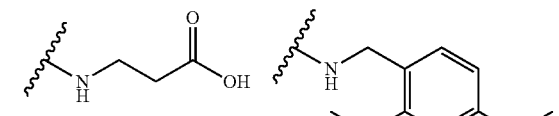
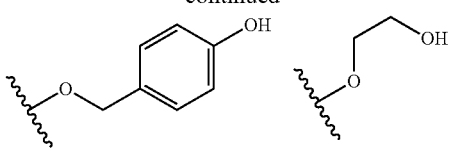
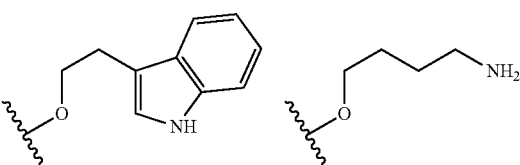
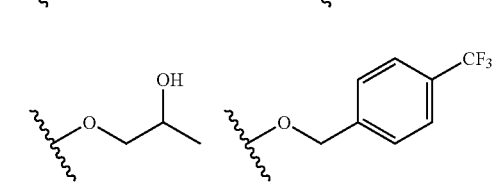
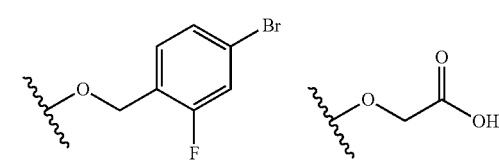
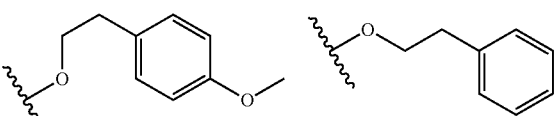
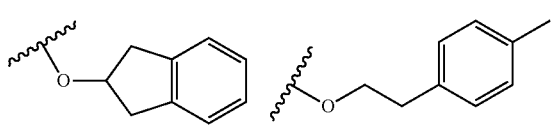
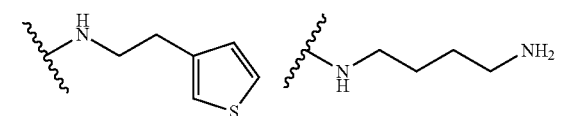
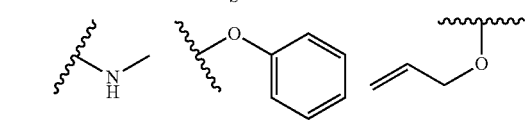
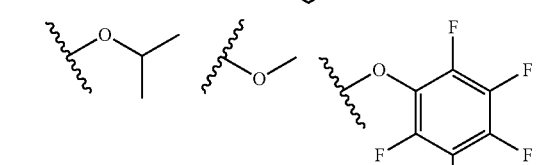
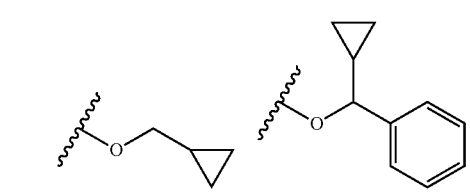
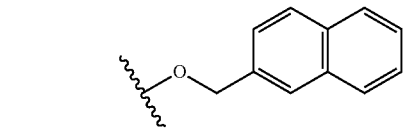
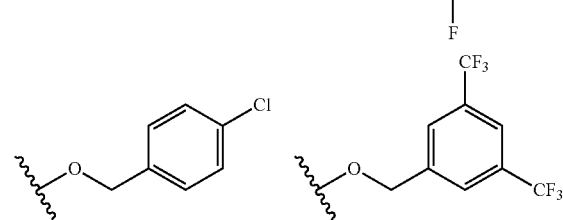
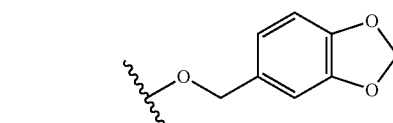
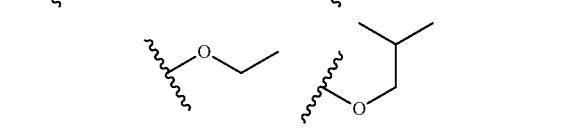
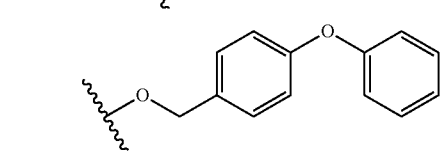

-continued

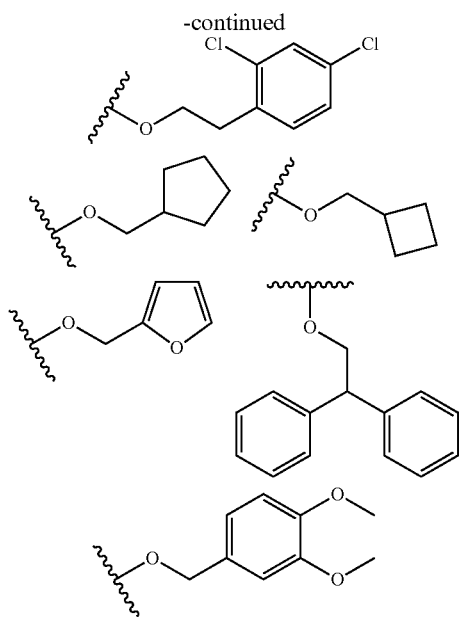

As another embodiment, $R_3$ in Chemical formula 2 are independently at least one selected from the following groups:

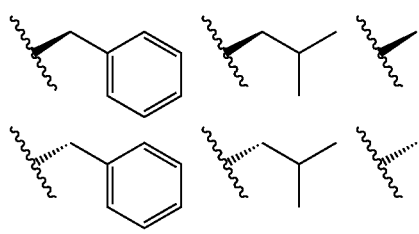

As another embodiment, the compounds of Chemical formula 2 and the compounds of Chemical formula 4 to Chemical formula 8 are at least one selected from the following groups:

[Chemical formula 4]

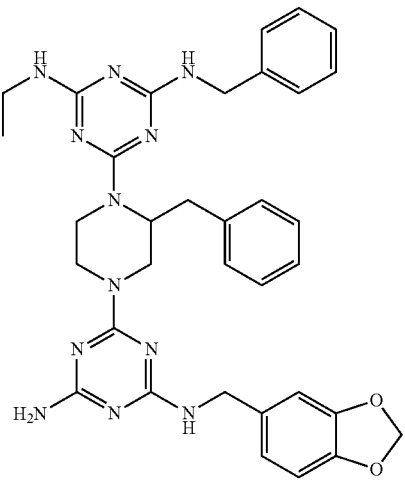

-continued

[Chemical formula 5]

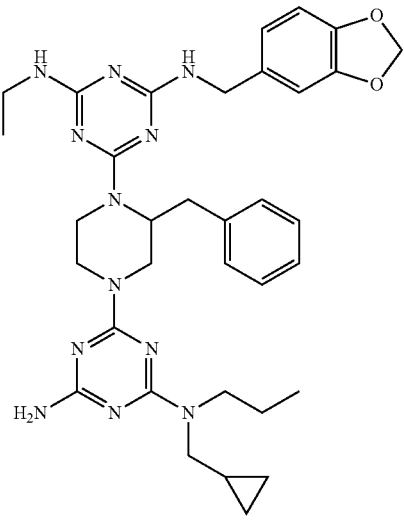

[Chemical formula 6]

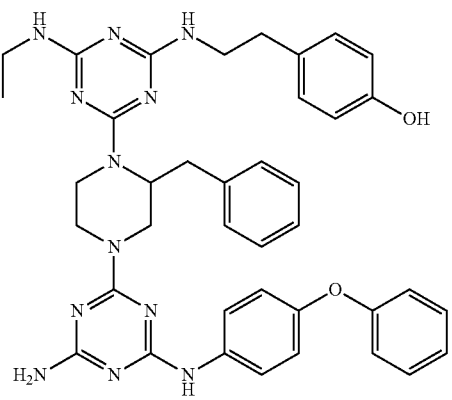

[Chemical formula 7]

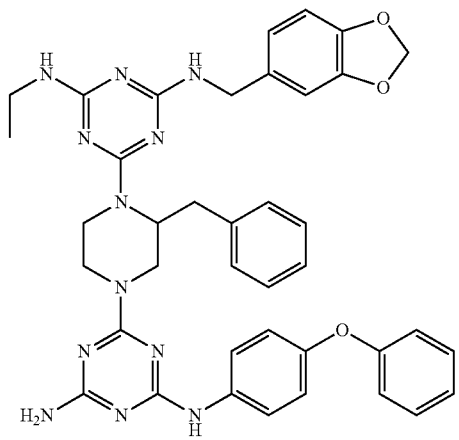

-continued

[Chemical formula 8]

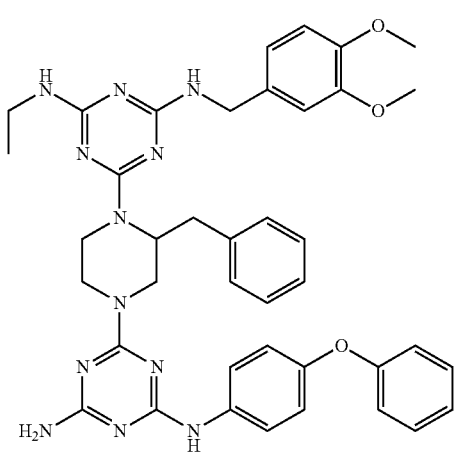

As another embodiment, the compound of present invention can be compound of Chemical formula 9:

[Chemical formula 9]

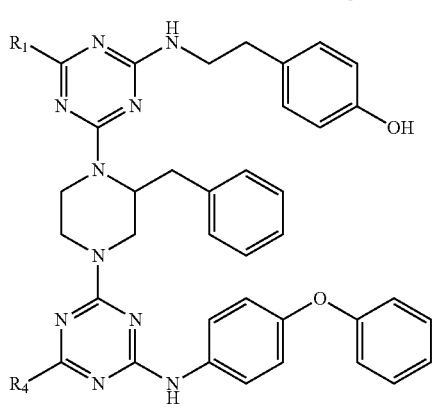

In Chemical formula 9, $R_1$ and $R_4$ are independently $-NR_8R_9$ or $-OR_{10}$, $R_8$ and $R_9$ are independently hydrogen, ($C_1$-$C_6$) alkyl, ($C_2$-$C_6$) alkenyl, ($C_2$-$C_6$) alkynyl, $-(CH_2)_m-(C_3$-$C_{10})$ cycloalkyl, $-(CH_2)_m-(C_4$-$C_{10})$ cycloalkenyl, $-(CH_2)_m-(C_3$-$C_{10})$ heterocycle, $-(CH_2)_m-(C_3$-$C_{10})$ aryl, or $-(CH_2)_m-(C_3$-$C_{10})$ heteroaryl that may be substituted with at least one to 5 substituents independently selected from the group consisting of $C_{1-8}$ alkyl, $C_{2-6}$ alkenyl, $C_{1-4}$ alkoxyl, $C_{3-6}$ cycloalkyl, halogen, $C_{1-4}$ haloalkyl, $C_3$-$C_{10}$ heteroaryl, $C_3$-$C_{10}$ heterocyclic, $-N-(C_3$-$C_{10})$ aryl, $-N-(C_3$-$C_{10})$ heteroaryl, carboxy, guanidyl, hydroxy, nitro, amino, phenyl, phenoxy, oxo and sulfonamide, and m is an integer of 0 to 3, $R_8$ and $R_9$ may be connected to each other to form a ring together with C, N or O, and $R_{10}$ is hydrogen, ($C_1$-$C_6$) alkyl, ($C_2$-$C_6$) alkenyl, ($C_2$-$C_6$) alkynyl, $-(CH_2)_n-(C_3$-$C_{10})$ cycloalkyl, $-(CH_2)_n-(C_3$-$C_{10})$ heterocycle, $-(CH_2)_n-(C_3$-$C_{10})$ aryl, or $-(CH_2)_n-(C_3$-$C_{10})$ heteroaryl that may be substituted with at least one to 5 substituents independently selected from the group consisting of $C_{1-8}$ alkyl, $C_{1-4}$ alkoxyl, $C_{3-6}$ cycloalkyl, halogen, $C_{1-4}$ haloalkyl, carboxy, hydroxy, amino, oxo, phenyl and phenoxy, wherein n is an integer of 0 to 3, Alternatively, in Chemical formula 9, $R_1$ and $R_4$ are independently $-NR_8R_9$, $R_8$ and $R_9$ are independently hydrogen, ($C_1$-$C_6$) alkyl, $-(CH_2)_rNH_2$, $-(CH_2)_rN(H)C(=NH)NH_2$, $-(CH_2)_rC(=O)OH$, or $-(CH_2)_rOH$, and r is an integer of 1 to 6.

As further embodiment of the present invention, the alpha-helix mimetic compound including phenyl-piperazine-triazine as a core structure and salts thereof are provided. The alpha-helix mimetic compound including phenyl-piperazine-triazine as a core structure is represented by Chemical formula 3:

[Chemical formula 3]

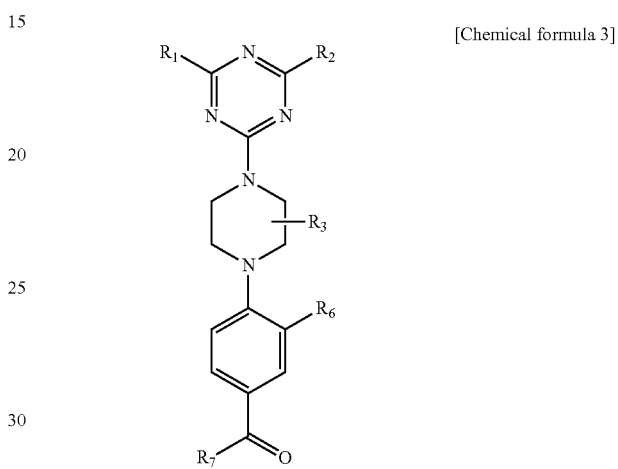

In Chemical formula 3, $R_1$ and $R_2$ are independently $-NR_8R_9$ or $-OR_{10}$, $R_8$ and $R_9$ are independently hydrogen, ($C_1$-$C_6$) alkyl, ($C_2$-$C_6$) alkenyl, ($C_2$-$C_6$) alkynyl, $-(CH_2)_n-(C_3$-$C_{10})$ cycloalkyl, $-(CH_2)_m-(C_4$-$C_{10})$ cycloalkenyl, $-(CH_2)_m-(C_3$-$C_{10})$ heterocycle, $-(CH_2)_m-(C_3$-$C_{10})$ aryl, or $-(CH_2)_m-(C_3$-$C_{10})$ heteroaryl that may be substituted with at least one to 5 substituents independently selected from the group consisting of $C_{1-8}$ alkyl, $C_{2-6}$ alkenyl, $C_{1-4}$ alkoxyl, $C_{3-6}$ cycloalkyl, halogen, $C_{1-4}$ haloalkyl, $C_3$-$C_{10}$ heteroaryl, $C_3$-$C_{10}$ heterocyclic, $-N-(C_3$-$C_{10})$ aryl, $-N-(C_3$-$C_{10})$ heteroaryl, carboxy, guanidyl, hydroxy, nitro, amino, phenyl, phenoxy, oxo and sulfonamide, wherein m is an integer of 0 to 3, $R_8$ and $R_9$ may be connected to each other to form a ring together with C, N or O, $R_{10}$ is hydrogen, ($C_1$-$C_6$) alkyl, ($C_2$-$C_6$) alkenyl, ($C_2$-$C_6$) alkynyl, $-(CH_2)_n-(C_3$-$C_{10})$ cycloalkyl, $-(CH_2)_n-(C_3$-$C_{10})$ heterocycle, $-(CH_2)_n-(C_3$-$C_{10})$ aryl, or $-(CH_2)_n-(C_3$-$C_{10})$ heteroaryl that may be substituted with at least one to 5 substituents independently selected from the group consisting of $C_{1-8}$ alkyl, $C_{1-4}$ alkoxyl, $C_{3-6}$ cycloalkyl, halogen, $C_{1-4}$ haloalkyl, carboxy, hydroxy, amino, oxo, phenyl and phenoxy, where n is an integer of 0 to 3, $R_3$ is ($C_1$-$C_6$) alkyl or $-(CH_2)_p-(C_3$-$C_{10})$ aryl, p is an integer of 0 to 3, $R_6$ is $-NR_{11}$, wherein $R_{11}$ is hydrogen, ($C_1$-$C_6$) alkyl, ($C_2$-$C_6$) alkenyl, ($C_2$-$C_6$) alkynyl, $-(CH_2)_q-(C_3$-$C_{10})$ cycloalkyl, $-(CH_2)_m-(C_4$-$C_{10})$ cycloalkenyl, $-(CH_2)_q-(C_3$-$C_{10})$ heterocycle, $-(CH_2)_q-(C_3$-$C_{10})$ aryl, or $-(CH_2)_q-(C_3$-$C_{10})$ heteroaryl that may be substituted with at least one to 5 substituents independently selected from the group consisting of $C_{1-8}$ alkyl, $C_{2-6}$ alkenyl, $C_{1-4}$ alkoxyl, $C_{3-6}$ cycloalkyl, halogen, $C_{1-4}$ haloalkyl, $C_3$-$C_{10}$ heteroaryl, $C_3$-$C_{10}$ heterocyclic, carboxy, guanidyl, hydroxy, nitro, amino, phenyl, phenoxy, oxo and sulfonamide, and q is an integer of 0 to 3, $R_{11}$ may be connected to each other to form a ring together with C or O, and $R_7$ is —$NH_2$.

In a specific example, in Chemical formula 3, $R_1$ and $R_2$ are independently —$NR_8R_9$, where $R_8$ is hydrogen, $R_9$ is hydrogen, $C_1$-$C_6$ alkyl or —$(CH_2)_m$—$(C_3$-$C_{10})$aryl, and m is an integer of 0 to 3, $R_3$ is ($C_1$-$C_6$) alkyl or benzyl, $R_6$ is —$NR_{11}$, where $R_{11}$ is ($C_1$-$C_6$) alkyl or —$(CH_2)_q$—($C_3$-$C_{10}$) aryl and q is an integer of 0 to 3, and $R_7$ is —$NH_2$, In another embodiment, $R_1$ and $R_2$ are independently selected from the group consisting of the compounds represented by the following chemical structures:

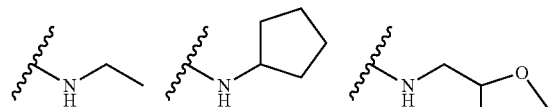
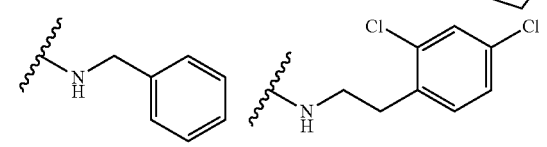
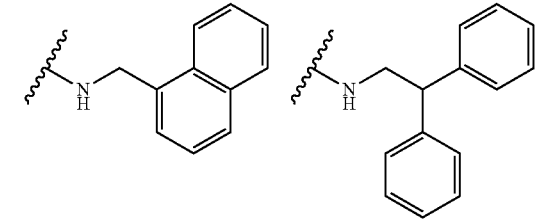
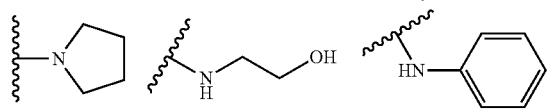
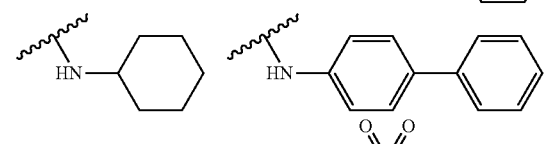
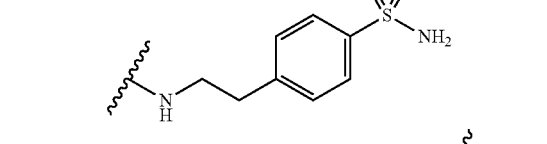
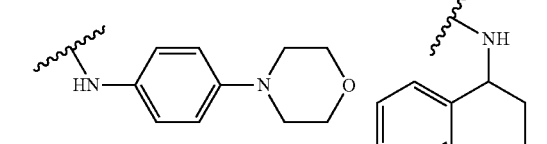
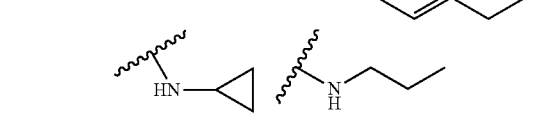

-continued

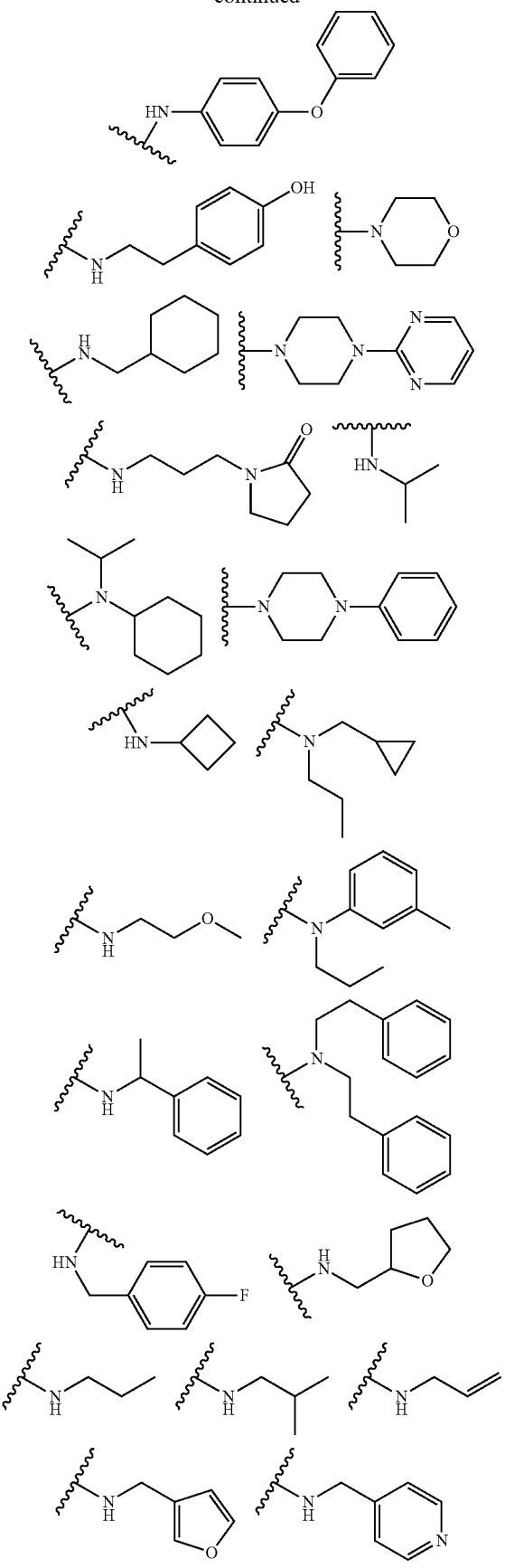

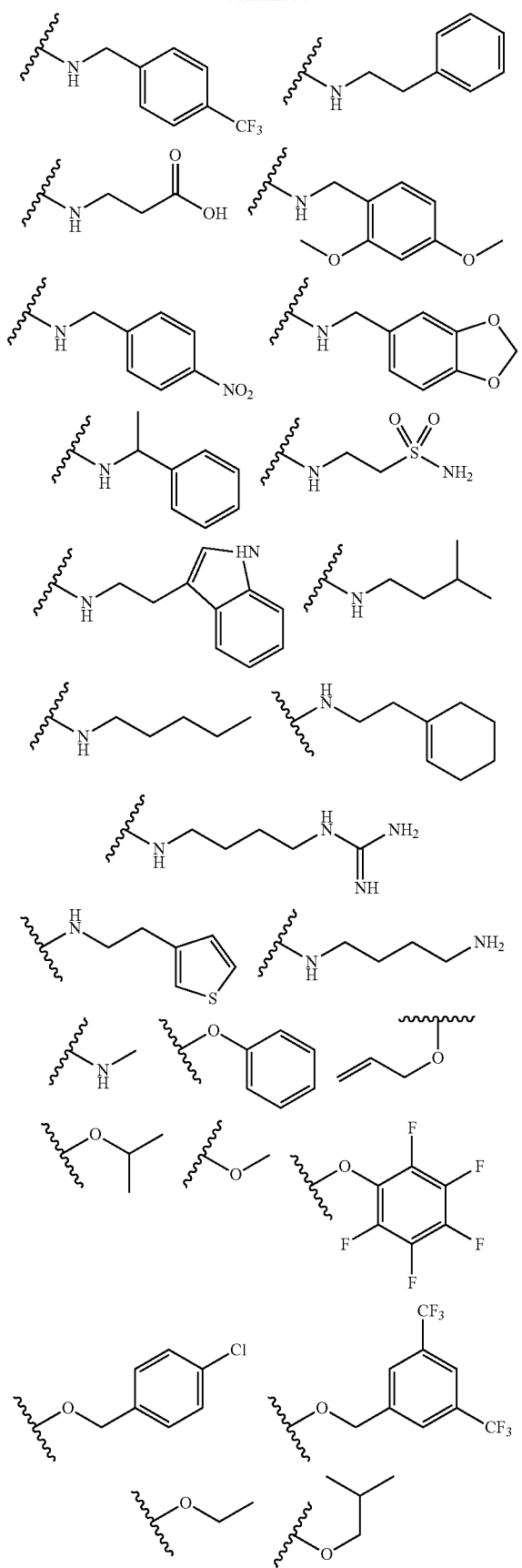
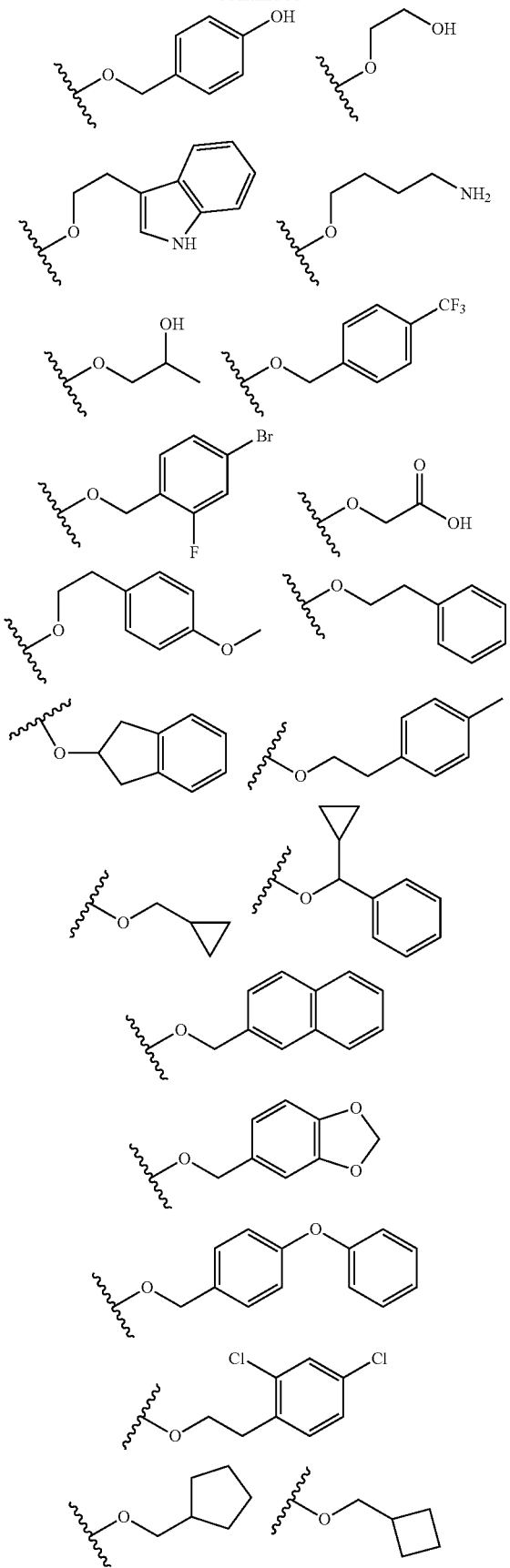

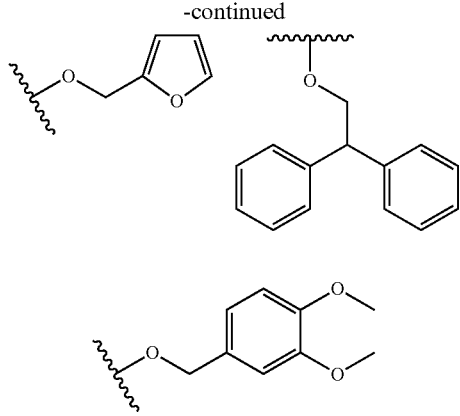
In further embodiment, R$_3$ of chemical formula 3 is independently selected from the groups represented by the following chemical structures:
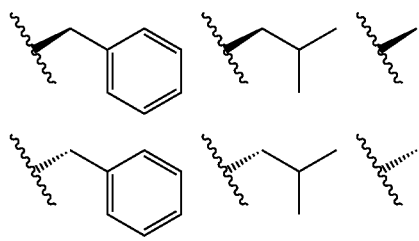
In further embodiment, R$_6$ of Chemical formula 3 is at least one selected from the following groups:
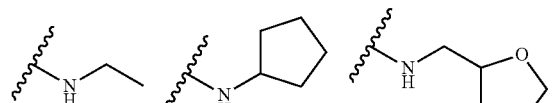
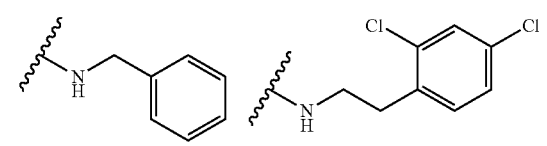
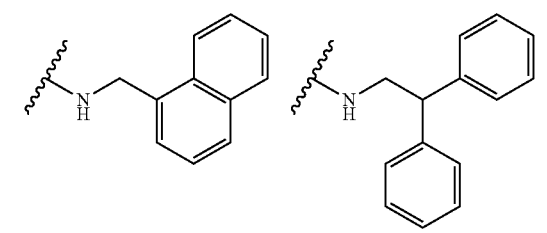
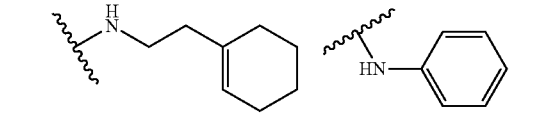
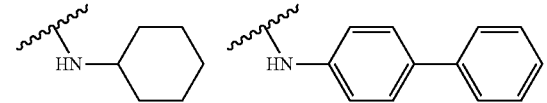
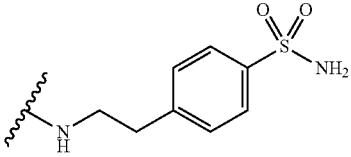
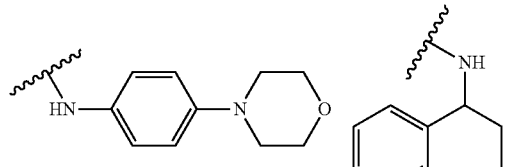
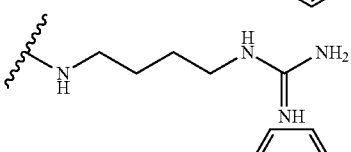
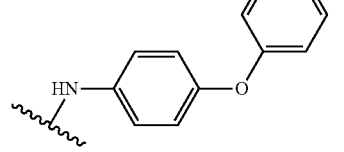
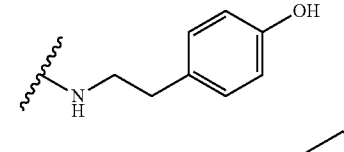
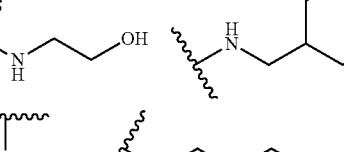
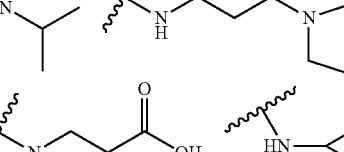
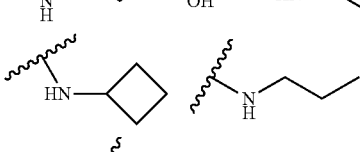
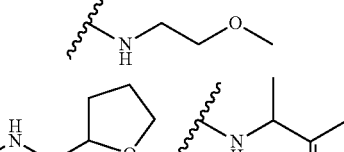
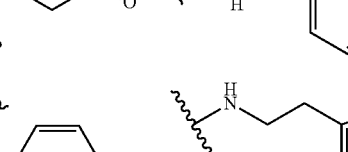
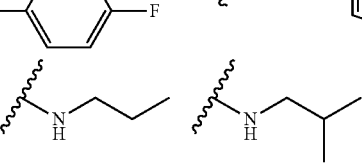

-continued

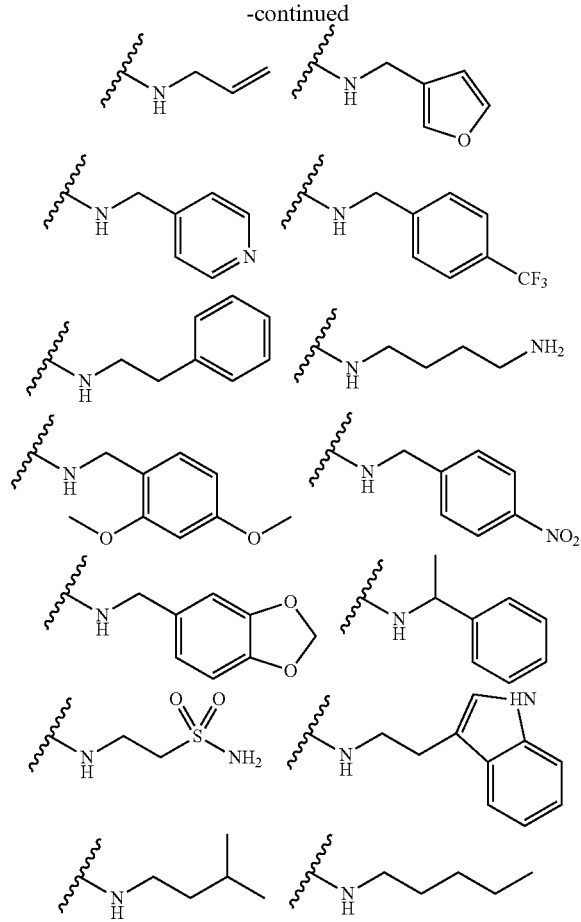

In another embodiment, $R_1$, $R_2$, $R_3$, $R_6$ and $R_7$ of Chemical formula 3 are independently at least one selected from the following groups:

TABLE 1

| R1 | R2 | R3 | R6 | R7 |
|---|---|---|---|---|
| NHEt | NHiPr | iBu | NHEt | $NH_2$ |
| NHEt | NHiBu | iBu | NHEt | $NH_2$ |
| NHEt | NHBn | iBu | NHEt | $NH_2$ |
| NHEt | NHNaph | iBu | NHEt | $NH_2$ |
| NHEt | NHiPr | Bn | NHEt | $NH_2$ |
| NHEt | NHiBu | Bn | NHEt | $NH_2$ |
| NHEt | NHBn | Bn | NHEt | $NH_2$ |
| NHEt | NHNaph | Bn | NHEt | $NH_2$ |
| NHEt | NHiPr | Me | NHEt | $NH_2$ |
| NHEt | NHiBu | Me | NHEt | $NH_2$ |
| NHEt | NHBn | Me | NHEt | $NH_2$ |
| NHEt | NHNaph | Me | NHEt | $NH_2$ |
| NHEt | NHiPr | iBu | NHiBu | $NH_2$ |
| NHEt | NHiBu | iBu | NHiBu | $NH_2$ |
| NHEt | NHBn | iBu | NHiBu | $NH_2$ |
| NHEt | NHNaph | iBu | NHiBu | $NH_2$ |
| NHEt | NHiPr | Bn | NHiBu | $NH_2$ |
| NHEt | NHiBu | Bn | NHiBu | $NH_2$ |
| NHEt | NHBn | Bn | NHiBu | $NH_2$ |
| NHEt | NHNaph | Bn | NHiBu | $NH_2$ |
| NHEt | NHiPr | Me | NHiBu | $NH_2$ |
| NHEt | NHiBu | Me | NHiBu | $NH_2$ |
| NHEt | NHBn | Me | NHiBu | $NH_2$ |
| NHEt | NHNaph | Me | NHiBu | $NH_2$ |
| NHEt | NHiPr | iBu | NHBn | $NH_2$ |
| NHEt | NHiBu | iBu | NHBn | $NH_2$ |
| NHEt | NHBn | iBu | NHBn | $NH_2$ |
| NHEt | NHNaph | iBu | NHBn | $NH_2$ |

TABLE 1-continued

| R1 | R2 | R3 | R6 | R7 |
|---|---|---|---|---|
| NHEt | NHiPr | Bn | NHBn | $NH_2$ |
| NHEt | NHiBu | Bn | NHBn | $NH_2$ |
| NHEt | NHBn | Bn | NHBn | $NH_2$ |
| NHEt | NHNaph | Bn | NHBn | $NH_2$ |
| NHEt | NHiPr | Me | NHBn | $NH_2$ |
| NHEt | NHiBu | Me | NHBn | $NH_2$ |
| NHEt | NHBn | Me | NHBn | $NH_2$ |
| NHEt | NHNaph | Me | NHBn | $NH_2$ |

In another embodiment, the compound of Chemical formula 3 is specifically the compound of Chemical formula 10:

[Chemical formula 10]

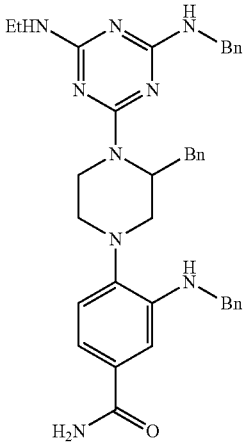

In the compound of the present invention, $R_2$, $R_3$, $R_5$ and $R_6$ are located in the three-dimensional space corresponding to three amino acids (amino acid residues at i, i+3/i+4, i+7) which act as recognition motif of natural alpha-helix binding to a protein, thereby allowing the alpha-helix mimetic compound to bind to a target protein.

In addition, $R_1$ and $R_4$ may include a hydrophilic group preferably, but not limited thereto. When $R_1$ and $R_4$ may include a hydrophilic group, the alpha-helix mimetic compounds are amphiphilic. Most of the natural alpha-helix peptides include hydrophobic residues on one side and play an important role as recognition motifs when binding to other proteins, while the alpha-helix peptide include hydrophilic amino acid residues on the opposite side and these hydrophilic residues face outwards and place in the exposed area when the alpha-helix peptide is attached to the protein. Thus, the alpha-helix peptide is in an energetically favorable state. The hydrophilic residues of the alpha-helix peptide have hydrophilic interaction with amino acids on surface of target protein, when the alpha-helix peptide binds to the target protein. Besides the hydrophobic interaction, the hydrophilic interaction can make the alpha-helix peptide bind to the target protein stronger. Accordingly, as a preferred embodiment, the present invention provides the alpha-helix mimetic compounds having a hydrophilic substituent and a hydrophobic substituent, and mimics the amphiphilic property of the natural alpha-helix. The alpha-helix mimetic compounds which have been developed up to now are hardly the alpha-helix mimetic compounds having the amphiphilic property.

Therefore, as a preferred embodiment, the alpha-helix mimetic compounds of the present invention include a triazine-piperazine as a core structure and three substituents ($R_2$, $R_3$, $R_5$, or $R_2$, $R_3$, $R_6$) play largely an important role in binding to the target protein through the hydrophobic interaction, and two substituents ($R_1$, $R_4$) located on the opposite side of the three substituents include a hydrophilic group and mimics the amphiphilic property of natural alpha-helix, thereby being designed as a strong inhibitor of protein-protein interaction. The properties of alpha-helix mimetic compound in accordance with the present invention are shown roughly in FIG. 1.

As shown in FIG. 1, when the compounds of present invention having a triazine-piperazine-triazine scaffold and the convention compounds having terphenyl scaffold are synthesized at lowest-energy state, C log P (calculated log $P_{octanol/water}$) of the present compound and conventional compound are 1.366, and 6.21 respectively. Thus, the compounds of present invention show more improved hydrophilic property, thereby achieving the properties being similar to a drug.

In the definition of substituents herein, the term "alkyl" refers to an aliphatic hydrocarbon radical. Alkyl may be "saturated alkyl" that does not include an alkenyl or alkynyl moiety or an "unsaturated alkyl" that includes at least one alkenyl or alkynyl moiety. "alkenyl (alkenyl)" means a group containing at least one carbon-carbon double bond, and "alkynyl (alkynyl)" means a group containing at least one carbon-carbon triple bond. Alkyl may be branched or straight chain, when being used alone or in combination with alkoxyl.

The alkyl group may include 1 to 20 carbon atoms, unless otherwise defined. The alkyl group may be a medium-sized alkyl having 1 to 10 carbon atoms. The alkyl group may be lower alkyl having 1 to 6 carbon atoms. Typical alkyl groups include, but are not limited to, methyl, ethyl, propyl, iso-propyl, butyl, isobutyl, t-butyl, pentyl, hexyl, ethenyl, propenyl, butenyl and the like. For example, $C_1$-$C_4$-alkyl includes 1 to 4 carbon atoms in the alkyl chain and is selected from the group consisting of methyl, ethyl, propyl, iso-propyl, n-butyl, iso-butyl, sec-butyl and t-butyl.

The term "alkoxyl" means alkyloxy having 1 to 10 carbon atoms, unless otherwise defined. For examples, the alkoxy groups may be methoxy, ethoxy, n-propoxy, iso-propoxy, n-butoxy, t-butoxy, iso-butoxy, sec-butoxy and the like.

The term "cycloalkyl," unless otherwise defined, means a saturated aliphatic 3- to 10-membered ring. Typical cycloalkyl groups include, but are not limited to, cyclopropyl, cyclobutyl, cyclopentyl, cyclohexyl, and the like.

The term "aryl" includes at least one ring having a covalent pi electron system and includes, for example, a monocyclic or fused ring polycyclic group (i.e., rings that shares adjacent pairs of carbon atoms). That is, herein, aryl may mean a 4- to 10-membered, preferably 6- to 10-membered aromatic monocyclic or polycyclic ring such as phenyl, naphthyl or the like, unless otherwise defined.

The term "heteroaryl" means an aromatic 3- to 10-membered, preferably 4- to 8-membered ring, more preferably a 5- to 6-membered ring containing 1 to 3 heteroatoms selected from the group consisting of N, O and S which may be fused with benzo or C3-C8 cycloalkyl. Examples of monocyclic heteroaryls include thiazole, oxazole, thiophene, furan, pyrrole, imidazole, isoxazole, isothiazole, pyrazole, triazole, triazine, thiadiazole, tetrazole, oxadiazole, pyridine, pyridazine, pyrimidine, pyrazine, and similar groups. Examples of cyclic heteroaryl include, but are not limited to, indole, indoline, benzothiophene, benzofuran, benzodioxole, benzimidazole, benzoxazole, benzisoxazole, benzthiazole, benzthiadiazole, benztriazole, quinoline, isoquinoline, purine, puropyridine, and similar groups.

The term "heterocycle," unless otherwise defined, 3- to 10-membered ring, preferably a 4- to 8-membered ring, more preferably a 5- to 6-membered ring including 1 to 3 heteroatoms selected from the group consisting of N, O and S, being capable of fusing with benzo or $C_3$-$C_8$ cycloalkyl, and being saturated or 1 or 2 double bond. Examples of the heterocycles include pyrroline, pyrrolidine, imidazoline, imidazolidine, pyrazoline, pyrazolidine, pyran, piperidine, morpholine, thiomorpholine, piperazine and hydrofuran, but are not limited thereto.

The term "arylalkyl" means a $C_1$-$C_4$ alkylene such as —$CH_2$—, —$CH_2CH_2$— and the like which may be further substituted by an aryl group. The examples of arylalkyl are benzyl, phenetylene and the like.

The term "cycloalkenyl" refers to a non-aromatic ring radical containing from 4 to 10 cyclic carbons and one or more double bonds. The some examples contain 4 to 6 carbons, and other examples contain 4 or 5 carbons, and some embodiments contain 4 carbons. Examples of the cycloalkenyl include cyclobutenyl, cyclopentenyl, cyclohexenyl, and the like.

The term "cycloalkyl" refers to a saturated ring radical containing 3 to 10 carbons, some embodiments contain 3 to 6 carbons, some embodiments contain 3 to 5 carbons, some embodiments contains 5 to 7 carbons, and some embodiments contain 3 or 4 carbons. Examples include cyclopropyl, cyclobutyl, cyclopentyl, cyclohexyl, cycloheptyl, and the like.

The term "halogen" or "halo" means fluoro, chloro, bromo or iodo.

The term "haloalkyl" refers to a $C_{1-6}$ alkyl group as defined herein, where alkyl is substituted with one halogen and substituted fully with halogen. The fully-substituted $C_{1-6}$ haloalkyl is represented by Chemical formula $C_nL_{2n+1}$, where L is a halogen, and N is 1, 2, 3, 4, 5 or 6. The haloalkyl with one or more halogen atom may be the same or different and are selected from the group consisting of F, Cl, Br and I. Examples of the haloalkyl groups include, but are not limited to, fluoromethyl, difluoromethyl, trifluoromethyl, chlorodifluoromethyl, 2,2,2-trifluoroethyl, pentafluoroethyl and the like.

The term "amino" represents —NH$_2$ group.

The term "benzyl" refers to —CH$_2$C$_6$H$_5$.

The term "carboxy" or "carboxyl" refers to —CO$_2$H group and can be called as carboxylic acid.

The term "hydroxy" refers to —OH group.

The term "nitro" refers to —NO$_2$ group.

Herein, the term "oxo" substituent refers to =O, and carbonyl group is produced from carbon and oxo, when carbon is substituted with oxo group.

The term "phenoxy" refers to C$_6$H$_5$O— group.

The term "phenyl" refers to C$_6$H$_5$— group.

The term "sulfonamide" refers to —SO$_2$NH$_2$ group.

Other terms and abbreviations used herein are to be understood as meaning commonly understood by those skilled in the art to which the present invention belongs, unless otherwise defined.

The compounds according to the invention may also form pharmaceutically acceptable salts.

Such term "pharmaceutically acceptable salt" may include acids forming non-toxic acid addition salts containing a pharmaceutically acceptable anion, for example acid addition salts formed by inorganic acids such as sulfuric acid, hydrochloric acid, nitric acid, phosphoric acid, hydrobromic acid, hydroiodic acid and the like; organic carboxylic acids such as tartaric acid, formic acid, citric acid, acetic acid, trichloroacetic acid, trifluoroacetic acid, gluconic acid, benzoic acid, lactic acid, fumaric acid, maleic acid, salicylic acid and the like; sulfonic acids such as methanesulfonic acid, ethanesulfonic acid, benzenesulfonic acid, p-toluenesulfonic acid, naphthalenesulfonic acid, and the like. In addition, the salts include pharmaceutically acceptable base addition salts such as alkali or alkaline earth metal salts formed by lithium, sodium, potassium, calcium, magnesium and the like; Amino acid salts such as lysine, arginine and guanidine; Organic salts such as dicyclohexylamine, N-methyl-D-glucamine, tris (hydroxy methyl) methylamine, diethanolamine, choline, triethylamine and the like. The compound according to the present invention can be converted into a salt thereof by a general method, and the preparation of the salt can be easily carried out by a person skilled in the art based on the structure of the formulas without further explanation.

In another embodiment, the present invention relates to a method for preparing an alpha-helix mimetic compound having triazine-piperazine-triazine as a core structure.

For example, the method of the present invention may include the following steps:

preparing a compound of Chemical formula (b) by connecting compound of Chemical formula (a) to polymer bead modified by amine (NH$_2$), preparing a compound of Chemical formula (d) by coupling compound of Chemical formula (b) with a compound of Chemical formula (c) protected by 2-nitrobenzene sulfonyl, preparing a compound of Chemical formula (f) by introducing a compound of Chemical formula (e), after removing 2-nitrobenzene sulfonyl protecting group from compound of Chemical formula (d), substituting chloride position of compound represented by Chemical formula (f) with amine group (R$_2$"R$_2$"NH), and removing the polymer bead modified by amine (NH$_2$).

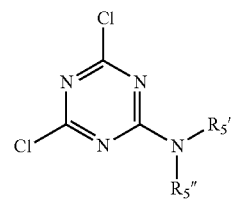

[Chemical formula a]

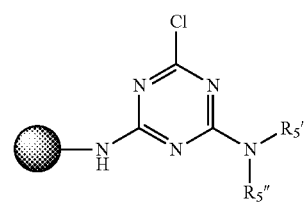

[Chemical formula b]

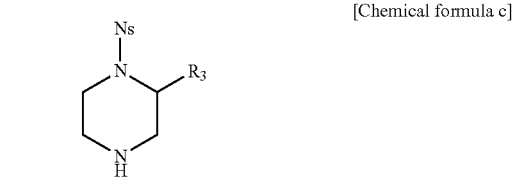

[Chemical formula c]

[Chemical formula d]

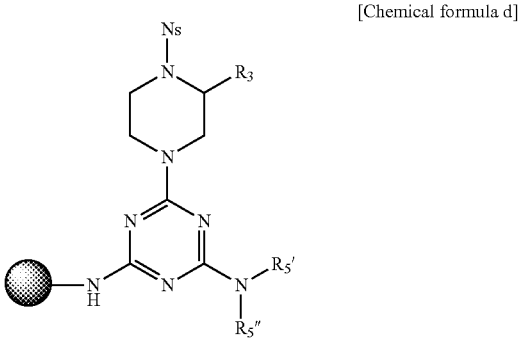

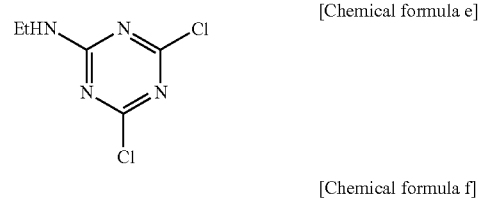

[Chemical formula e]

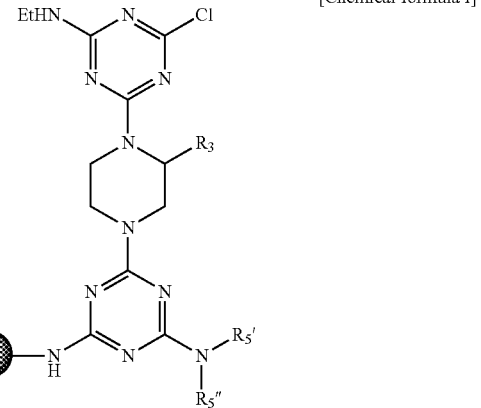

[Chemical formula f]

As provide in the preparation method, the alpha-helix mimetic compound of the present invention can be prepared by a very simple solid phase synthesis. The interest compound can be obtained by several steps of sequential coupling reaction in the amine-modified polymer bead at average yield of 92%. The preparation method is described in more detail by referring to FIG. 2. As a first step, monosubstituted dichlorotriazine ("3") can be loaded onto a Rink-Amide MBHA resin to bind to the resin to produce a triazine derivative ("4") bound to the resin. As a second step, Compound "6" can be prepared by coupling a piperazine derivative ("5") protected with 2-nitrobenzene sulfonyl (Ns) to a triazine derivative ("4") attached to a resin. As a third step, after removing N-Ns protecting group from the coupled compound ("6"), compound ("8") can be prepared by introducing 2-ethylamino-4,6-dichloro-[1,3,5]triazine ("7") to the deprotected compound. As a fourth step, various amines ($R_2R_2'H$) can be introduced to at chloride site of the prepared compound ("8"). As a fifth step, compound ("9") functionalized with three substituents can be prepared by performing cleavage reaction with addition of TFA (trifluoroacetic acid)

In another aspect, the present invention relates to a method for preparing an alpha-helix mimetic compound having phenyl-piperazine-triazine as a core structure.

preparing a compound of Chemical formula (b') by connecting 4-fluoro-3-nitrobenzoic acid a to polymer bead modified by amine ($NH_2$), preparing a compound of Chemical formula (d') by coupling compound of Chemical formula (b') with a compound of Chemical formula (c') protected by 2-nitrobenzene sulfonyl, preparing a compound of Chemical formula f" by introducing a compound of Chemical formula (e'), after removing 2-nitrobenzene sulfonyl protecting group from compound of Chemical formula (d'), preparing a compound of Chemical formula (g') by substituting chloride in compound of Chemical formula (f') with amine group ($R_3NH$) and reducing the nitro group, preparing a compound of Chemical formula (h') by introducing $R_1$ functional group to compound of Chemical formula (g'), and removing polymer bead modified by amine ($NH_2$).

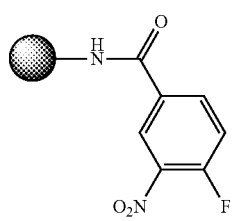

[Chemical formula b']

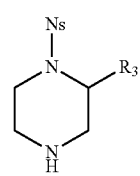

[Chemical formula c']

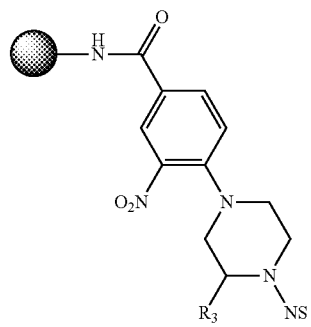

[Chemical formula d']

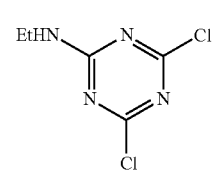

[Chemical formula e']

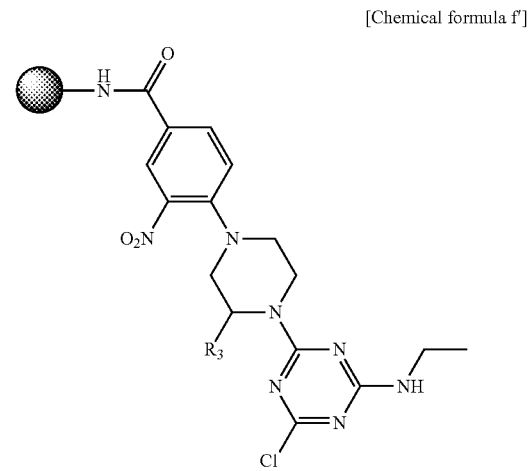

[Chemical formula f']

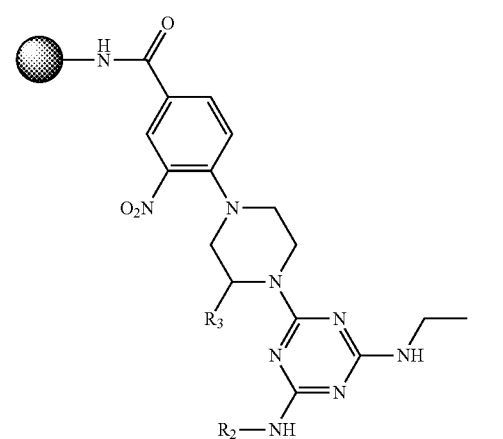

[Chemical formula g']

[Chemical formula h']

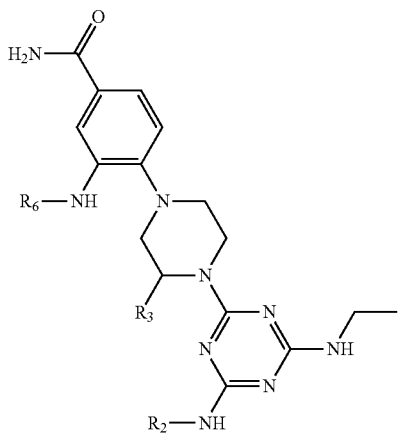

As provide in the preparation method, the alpha-helix mimetic compound of the present invention can be prepared by a very simple solid phase synthesis. The interest compound can be obtained by several steps of sequential coupling reaction in the amine ($NH_2$)-modified polymer bead at average yield of 90%.

In another aspect, the present invention relates to a composition for inhibiting a protein-protein interaction, comprising the alpha-helix mimetic compound or a salt thereof.

In another aspect, the present invention relates to a method for inhibiting a protein-protein interaction, comprising the step of treating the alpha-helix mimetic compound or a salt thereof with a target protein.

In another aspect, the present invention relates to a composition for detecting a protein-protein interaction, including the alpha-helix mimetic compound or a salt thereof.

In another aspect, the present invention relates to a method for detecting a protein-protein interaction, comprising the step of treating the alpha-helix mimetic compound or a salt thereof with a target protein.

The alpha-helix mimetic compound provided in the present invention can mimic the structure of alpha-helix peptide existing in nature and effectively mimic the function of alpha-helix peptide and thus can be used as a strong inhibitor of protein-protein interaction. It can also be used as a probe to detect protein-protein interaction, using the property of binding to the target protein.

In the present invention, a chemical library containing alpha-helix mimetic compounds of the present invention is provided. The library includes amphipathic alpha-helix mimetic compounds having a triazine-piperazine core structure, and can screening the compounds that bind specifically to the target protein on the basis of characteristic of target protein. The target proteins can be, but are not limited to, antibodies, enzymes, receptors or cell lines.

In the present invention, the interaction between protein and protein includes binding between protein and protein, or aggregation between protein and protein. This interaction can be, for example, between two membrane-bound proteins, between membrane-bound proteins and cytoplasmic proteins (for example, receptors and ligands), between cytoplasmic proteins, and the like. Preferably, the invention can be applied to protein-protein interactions through the alpha-helix structure.

In an embodiment of the present invention, the screening of an alpha-helix mimetic compound that inhibits and detects the interaction between the MCL-1 (myeloid cell leukemia-1) protein and the BCL-2 (B-cell lymphoma 2) protein (that is, protein-protein binding), and the interaction between α-synuclein proteins (that is, protein-protein aggregation) are provided, but this is only a representative example, and the scope of the present invention is not limited thereto.

In another aspect, the present invention relates to a pharmaceutical composition for treating a disease mediated by alpha-helix, which comprises the alpha-helix mimetic compound or a salt thereof.

In another aspect, the present invention relates to a method for treating a disease associated with alpha-helix-mediated interaction between proteins, comprising administering to said individual an effective amount of said alpha-helix mimetic compound or salt thereof.

For example, the present invention relates to a pharmaceutical composition for preventing or treating cancer, which comprises at least one compound or its pharmaceutically acceptable salt selected from the group consisting of compounds of Chemical formula 4 to Chemical formula 6, and Chemical formula 9 and Chemical formula 10. In another example, the present invention relates to a method for treating a cancer, comprising administering to said individual an effective amount of said alpha-helix mimetic compound or salt thereof selected from the group consisting of compounds of Chemical formula 4 to Chemical formula 6, Chemical formula 9 and Chemical formula 10:

[Chemical formula 4]

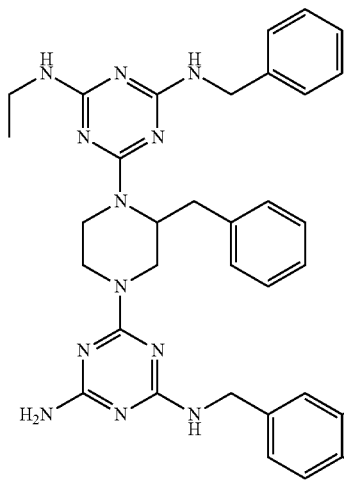

[Chemical formula 5]

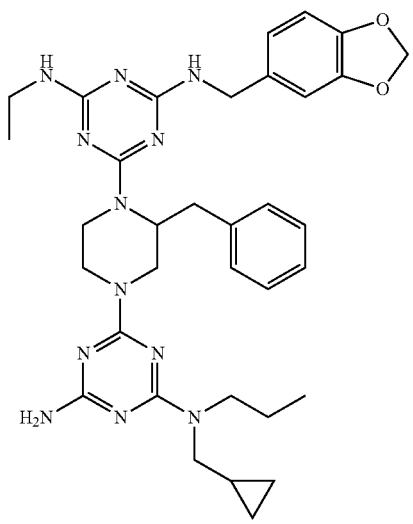

-continued

[Chemical formula 6]

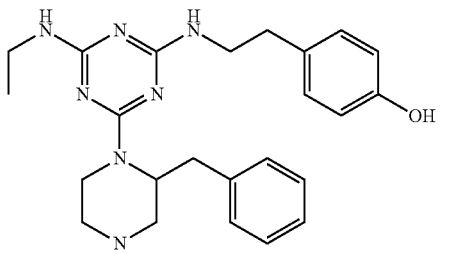

[Chemical formula 9]

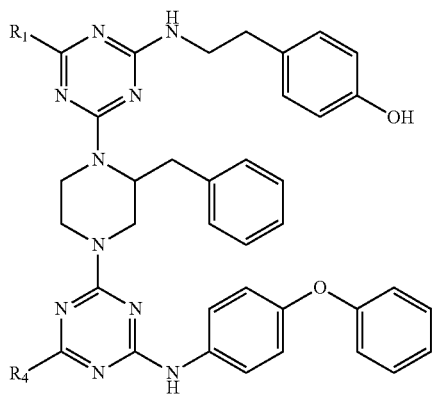

[Chemical formula 10]

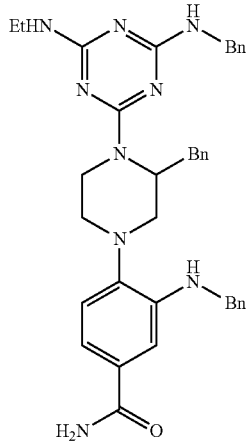

In the chemical formulae, $R_1$ and $R_4$ are independently —$NR_8R_9$ or —$OR_{10}$, $R_8$ and $R_9$ are independently hydrogen, ($C_1$-$C_6$) alkyl, ($C_2$-$C_6$) alkenyl, ($C_2$-$C_6$) alkynyl, —$(CH_2)_m$—($C_3$-$C_{10}$) cycloalkyl, —$(CH_2)_m$—($C_4$-$C_{10}$) cycloalkenyl, —$(CH_2)_m$—($C_3$-$C_{10}$) heterocycle, —$(CH_2)_m$—($C_3$-$C_{10}$) aryl, or —$(CH_2)_m$—($C_3$-$C_{10}$) heteroaryl that may be substituted with at least one to 5 substituents independently selected from the group consisting of $C_{1-8}$ alkyl, $C_{2-6}$ alkenyl, $C_{1-4}$ alkoxyl, $C_{3-6}$ cycloalkyl, halogen, $C_{1-4}$ haloalkyl, $C_3$-$C_{10}$ heteroaryl, $C_3$-$C_{10}$ heterocyclic, —N—($C_3$-$C_{10}$) aryl, —N—($C_3$-$C_{10}$) heteroaryl, carboxy, guanidyl, hydroxy, nitro, amino, phenyl, phenoxy, oxo and sulfonamide, and m is an integer of 0 to 3, $R_8$ and $R_9$ is connected to each other to form a ring together with C, N or O, $R_{10}$ is hydrogen, ($C_1$-$C_6$) alkyl, ($C_2$-$C_6$) alkenyl, ($C_2$-$C_6$) alkynyl, —$(CH_2)_n$—($C_3$-$C_{10}$) cycloalkyl, —$(CH_2)_n$—($C_3$-$C_{10}$) heterocycle, —$(CH_2)_n$—($C_3$-$C_{10}$) aryl, or —$(CH_2)_n$—($C_3$-$C_{10}$) heteroaryl that may be substituted with at least one to 5 substituents independently selected from the group consisting of $C_{1-8}$ alkyl, $C_{1-4}$ alkoxyl, $C_{3-6}$ cycloalkyl, halogen, $C_{1-4}$ haloalkyl, carboxy, hydroxy, amino, oxo, phenyl and phenoxy, and n is an integer of 0 to 3.

MCL-1 (myeloid cell leukemia-1) is one of BCL-2 (B-cell lymphoma 2) family proteins with anti-apoptotic activity. MCL-1 inhibits the cell apoptosis caused by BH3 and helps the cell survival by interacting with BH3 (BCL-2 homology domain 3) family proteins such as BAK. Therefore, the inhibition of interaction between MCL-1 protein and BH3 protein in cancer cells can prevent the cancer cell survival, thereby being a promising strategy for anti-cancer therapy.

In the present invention, in order to prove that a triazine-piperazine-triazine compound can serve as an alpha-helix mimetic for inhibiting inter-protein interaction, the compounds inhibiting interaction between BH3 protein and MCL-1 protein can be selected from the library of the present invention. In order to select alpha-helix mimetic compounds inhibiting MCL-1/BH3 protein interaction, the present inventors constructs the chemical library having triazine-piperazine-triazine as core structure on the polymer bead, and select the compounds directly binding to MCL-protein according to on-bead screening method in FIG. 4.

As a result, it was confirmed that compounds of chemical formula 4 to 6 bind to MCL-1 and inhibit the interaction between MCL-1 and BH3 protein, and these compounds were found to induce apoptosis of cancer cells (FIG. 6 to FIG. 10). Further, in the present invention, a variety of hydrophilic groups were introduced into the $R_4$ and $R_5$ positions of the chemical formula 6 compound to obtain a large amount of derivatives having enhanced binding ability to MCL-1 (FIG. 11 and FIG. 12).

In order to prove that the phenyl-piperazine-triazine compound can act as an alpha-helix mimetic for inhibiting inter-protein interaction, compound of Chemical formula 10 is selected as compound inhibiting interaction between BH3 protein and MCL-1 protein from the library constructed in the present invention. The compound of Chemical formula 10 is found to bind to MCL-1 and inhibit the interaction between MCL-1 and BH3 proteins, confirming that these compounds induce cancer cell apoptosis (FIG. 16 and FIG. 17).

Therefore, compounds of Chemical formula 4-6 and Chemical formula 9, 10 can be used as a preventive or therapeutic agent for cancer.

In another aspect, the present invention relates to a pharmaceutical composition for the prevention or treatment of Parkinson's disease, which comprises at least one compound or pharmaceutically acceptable salt selected from the group consisting of the following chemical formulae 7 and 8. In another embodiment, the present invention relates to a method for treating Parkinson's disease comprising administering to an individual an effective amount of at least one compound or pharmaceutically acceptable salt selected from the group consisting of compounds of Chemical Formulae 7 and 8;

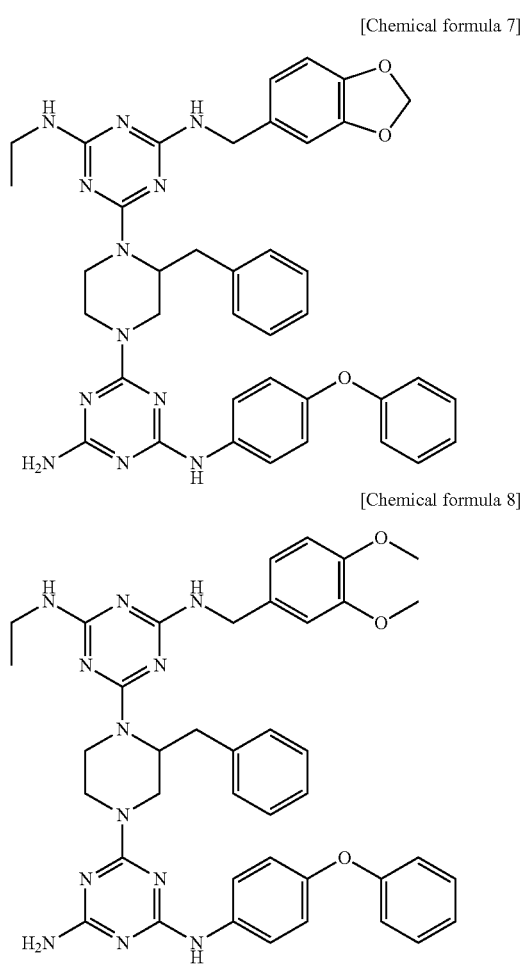

[Chemical formula 7]

[Chemical formula 8]

Aggregation of α-synuclein induces the formation of Lewy bodies, which are known as pathological features of Parkinson's disease. Therefore, in order to provide that the alpha-helix mimetic compounds in the present invention can inhibit the α-synuclein aggregation by stabilizing the folding structure of α-synuclein, the compounds that inhibit aggregation were selected from the chemical library constructed in the present invention. As a result, it was confirmed that the compound of chemical formula 7 to 8 binds to α-synuclein and inhibits the aggregation of α-synuclein (FIG. 13 and FIG. 14).

Therefore, compounds of chemical formulae 7 and 8 can be used as a preventive or therapeutic agent for Parkinson's disease.

The composition may further comprise suitable carriers, excipients and diluents conventionally used in the production of pharmaceutical compositions. The composition may be formulated into tablets, capsules, capsules, suspensions, emulsions, syrups, an external preparation, a suppository or a sterile injection solution, and the like.

When the composition is formulated, a diluent or excipient such as a filler, an extender, a binder, a wetting agent, a disintegrant, a surfactant or the like is usually used. Solid formulations for oral administration include tablets, pills, powders, granules, capsules, and the like, and such solid preparations may include at least one excipient and/or lubricant. Liquid preparations for oral administration include suspensions, solutions, emulsions and syrups. In addition to water and liquid paraffin which are commonly used diluents, various excipients such as wetting agents, sweeteners, fragrances, preservatives and the like may be included have. Formulations for parenteral administration may include sterile aqueous solutions, non-aqueous solvents, suspensions, emulsions, freeze-dried preparations, suppositories, and the like.

The preferred dosage of the composition varies depending on the condition and the weight of the patient, the degree of the disease, the drug form, the administration route and the period, but can be appropriately selected by those skilled in the art. For a more preferable effect, the dose of the composition of the present invention is preferably 0.1 mg/kg to 20 mg/kg per day based on the active ingredient, but is not limited thereto. The administration can be carried out once a day or divided into several times. The compositions of the present invention can be administered to a mammal, including a human, in various ways. All modes of administration may be expected, for example, by oral, intravenous, intramuscular, subcutaneous injection, and the like. The pharmaceutical dosage form of the composition of the present invention may be used in the form of a pharmaceutically acceptable salt of the active ingredient, and may be used alone or in combination with other pharmaceutically active compounds as well as in a suitable combination.

EXAMPLES

Hereinafter, the present invention will be described in detail with reference to examples. However, the following examples are illustrative of the present invention, and the present invention is not limited by the following examples.

Example 1. Preparation of Alpha-Helix Mimetic Compound Containing a Triazine-Piperazine-Triazine as a Core Structure 1-1. Preparation of Experimental Materials TentaGel B NH2/Boc resin (130 μm, 0.25 mmol/g) and TentaGel S NH2 resin (130 μm, 0.29 mmol/g) were purchased from Rapp Polymere. Rink amide MBHA resin (0.96 mmol/g) was purchased from Novabiochem. Liquid chromatograph-mass spectrometer (LC-MS) analysis was performed on a C18 reversed-phase column (Kinetex, 2 μm, 4.6 mm*50 mm) on an Agilent 1200 LC/MS system (Agilent Technology). LC-MS was performed by using solvent A at 90% gradient elution for 2 minutes and was by using solvent B at 100% gradient elution for 14 minutes, at flow rate of 0.8 mL/min(solvent A containing 95% water, 5% methanol, and 0.01% TFA; and solvent B containing methanol and 0.01% TFA). HPLC purification was performed using a C18 reverse phase column (Agilent Technology, 5 μm, 25 mm*125 mm) on an Agilent 1120 Compact LC system (Agilent Technology). A linear gradient was used from 10% B solvent to 100% B solvent while changing the solvent composition at every 40 minutes. MALDI-TOF MS was performed using an ABI 4800 and ABI 5800 mass spectrometer (Applied Biosystems) and α-cyano-4-hydroxy cinnamic acid was used as the substrate.

1-2. Preparation of Alpha-Helix Mimetic Compound Using Solid Phase Synthesis Method In order to synthesize a triazine-piperazine-triazine based compound, the solid phase synthesis method was developed as shown in FIG. 2. The desired compound was obtained in an average yield of 92% through five sequential coupling reactions by using amine (NH2) modified polymer beads.

By referring to FIG. 2, as a first step, single-substituted dichlorotriazine ("3") is loaded on a Rink-Amide MBHA resin and bound to the resin to produce a triazine derivative "4" bound to the resin. In a second step, a compound "6" was prepared by coupling a piperazine derivative ("5") protected with 2-nitrobenzene sulfonyl (Ns) to a triazine derivative ("4") attached to a resin. In the third step, the N-Ns protecting group is removed from the above coupled compound ("6"), followed by the addition of 2-ethyl amino-4,6-dichloro-[1,3,5]) Was introduced to produce compound "8". In the fourth step, various amine groups (R2"R2"NH) were substituted for the chloride sites of the compound ("8") prepared above. In a fifth step, Trifluoroacetic acid (TFA) Compound "9" functionalized with three substituents was prepared.

The preparation process will be described in more detail as follows.

Rink amide MBHA resin (100 mg, 69 μmol) was treated in DMF (2 mL) in a 5 mL fritted syringe for 1 hour and treated with 20% piperidine in DMF (2×10 min) to remove the Fmoc group. After washing with DMF (3×), MeOH (2×), $CH_2Cl_2$ (2×) and DMF (3×). To load the resin with mono-substituted dichlorotriazine on the resin, DMF (1 mL) was added and reacted with Et3N (5 equiv) overnight at room temperature. To coupling the piperazine derivative ("5")(10 equiv) protected with 2-nitrobenzene sulfonyl (Ns) to the resin, the product was incubated with $Et_3N$ (5 equiv) in DMF at 60° C. overnight. Unless otherwise described, the resin was thoroughly washed with DMF (3×), MeOH (2×), $CH_2Cl_2$ (2×) and DMF (3×) at the end of each reaction step. To remove the N-Ns protecting group from the coupled compound ("6"), the compound was reacted with 2-mercaptoethanol (20 equiv) and DBU (10 equiv) in DMF for 2 hours at room temperature. Then, to prepare compound "8" by introducing 2-ethylamino-4,6-dichloro-[1,3,5] Equiv), the bead was treated with compound 7 (5 equiv) and DIEA (5) in NMP and allowed to react overnight at 60° C. Finally, TFA (trifluoroacetic acid) was added to perform the cleavage reaction, to produced piperazine-triazine compound "9" functionalized with three substituents.

The purity and identification of the compounds prepared by the solid phase synthesis method was analyzed with LC-MS. As a result, the average purity of final product was 92% or higher, confirming the efficiency of the solid phase synthesis method. The compounds were purified with the reverse phase HPLC and identified with $^1$H-NMR, $^{13}$C-NMR and HRMS (high-resolution mass spectrometer).

TABLE 2

Mass and purity data of representative 40 final compounds

| Entry | $R_2$ | $R_3$ | $R_5$ | Calculated Mass (M) | Observed Mass (M + H) | Purity (%) |
|---|---|---|---|---|---|---|
| 1 | A | Benzyl | Ntyr | 632.3 | 633.2 | 94 |
| 2 | B | Benzyl | Ntyr | 694.4 | 695.2 | 94 |
| 3 | C | Benzyl | Ntyr | 674.4 | 675.2 | 95 |
| 4 | D | Benzyl | Ntyr | 736.4 | 737.0 | 95 |

TABLE 2-continued

Mass and purity data of representative 40 final compounds

| Entry | $R_2$ | $R_3$ | $R_5$ | Calculated Mass (M) | Observed Mass (M + H) | Purity (%) |
|---|---|---|---|---|---|---|
| 5 | A | Benzyl | Nnaph | 652.4 | 653.2 | 96 |
| 6 | B | Benzyl | Nnaph | 714.4 | 715.2 | 94 |
| 7 | C | Benzyl | Nnaph | 632.4 | 633.2 | 95 |
| 8 | D | Benzyl | Nnaph | 756.4 | 757.2 | 95 |
| 9 | A | Benzyl | Ndcp | 684.3 | 685.0 | 92 |
| 10 | B | Benzyl | Ndcp | 746.3 | 747.0 | 96 |
| 11 | C | Benzyl | Ndcp | 726.3 | 727.0 | 95 |
| 12 | D | Benzyl | Ndcp | 788.3 | 789.0 | 92 |
| 13 | A | Benzyl | Ndpe | 692.4 | 693.2 | 95 |
| 14 | B | Benzyl | Ndpe | 754.4 | 755.2 | 93 |
| 15 | C | Benzyl | Ndpe | 734.4 | 735.2 | 96 |
| 16 | D | Benzyl | Ndpe | 796.4 | 797.2 | 95 |
| 17 | A | Benzyl | Npip | 646.3 | 647.0 | 93 |
| 18 | B | Benzyl | Npip | 708.3 | 709.0 | 95 |
| 19 | C | Benzyl | Npip | 688.4 | 689.2 | 95 |
| 20 | D | Benzyl | Npip | 750.4 | 751.2 | 96 |
| 21 | A | Isobutyl | Ntyr | 598.4 | 599.2 | 98 |
| 22 | B | Isobutyl | Ntyr | 660.4 | 661.2 | 97 |
| 23 | C | Isobutyl | Ntyr | 640.4 | 641.2 | 97 |
| 24 | D | Isobutyl | Ntyr | 702.4 | 703.2 | 98 |
| 25 | A | Isobutyl | Nnaph | 618.4 | 619.2 | 94 |
| 26 | B | Isobutyl | Nnaph | 680.4 | 681.2 | 97 |
| 27 | C | Isobutyl | Nnaph | 660.4 | 661.2 | 96 |
| 28 | D | Isobutyl | Nnaph | 722.4 | 723.2 | 95 |
| 29 | A | Isobutyl | Ndcp | 650.3 | 651.0 | 94 |
| 30 | B | Isobutyl | Ndcp | 712.3 | 713.0 | 97 |
| 31 | C | Isobutyl | Ndcp | 692.3 | 693.0 | 96 |
| 32 | D | Isobutyl | Ndcp | 754.4 | 755.2 | 96 |
| 33 | A | Isobutyl | Ndpe | 658.4 | 659.2 | 96 |
| 34 | B | Isobutyl | Ndpe | 720.4 | 721.2 | 97 |
| 35 | C | Isobutyl | Ndpe | 700.4 | 701.2 | 96 |
| 36 | D | Isobutyl | Ndpe | 762.5 | 763.2 | 95 |
| 37 | A | Isobutyl | Npip | 612.3 | 613.0 | 93 |
| 38 | B | Isobutyl | Npip | 674.4 | 675.2 | 95 |
| 39 | C | Isobutyl | Npip | 654.4 | 655.2 | 96 |
| 40 | D | Isobutyl | Npip | 716.4 | 717.2 | 95 |
| Average purity | | | | | | 92.2% |

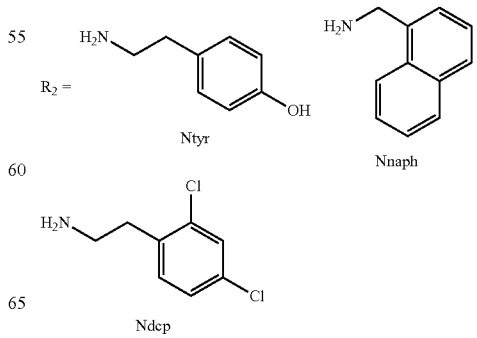

TABLE 2-continued

Mass and purity data of representative 40 final compounds

| Entry | $R_2$ | $R_3$ | $R_5$ | Calculated Mass (M) | Observed Mass (M + H) | Purity (%) |
|---|---|---|---|---|---|---|

$R_3 =$ Benzyl, Isobutyl $R_5 =$ A, B, C, D

Example 2. Construction of Chemical Library Containing Alpha-Helix Mimetic with Triazine-Piperazine-Triazine as Core Structure In the present invention, an alpha-helix mimetic chemical library containing triazine-piperazine-triazine as a core structure was constructed using a polymer bead modified with amine ($NH_2$), and was named as OBOC (one-bead one-compound) library. The preparation procedure is shown in FIG. 3.

As shown in FIG. 3, this example using a bifuncational bead where the surface (exterior) side of bead is bound by amine group protected with BOC (tert-butyloxycarbonyl) group and the interior side of bead is bound by free amine. On the surface of the beads, alpha-helix mimetic was synthesized according to the solid-phase synthesis method described in Example 1, and peptoid residues corresponding to each substituent was connected to the interior side of bead at every time of introducing a substituent into the alpha-helix mimetic, to finally obtain two kinds of compounds connected to one bead. In other words, an alpha-helix mimetic is on the bead surface and a peptoid specific to the alpha-helix mimetic is on the inside of the bead. This peptoid serves as a coding tag that allows the structure of the alpha-helix mimetic bound to the bead surface. In some cases, substituents of the peptoids corresponding to the respective substituents of the alpha-helix mimetic may be the same. However, when the substituent of the alpha-helix mimetic is a secondary amine or piperazine, the substituent of peptoid may be different from that of the alpha-helix mimetic. Thus, in the present invention, various combinations of alpha-helix mimetic were prepared by tagging 18 species at $R_5$ substituents, 3 species at $R_3$ substituents, and 27 species at $R_2$ substituents with the peptoids, respectively. As a result, the chemical library including a total of 1,458 species (=18×3×27) could be constructed.

TABLE 3

Structure of substituent coupled with peptoid tag for library synthesis.

Building block I and amines ($R_5'''NH_2$) for coding peptoids $R_5'R_5''NH$ ($R_5'''NH_2$)

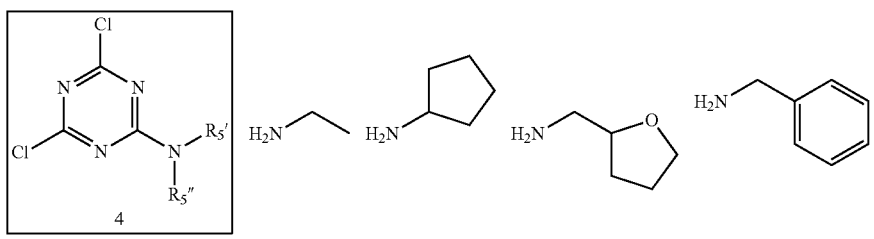

TABLE 3-continued
Structure of substituent coupled with peptoid tag for library synthesis.
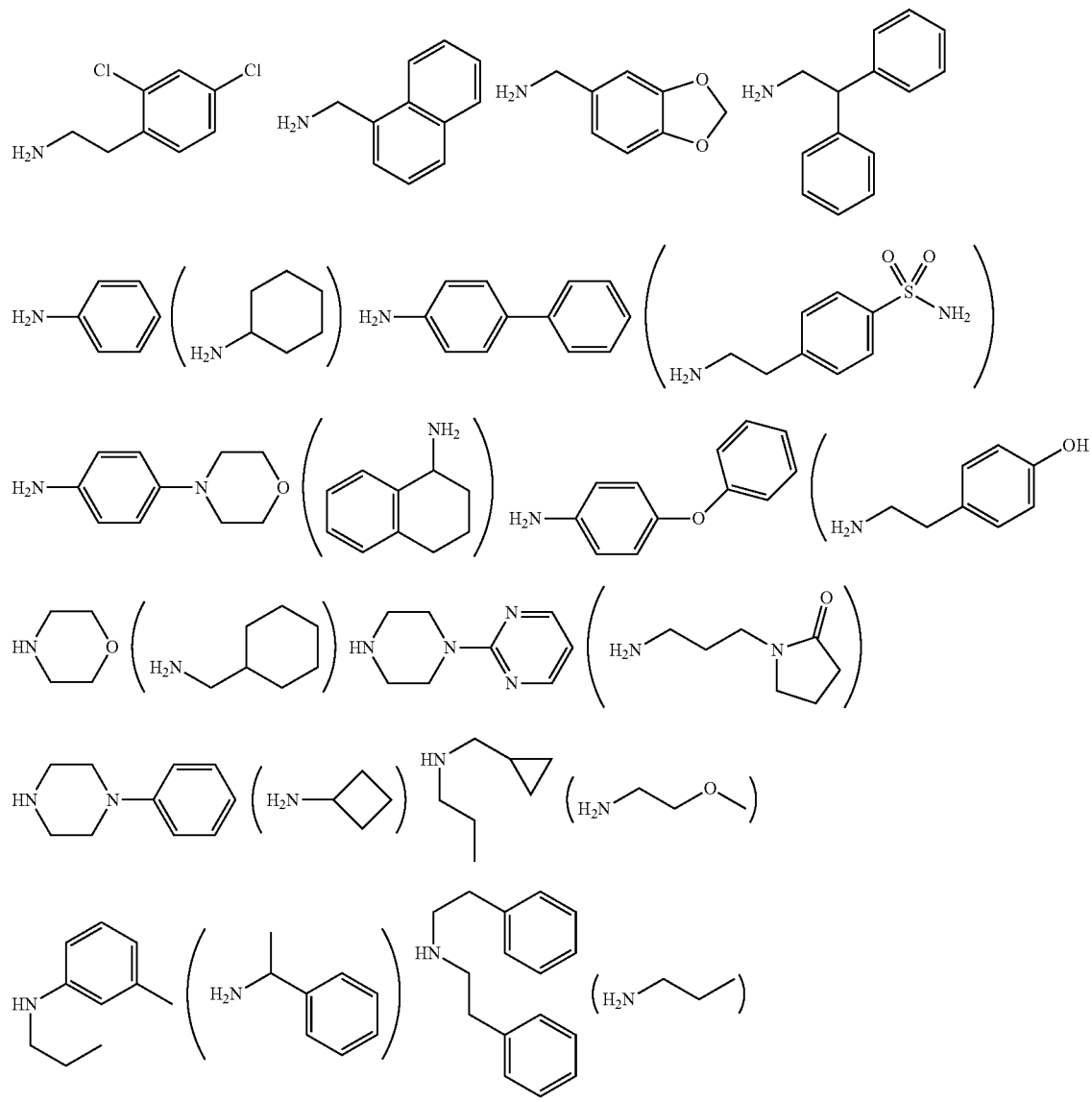
Building block II and amines used for coding peptoids ($R_3''NH_2$)
$R_3$ ($R_3''NH_2$)
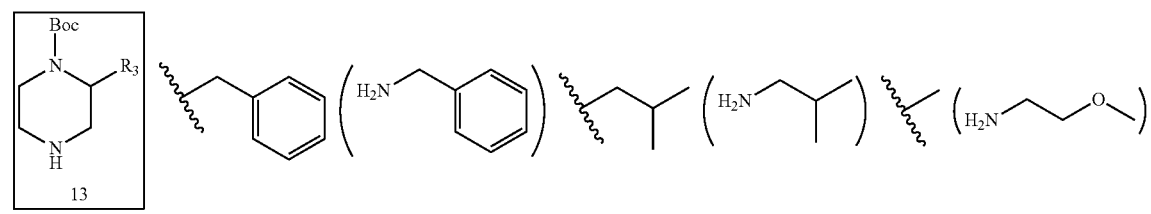
Building block III and amines used for coding peptoids ($R_2'''NH$)
$R_2'R_2''NH$
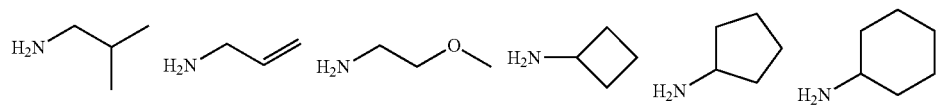

TABLE 3-continued

Structure of substituent coupled with peptoid tag for library synthesis.

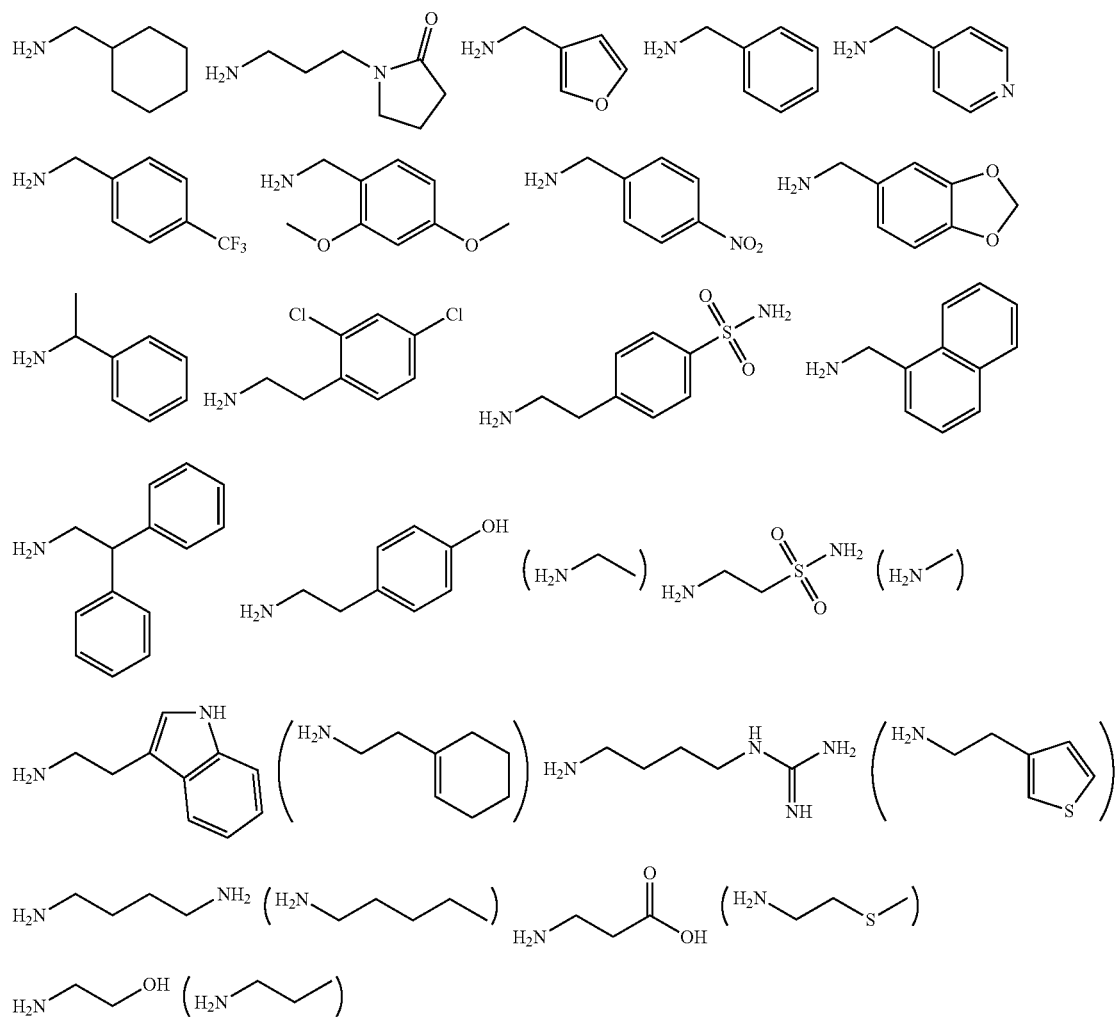

The structure in parentheses indicates the amines used for the coding peptoid synthesis when the substituents are not the same.

The constructed chemical library of alpha-helix mimetic can be used for high-efficiency screening on bead. The process is shown in FIG. 4.

As shown in FIG. 4, the alpha-helix on bead surface is exposed to the target protein in the bead screening, but the peptoid inside the bead is not exposed. After screening, the structure of the alpha-helix mimetic on the bead surface can be analyzed by sequencing peptoids inside the bead.

The manufacturing process will be described in more detail as follows.

TentaGel B $NH_2$/Boc resin (250 mg, $NH_2$: 62.5 µmol/ Boc: 1.3 µmol) was treated with DMF (2 mL) for 2 hours. The beads were treated with Fmoc-L-methionine (Fmoc-Met-OH) (5 equiv) in the presence of HOBt (5 equiv), HBTU (5 equiv) and DIEA (10 equiv) in DMF (1 mL). After stirring for 2 h, the reaction mixture was removed and washed with DMF (3×), MeOH (2×), $CH_2Cl_2$ (2×) and DMF (3×). Next, Fmoc-4-aminobutyric acid (Abu) (5 equiv) was added using the same peptoid coupling conditions. The above procedure was repeated twice to couple three Abu linker residues. After Fmoc deprotection, the resulting amine was bromoacetylated by treatment with 1 M bromoacetic acid and 1 M DIC in DMF (2 mL) at room temperature. To protect the N-terminus of the peptoids with allyloxycarbonyl (Alloc) group, allylchloroformate (5 equiv) and $Et_3N$ (6 equiv) in anhydrous $CH_2Cl_2$ were treated and reacted overnight at 4° C. To remove the Boc group on the bead surface, 50% TFA in $CH_2Cl_2$ was added and reacted for 1 hour. The resulting primary amine was coupled with 18 other mono-substituted triazine derivatives ("4") (5 equiv). After washing thoroughly with DMF (3×), MeOH (2×), $CH_2Cl_2$ (2×). and NMP (3×), all beads were randomized into 250 mL vessels and divided into 3 vessels. Boc protected piperazine (10 equiv) and NMP (1 mL) in DIEA (10 equiv) were treated and reacted overnight at 60° C. to replace the chloride position of triazine with three different piperazines. After washing with DMF (3×), MeOH (2×), $CH_2Cl_2$ (2×), $Pd(PPh_3)_4$ (0.2 equiv) and $PhSiH_3$ (10 equiv) in anhydrous $CH_2Cl_2$ (1 mL) were treated to remove Alloc group. The second peptoid residue (R2″) was coupled by using sub-monomer route. The beads were mixed again and randomized. After bromoacetylation, the beads were divided into 27 vessels and reacted with 27 different amines. The N-terminus of the peptoid was blocked by bromoacetylation and subsequent reaction with piperidine. Next, 50% TFA in $CH_2Cl_2$ was treated and reacted for 1 hour to remove the Boc group. After neutralization with 10% DIEA in DMF, DIEA in NMP and 4,6-dichloro-1,3,5-triazin-2-ethylamine were added to the beads and reacted overnight at 60° C. After washing with DMF (3×), MeOH (2×), and CH$_2$Cl$_2$ (2×), all beads were mixed and subjected to global deprotection by treatment with 95% TFA. For cleavage, 20 μL CNBr (40 mg/mL) in ACN/AcOH/H$_2$O (5:4:1) was treated for each bead and reacted at room temperature for 12 hours.

To verify the efficiency of the library synthesis, 30 beads were selected randomly from the library. After the cleavage reaction with CNBr, the resultant peptoid was analyzed by MS. The alpha-helix-like molecules on the bead surface were not cleaved but only peptoids attached to the beads through methionine were released by CNBr treatment. No significant impurity peaks were observed in all tested beads, confirming a high purification rate and the efficiency of library synthesis.

Example 3. Selection and Activity Test of Alpha-Helix Mimetic Compound Inhibiting Interaction Between BH3 (BCL-2 Homology Domain 3) Protein and MCL-1 (Myeloid Cell Leukemia-1) Protein 3-1. Compound Selection In the present invention, in order to demonstrate that the triazine-piperazine-triazine compound can act as an alpha-helix mimetic inhibiting inter-protein interaction, the compounds are selected to have an inhibitory activity on the interaction between BH3 protein and MCL-1 protein from the library constructed in Example 2.

MCL-1 (myeloid cell leukemia-1) is one of BCL-2 (B-cell lymphoma 2) family proteins with anti-apoptotic activity, and inhibits the cell apoptosis caused by BH3 and help the cell survival by interacting with BH3 (BCL-2 homology domain 3) family proteins such as BAK. Therefore, the inhibition of interaction between MCL-1 protein and BH3 proteins in cancer cells can prevent the cancer cell survival, thereby being a promising strategy for anti-cancer therapy.

To select the alpha-helix mimetic compounds inhibiting MCL-1/BH3 protein interaction, the present inventors constructed chemical library on polymer bead according to the same method of Example 2, and the compound directly binding to MCL-1 protein was selected by using on-bead screening method as shown in FIG. 4. First, 25 mg (~0,200 beads, ~copies of diversity) of the library containing the compounds bound to bead 25 mg (~0,200 beads, ~copies of diversity) were incubated with 200 nM of biotinylated MCL-1ΔNΔC (biotinylated MCL-1) overnight at 4° C. The unbound proteins were washed and treated with Dynabeads (iron oxide particles) coupled with streptavidine, to separate the positive bead using magnetic separation. Several hundreds of beads were selected in the first screening step. Beads conjugated with streptavidin (potentially false positives) were removed before screening with MCL-1. The selected beads were heated at 1% SDS to remove bound proteins. After washing, the beads were again incubated with 100 nM of biotinylated MCL-1ΔNΔC for 4 hours at 4° C. and labeled with streptavidin-conjugated alkaline phosphatase. In order to select optimal compounds, secondary screening was performed under stringent conditions (i.e., smaller amounts of protein and shorter incubation time). Next, the bead was treated with 5-bromo-4-chloro-3-indolyl phosphate for colorimetric detection of alkaline phosphatase. Ten blue beads were separated as candidate compounds. The peptoids derived from each bead were analyzed with MS/MS analysis. As a result, 10 beads contained the same peptoid sequence and the peptoides could be largely divided into three kinds of peptoid groups. 5 beads contained peptido-1, 3 beads contained peptoid-2, and 2 beads contained peptoid-3.

TABLE 4

| Entry | Peptoid sequence | Number of hit beads | Structure of hit compounds |
|---|---|---|---|
| 1 | Peptoid-1 | 5 | 9a (Chemical formula 4) |
| 2 | Peptoid-2 | 3 | 9b (Chemical formula 5) |

TABLE 4-continued

| Entry | Peptoid sequence | Number of hit beads | Structure of hit compounds |
|---|---|---|---|
| 3 | Peptoid-3 | 2 | 9c (Chemical formula 6) |

This result is considered to be due to the inclusion of about 7 copies of each compound in the library, indicating that the screening system developed in the present invention works well. As a result of analyzing the three peptoids, the selected compounds had the following structures of 9a (Chemical formula 4), 9b (Chemical formula 5) and 9c (Chemical formula 6), respectively. These compounds were separated by HPLC and were found to be water soluble (These compounds were dissolved as ~100 µg/mL in phosphate buffered saline at pH 7.4, indicating a range of water solubility to be used as oral absorption in usage of drug).

[Chemical formula 4]

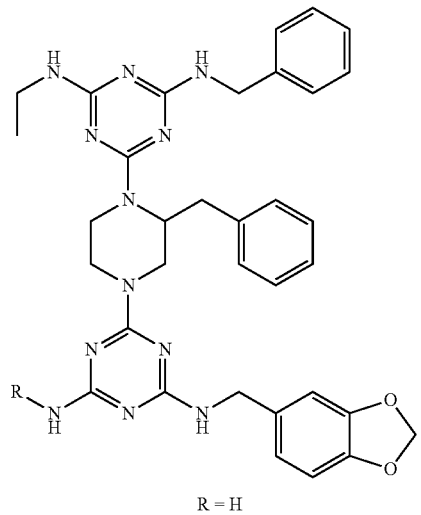

R = H

-continued

[Chemical formula 5]

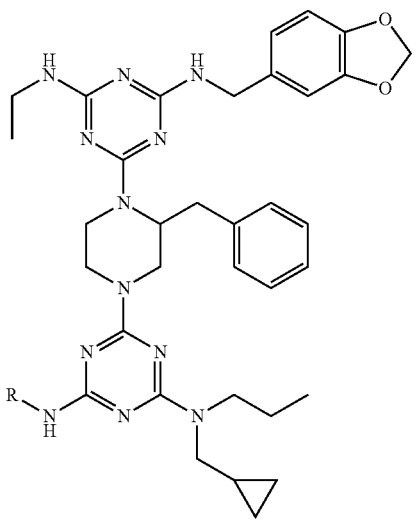

R = H

[Chemical formula 6]

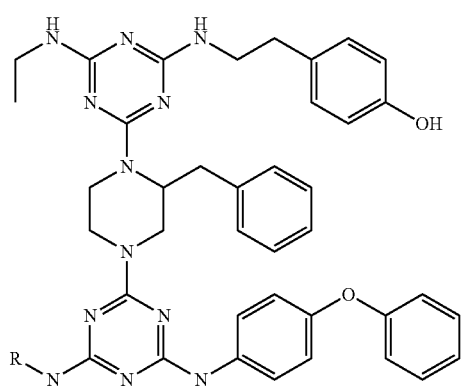

R = H

3-2. Synthesis of Fluorescence Labeled Compound

The procedure for fluorescence labeling the compound of Chemical Formulae 4 to 6 is shown in FIG. 5, and the fluorescence-labeled compounds are shown as 9a-FL, 9b-FL and 9c-FL, respectively.

First, TentaGel S NH2 resin (100 mg, 29 μmol) was treated with DMF (2 mL) for 1 hour. The beads were treated with Fmoc-L-methionine (Fmoc-Met-OH) (5 equiv) in the presence of HOBt (5 equiv), HBTU (5 equiv) and DIEA (10 equiv) in DMF (1 mL) and reacted at room temperature. After stirring for 2 hours, the reaction mixture was obtained and washed. In order to remove Fmoc protecting group, the obtain product was treated with 20% piperidine in DMF (1 mL, 2×10 min). Next, Fmoc-Lys (Alloc)-OH and Fmoc-Abu-OH were coupled under the same peptide coupling conditions. After Fmoc deprotection, the obtained product was reacted with the treatment of DIEA (5 equiv) and monosubstituted dichlorotriazine in DMF overnight at room temperature. The reaction mixture was obtained and washed with DMF (3×), MeOH (2×), $CH_2Cl_2$ (2×) and NMP (3×). Boc protected piperazine derivative (10 equiv) and DIEA (10 equiv) were added to the beads in NMP (1 mL). The mixture was stirred at 60° C. overnight. After washing, 50% TFA in $CH_2Cl_2$ was treated for 1 hour to remove the Boc group. The resin was neutralized with 10% DIEA in DMF (1 mL) for 1 hour and then washed with DMF (3×), MeOH (2×), $CH_2Cl_2$ (2×) and NMP (3×). Then, DIEA (5 equiv) and 4,6-dichloro-1,3,5-triazin-2-ethylamine in NMP were added to the beads, reacted at 60° C. overnight and washed with DMF (3×), MeOH (2×) and NMP (3×). The resin was then treated with DIEA (20 equiv) and amine (20 equiv) in NMP, reacted at 60° C. overnight, and washed with DMF (3×), MeOH (2×), and $CH_2Cl_2$ (2×). After deprotecting Alloc by treating $Pd(PPh_3)_4$ (0.2 equiv) and $PhSiH_3$ (10 equiv) in anhydrous $CH_2Cl_2$ (1 mL) for 1 hour, $NH_2$ of the produced Lysine residue was coupled with 5,6-carboxyfluorescein (5 equiv) by using peptide coupling condition. For cleavage, the beads were treated with 20 μL CNBr (40 mg/mL) in $ACN/AcOH/H_2O$ (5:4:1) and reacted at room temperature for 12 hours. The cleavage crude product was purified by HPLC.

3-3. Computer-Assisted Molecular Docking Studies

The structure of compound was constructed using Maestro (Maestro v9.0, Schrdinger, LLC, Portland, Oreg.), and the lowest energy was achieved by using CHARMM General Force Field (Vanommeslaeghe, K; Hatcher, E.; Acharya, C.; Kundu, S.; Zhong, S.; Shim, J.; Darian, E.; Guvench, O.; Lopes, P.; Vorobyov, I.; Mackerell, A. D. J. Comput. Chem. 2010, 31, 671). The structures of ligand and receptor for docking were analyzed by using Raccoon (Forli, S. Raccoon utodock VS: an automated tool for preparing AutoDock virtual screenings). The docking box center was organized with geometric center in BH3 helix residues and the X, Y and Z of box size were set to 25. To produced pose decoy in MCL-1 crystalline structure (PDB entry: 3MK8), the independent 20 AutoDock Vina (Trott, O.; Olson, A. J. J. Comput. Chem. 2010, 31, 455) docking to each compound was performed. 400 pose decoy was obtained for each compound, and the final model was determined as best scoring pose. The molecular structure of compound was visualized with Software PyMol.

3-4. Protein Purification

The expression vector encoding BH3-binding domain (172-320th amino acids) in human MCL-1ΔNΔC protein was tagged with GST, and introduced into BL21(DE3) *E. coli* cell. The cell was treated with 1 mM IPTG (isopropyl β-D-1-thiogalactopyranoside) to induce the protein expression. The cell pellet was resuspended with lysis buffer (20 mM Tris, pH 7.2, 250 mM NaCl, complete protease tablet (Roche)) and sonicated to be lysis. After centrifuging, the cell lysate was applied to a 5-mL GSTrap HP column (GE Life Sciences) and performed according to the manufacturer's instructions. The MCL-1 protein was obtained by cleavage with thrombin protease, reloaded on the GSTrap HP column and performed by size exclusion chromatography to remove GST. MCL-1 protein was incubated with sulfo-NHS-Biotin (Thermo Scientific) in 0.1 M NaHCO3 buffer (pH 8.3) for 45 minutes at room temperature to biotinylate the MCL-1 protein (because MCL-1ΔNΔC protein used in the test have several Lysine residues being exposed in a surface and being apart from the active site of BH3 binding, the protein is biotinylated with modification). The reaction was quenched with addition of 1.5 M hydroxylamine. The labeled protein was separated with the dialysis with 1×PBS buffer containing 0.05% Tween20 (pH 7.4). The degree of labeling was determined according to the manufacturer's instructions (degree of biotinylation: 1.05 biotin per protein).

3-5. Fluorescence Polarization Assay

The fluorescence-labeled compound (50 nM) was incubated with MCL-1ΔNΔC or BCL-1 using a binding buffer (50 mM Tris, 100 mM NaCl, pH 8.0) adjusted to a final concentration of 60 μL in a black Costar 384-well plate at dark for 30 minutes at room temperature. Fluorescence polarization values were measured with a SpectraMax M5 Multi-Mode Microplate Reader (Molecular Devices). Excitation wavelength was adjusted to 485 nm and the emission was measured at 535 nm. $K_D$ was calculated with GraphPad Prism 4 software. In order to perform the competitive fluorescence polarization assay, MCL-1ΔNΔC was replaced with FITC-labeled MCL-1 BH3 peptide (FITC-MCL-1-BH3 peptide). N-terminal labeled FITC-MCL-1-BH3 peptide (FITC-Abu-KALETLRRVGDGVQRNHETAF-NH2) was synthesized and purified with HPLC. The compounds was incubated at various concentrations with FITC-MCL-1-BH3 (50 nM) and 0.8 μM MCL-1ΔNΔC in binding buffer for 30 minutes and then was added by FITC-MCL-1-BH3 (50 nM). After incubated with addition of various concentrations of compounds, the fluorescence polarization was measured. Ki was calculated by using the conventional method (Nikolovska-Coleska, Z. et al, Anal. Biochem. 2004, 332, 261).

3-6. Cell Viability Assay

Jurkat T cells were cultured in RPMI 1640 medium containing 10% FBS, and 4×10⁴ Jurkat T cells were seeded in 100 μL Opti-MEM medium (Invitrogen) of 96-well plate. WS-1 cells were cultured in MEM medium containing 10% FBS and 2×10⁴ WS-1 cells were seeded in 100 μL MEM medium containing 10% FBS of 96-well plate for 24 hours, washed with PBS, and cultured in 100 μL Opti-MEM. The cells were maintained at serum-starved state for 6 hours and treated with the compound. After culturing for 24 hours, the cell viability was assayed using the CellTiter 96 AQueous Non-Radioactive Cell Proliferation Assay kit (Promega) according to the manufacturer's instructions.

3-7. Caspase Assays

Jurkat T cells were plated at 2×10⁴ cells/well in Opti-MEM medium of white-walled 96-well plates and treated with various concentrations of compound or DMSO for 16 hour. WS-1 cells were plated on white-walled 96-well plates at 1×10 4 cells/well and cultured in MEM medium containing 10% FBS for 24 hours. Cells were washed with PBS and treated with compounds in Opti-MEM medium like Jurkat T cells. Caspase 3/7 activity was measured using the Caspase-Glo 3/7 Assay kit (Promega) according to the manufacturer's instructions.

3-8. Confocal Microscopy Experiment

A549 cells ($5\times10^3$ cells) were plated MEM medium containing 10% FBS of 96-well plates. Cells were maintained for 24 hours, washed with PBS, and then 1 μL of fluorescence-labeled compound or 5 (6)-carboxyfluorescein was treated in Opti-MEM medium and incubated for 2.5 hours. The cells were washed with 1×PBS (2 times) and fluorescence images were analyzed.

3-9. Co-Immunoprecipitation Assay

In Opti-MEM medium, Jurkat T cells (1×107 cells) were treated with DMSO or compound. Cells were harvested after culturing for 2.5 hours, washed once with PBS, and lysed on ice using lysis buffer (50 mM Tris-HCl, pH 7.4, 150 mM NaCl, 1 mM EDTA, 1 mM DTT, 0.5% NP-40 and complete protease inhibitor tablet). Cell lysates were incubated with anti-MCL-1 antibody (S-19, Santa Cruz) overnight at 4° C. and incubated with protein A/G agarose for 1 hour. The beads were precipitated, washed at three times with lysis buffer, and the denatured protein was subjected to western blotting using anti-BAK (Cell Signaling) and anti-MCL-1 antibody. Western blot analysis was performed on an Immobilon-FL (Millipore) PVDF membrane. Goat anti-Rabbit IRDye 680 antibody (Licor) was used as a secondary antibody and the signal was analyzed with Odyssey 3.0 software.

3-10. Experimental Result

As a result of measuring the binding affinity of MCL-1 protein to selected three compounds by fluorescence polarization assay of compounds, the KD value of compound of chemical formulae 4 to 6 bound to MCL-1 were 2.8, 3.0, and 1.1 μM, respectively, confirming that all three compounds effectively bind to MCL-1 protein. The KD value of the known BH3 peptide used as a positive control was 0.3 μM. Fluorine-linkers used as negative controls did not bind to MCL-1, indicating that the fluorophore and linker bound to each compound did not affect binding to MCL-1 (FIG. 6B). In addition, the competitive fluorescence polarization assay was performed in order to that these compounds actually interfere with the interaction between MCL-1 and BH3 proteins. As a result, the dissociation Ki values of the compounds of Chemical formulae 5 and 6 dissociated the interaction between MCL-1 and BH-3 were measured as 17.2 and 9.3 μM, respectively, and the chemical formula 4 compound showed weak activity. The compound 9-nc used as a negative control did not bind to MCL-1 (FIG. 6C). Next, a computer-based docking model study predicted that the compound of Chemical formula 6 would bind well to the BH3 binding site of MCL-1 (FIG. 7B).

BH3 becomes free and causes cancer cell apoptosis. Therefore, it was investigated whether the selected compounds induce the death of cancer cells by inhibiting protein interaction between MCL-1 and BH3 in combination with MCL-1.

First, in order to confirm that the compound of chemical formula 5 inhibits MCL-1/BH3 protein interaction in cells, Jurkat leukemia T cells (cancer cells) are treated with the compound of Chemical formula 6. The cell lysate was immunoprecipitated with the treatment of anti-MCL-1 antibody and then, the western blots were performed using anti-BAK and anti-MCL-1 antibodies, confirming that the compound of chemical formula 5 was found to effectively inhibit MCL-1 and BAK (one of BH3 protein) (FIG. 8A). However, the negative control compound 9nc did not inhibit protein interaction between MCL-1 and BAK (FIG. 9). In addition, the compound of Chemical formula 6 was found to permeate into cells and to competitively bind to MCL-1 and release BAK protein. Confocal microscopy analysis indicates that the compound is permeable to cells (FIG. 8B). The compound of chemical formula 6 effectively inhibited the survival of cancer cells of Jurkat leukemia T cells and multiple myeloma cells, U266 cells, but did not affect survival of the normal cells of WS-1 human fibroblast cells and HEK293 embryonic kidney cells. Therefore, it was confirmed that the compound of chemical formula 6 had a selective effect on cancer cells (FIG. 8C and FIG. 10B, C).

As a result of the caspase 3/7 assay for confirming the cancer cell death caused by cell apoptosis of compound of chemical formula 6, the compound of chemical formula 6 increased the caspase activity in a concentration-dependent manner in U266 cells, but not in WS-1 cells (FIG. 10C).

As a result, the compounds of chemical formulae 4 to 6 inhibited the interaction between BH3 protein and MCL-1 protein. Among them, the compound of chemical formula 6 showed cytotoxicity selectively in cancer cells. Therefore, these compounds are highly promising as anticancer drugs in the future. In addition, it was confirmed that the compounds of triazine-piperazine-triazine scaffold developed in the present invention function as an alpha-helix mimetic and can effectively inhibit protein-protein interactions.

Example 4. Preparing the Derivative with Improved Hydrophilicity of Alpha-Helix Mimetic Compound Including Triazine-Piperazine-Triazine as Core Structure In the compound of Chemical Formula 6, which showed excellent inhibitory effect on the interaction between BH3 protein and MCL-1 protein, Et at R1 position and H at R4 were replaced with various hydrophilic functional groups, to develop the derivatives with higher binding affinity than the compound of Chemical formula 6 to MCL-1.

In the compound of Chemical formula 6, Et at $R_1$ position was replaced with various hydrophilic functional groups to obtain 10 derivatives called as MO-01 to MO-10, and the preparation procedure was shown in FIG. 11.

In the compound of Chemical formula 6, H at $R_4$ position was replaced with various hydrophilic functional groups to obtain 10 derivatives called as MO-11 to MO-20, and the preparation procedure was shown in FIG. 12.

The prepared derivatives of MO-01 to MO-20 are shown in the following:

TABLE 5

| compound | R₁ | R₄ |
|---|---|---|
| MO-01 | –(CH₂)₄–NH₂ | H |
| MO-02 | –(CH₂)₃–NH₂ | H |
| MO-03 | –(CH₂)₂–NH₂ | H |
| MO-04 | –(CH₂)₄–NH–C(=O)–NH₂ | H |
| MO-05 | –(CH₂)₃–NH–C(=NH)–NH₂ | H |
| MO-06 | –(CH₂)₂–NH–C(=NH)–NH₂ | H |
| MO-07 | –(CH₂)₄–COOH | H |
| MO-08 | –(CH₂)₃–COOH | H |
| MO-09 | –(CH₂)₂–COOH | H |
| MO-10 | –(CH₂)₃–OH | H |
| MO-11 | Et | –(CH₂)₄–NH₂ |
| MO-12 | Et | –(CH₂)₃–NH₂ |
| MO-13 | Et | –(CH₂)₂–NH₂ |
| MO-14 | Et | –(CH₂)₄–NH–C(=NH)–NH₂ |
| MO-15 | Et | –(CH₂)₃–NH–C(=NH)–NH₂ |
| MO-16 | Et | –(CH₂)₂–NH–C(=NH)–NH₂ |
| MO-17 | Et | –(CH₂)₄–COOH |
| MO-18 | Et | –(CH₂)₃–COOH |
| MO-19 | Et | –(CH₂)₂–COOH |
| MO-20 | Et | –(CH₂)₃–OH |

Example 5. Selection and Efficacy Test for Alpha-Helix Mimetic Compound Having an Inhibitory Effect on the α-Synuclein Aggregation

5-1. Compound Selection

In order to prove that the compounds containing triazine-piperazine-triazine can stabilize the protein folding and inhibit the protein aggregation, α-synuclein was used as a representative disease factor related with the protein folding. Aggregation of α-synuclein induces the formation of Lewy bodies, which are known as pathological features of Parkinson's disease. Although the mechanism of formation of Lewy bodies is not clear yet, it is believed that the misfolding of α-synuclein and its improper self-association are involved in the formation of Lewy bodies. It is also known that about 65% of α-synuclein is composed of alpha-helix. Therefore, it has been experimentally examined whether the alpha-helix mimetic compounds developed in the present invention can stabilize the folding structure of α-synuclein and inhibit α-synuclein aggregation.

For the purpose of the experiment, the constructs were made by introducing MKCK quad-peptide (i.e., a peptide composed of methionine-lysine-cysteine-lysine) at the N-terminus of α-synuclein and the reacting Cysteine being capable of chemically cross-linking to fluorophore and bead (The wild type alpha-synuclein does not contain cysteine). After α-synuclein containing cysteine (cys-Syn) was biotinylated, the compounds was screened according to the method described in Example 3-1. As a result, the compounds of Chemical formula 7 (Q1) and Chemical formula 8 (Q2) were selected.

[Chemical formula 7]

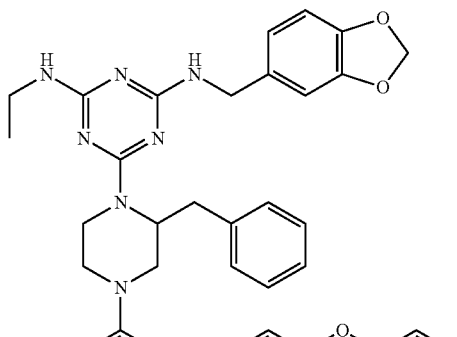

[Chemical formula 8]

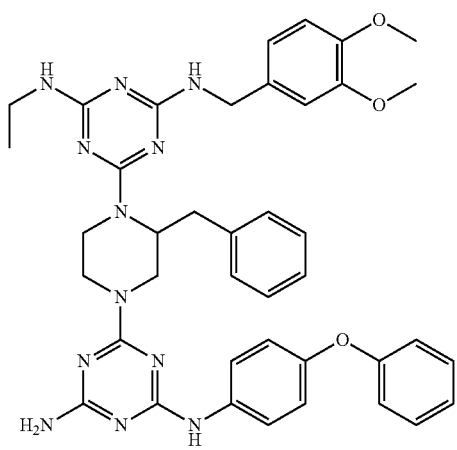

5-2. Protein Purification

From the pRS vector, the open reading frame of N-terminal extension MKCK quad-peptide and the construct of α-synuclein were amplified. A reverse primer (5"-GCCTTT-GAAAGTCCTTTGCAGAATACACACTTCCCGGGAAT-TCC-3") containing XhoI restriction site and forward primer (5"-GGAATTCCCGGGAATGTGTGTATTCTG-CAAAGGACTTTCAAAGGC-3") containing the SamI restriction site were used. The amplified DNA was cloned into pGEX-6P-1 plasmid (GE Biosciences) to produce a GST fusion construct. Expression plasmids were introduced into rossetta 2 (DE3) *E. coli* cells and protein expression was induced by treatment with 1 mM IPTG at 20° C. The cell pellet was resuspended in lysis buffer (100 mM HEPES, pH=7.4, 150 mM NaCl, 10% glycerol, 0.1% BOG, Halt Protease Inhibitor cocktail (Thermo Scientific)) and sonicated to lysis. After centrifugation, the cell lysate was applied to a 20-mL GSTPrep HP column (GE Life Sciences) and performed according to the manufacturer's instructions. The alpha-synuclein protein was obtained by cleavage reaction with PreScission protease (GE healthcare life sciences) overnight. After buffer change, the GSTPrep column was loaded again and size exclusion chromatography was performed to remove GST.

In order to biotinylate α-synuclein protein. α-synuclein protein was incubated with sulfo-NHS-Biotin (Thermo Scientific) in 0.1 M $NaHCO_3$ buffer (pH 8.3) at room temperature for 45 minutes. The reaction was quenched with addition of 1.5 M hydroxylamine. The labeled protein was separated with dialysis using 1×PBS buffer containing 0.05% Tween20 (pH 7.4) and the labeling degree was determined according to the manufacturer's instructions (degree of biotinylation: 1.07 biotin per protein).

5-3. Thioflavin-T Aggregation Assay

Each compound and 2-10 uL DMSO (as blank) was treated with 100 uL of 0.2 mM a-synuclein disease-associated mutant A53T cells and incubated with buffer (100 mM HEPES, pH 7.4, 150 mM NaCl, 10% glycerol, 0.1% BOG And 5 uM Thioflavin-T) to give a final concentration of 100 μM and incubated at 37° C. with frequent agitation. The thioflavin-T fluorescence (excitation wavelength 440 nm, emission wavelength 485 nm, cutoff wave-length 475 nm) was measured at intervals of 1 hour at 37° C. using FlexStation 2 (Molecular Devices, Sunnyvale, Calif., USA) for total time of 30 hours.

5-4. Circular Dichroism (CD) Thermal Denaturation Assay

In the presence or absence of the compound, the thermal denaturation of α-synuclein was monitored with a 222-nm CD signal on a BioLogic MOS-450 spectrophotometer equipped with a Peltier temperature controller using a 1-cm pathlength quartz cuvette. DMSO solution and the compound were added to protein samples (0.05 mg/mL, 100 mL HEPES, 150 mM NaCl, 10% glycerol, 0.1% BOG, 1% taurodeoxycholic acid) to give a final concentration of 1 uM of 1% DMSO at 25° C. to 60° C. and 1° C./min.

5-5. Experimental Result

In order to determine if the selected compounds of Chemical formulae 7 and 8 bind to α-synuclein, the $K_D$ values for α-synuclein were measured as described in Example 3-5. As a result, $K_D$ of compounds of Chemical formulae 7 and 8 were measured as 68 nM and 148 nM, respectively, Both compounds effectively bind to α-synuclein (FIG. 13B). the compounds of Chemical formula 7 and Chemical formula 8 are similar in structure in that R3 and R5 have the same substituents and R2 is 1,2-dialkoxylbenzene (FIG. 13A).

To find out how the compound scaffolds and fluorophore linkers behave in the compounds of chemical formulas 7 and 8 binding to α-synuclein, it was tested that the degree of binding of the compounds of chemical formulae 4 to 6(9α-9c) with the same scaffolds as Chemical formula 7 and 8 and Fluor-linker bind to α-synuclein. As a result, the compound of chemical formula 6 which are the two same substituents as the compounds of chemical equations 7 and 8 showed affinity to α-synuclein (FIG. 13B), supporting that the binding and the selectivity of the compounds to the target protein was determined by the side chain of compounds.

In order to test whether the binding of Chemical formulae 7 and 8 to α-synuclein affect the thermal stability of α-synuclein, Circular Dichroism (CD) Thermal Denaturation Assay was performed. As a result, the compounds of Chemical formulae 7 and 8 changed the melting temperature of α-synuclein from 37° C. to 40° C., 41° C., respectively. It was known that the alpha-helix of α-synuclein has a long hydrophobic surface and amphiphilic property, the relatively hydrophobic compounds of Chemical formulae 7 and 8 interacted with the hydrophobic surface of α-synuclein.

In order to test whether the compounds of Chemical formulae 7 and 8 affect the α-synuclein aggregation, α-synuclein disease-associated mutant A53T cells were used. First, as a result of measuring $K_D$ value of the mutant (A53T), $K_D$ of the compounds of Chemical formulae 7 and 8 were 268 nM and 372 nM, respectively, confirming that both compounds bonded effectively to mutant α-synuclein (FIG. 14A). Each compound of Chemical formulae 7 and 8, and the compound of Chemical formula 4 (9a) was incubated with mutant α-synuclein and the aggregation was monitored according to Thioflavin-T aggregation. The compounds of chemical formulae 7 and 8 significantly delayed the onset of aggregation of α-synuclein and significantly reduced the amount of aggregated fibril during the 30-hour period of the experiment, while the groups treated with the compound of chemical formula 4 and DMSO used as a negative control had not inhibition of aggregation (FIG. 14B).

As a result, it was confirmed that the alpha-helix mimetic library compounds of the present invention bonded to alpha-synuclein and could inhibit the aggregation of alpha-synuclein. Therefore, the chemical library of triazine-piperazine-triazine scaffold compounds substituted with various substituents according to the present invention can be used not only for MCL-1 or α-synuclein but also can be used for inhibitors capable of controlling protein interactions mediated generally by alpha-helix.

Example 6. Preparation of the Compound Containing a Phenyl-Piperazine-Triazine as a Core Structure To synthesize the phenyl-piperazine-triazine based compound, a solid phase synthesis method was developed as shown in FIG. 15. The desired compound was obtained in an average yield of 90% or more through sequential coupling reaction to the beads modified with amine (NH2).

By referring to FIG. 15, as a first step, 4-fluoro-3-nitrobenzoic acid is loaded and bound to Rink-Amide MBHA resin, the compound ("2") bound to resin was obtained. In the second step, the compound ("4") was prepared by coupling a piperazine derivative ("3") protected with N-nosyl (Ns) to a compound ("2"). In a third step, the N-Ns protecting group is removed from the coupled compound ("4") by treatment with 2-mercaptoethanol, followed by the addition of 2-ethyl amino-4,6-dichloro-[1,3,5] triazine ("5") was introduced to produce compound ("6"). In a fourth step, compound ("7") was prepared by replacing the various amine groups ($R_3NH_2$) in the chloride position of the compound ("6"). In the fifth step, compound ("8") was prepared by reacting $SnCl_2$ in DMF to reduce the nitro group of the compound. The resulting amine was alkylated by reductive amination reaction using various aldehydes to introduce the $R_1$ functional group. The reaction with aromatic aldehydes yields the desired alkylated product in high yields, but the reaction with aliphatic aldehyde under the same conditions produces the dialkylated product as the major product. To prevent the formation of by-products by over-alkylation, benzotriazole was added to the reaction mixture. Benzotriazole is known to inhibit the formation of dialkylated by-products in reductive-amination. As a final step, a cleavage reaction was carried out with 95% TFA to produce a phenyl-piperazine-triazine derivative functionalized with three substituents.

The preparing process will be described in more detail as follows.

Rink amide MBHA resin (100 mg, 93 μmol) was treated with DMF (2 mL) for 1 hour and treated with 20% piperidine in DMF (2×10 min) to remove the Fmoc group. Unless otherwise noted, the resin was thoroughly washed with DMF (3×), MeOH (2×), $CH_2Cl_2$ (2×) and DMF (3×) at the end of each reaction step. Resin was added to a solution of 4-fluoro-3-nitrobenzoic acid (70 mg, 378 μmol), HATU (142 mg, 378 μmol) and DIEA (130 μL, 756 μmol) in DMF (1.5 mL) and the mixture were reacted at room temperature for 12 hours. To introduce the Nosyl-protected piperazin (4 equiv) into the resin, it was reacted with DIEA (10 equiv) in DMEA at 95° C. for 12 hours to obtain a resin-bound piperazine derivative "4."

The product was treated with 2-mercaptoethanol (20 equiv) and DBU (10 equiv) in DMF and reacted at room temperature to remove the nosyl group of derivative "4". Then, in order to couple 2-ethylamino-4,6-dichloro-[1,3,5] triazine (10 equiv) to the resin, DIEA (5 equiv) in THF was reacted at 60° C. for 3 hours to produce the compound "6." In order to replace chloride of compound "6" with various amine groups ($R_3NH_2$, 5 equiv), the product was reacted at 80° C. overnight in the presence of DIEA (10 equiv) in NMP to obtain compound "7." $SnCl_2 \cdot 2H_2O$ (60 equiv) solution in DMF was added to the resin and the mixture was agitated at room temperature for 24 hours. The amine ("8") bound to resin was treated with 0.4M of aldehyde solution (10 equiv) in mixed solution ($CH(OMe)_3$:DMF=9:1) and 20% (v/v) of acetic acid in methanol and then was reacted at 50° C. for 18 hours. Then, 5M of $NaCNBH_3$ (50 equiv) in TMF was added and the mixture was agitated at 50° C. for 6 hours to produce the alkylated product. When using an aliphatic aldehyde, benzotriazole (100 equiv) was added to prevent the formation of dialkylated by-product. Finally, the cleavage was performed with TFA to produce phenyl-piperazine-triazine derivatives functionalized with three substituents.

The purity and identification of the compounds prepared by the solid phase synthesis method was analyzed with LC-MS. As a result, the average purity of final product was 90% or higher, confirming the efficiency of the solid phase synthesis method. The compounds were purified with the reverse phase HPLC and identified with $^1$H-NMR, $^{13}$C-NMR and HRMS (high-resolution mass spectrometer).

36 kinds of prepared alpha-helix mimetic are shown in Table 6.

TABLE 6

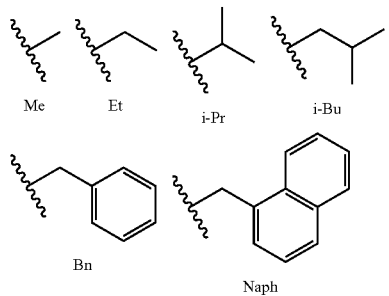

| compound | $R_6''$ | $R_3$ | $R_2''$ | purity |
|---|---|---|---|---|
| ppt-01 | Et | i-Bu | i-Pr | i-Pr |
| ppt-02 | Et | i-Bu | i-Bu | i-Bu |
| ppt-03 | Et | i-Bu | Bn | Bn |
| ppt-04 | Et | i-Bu | Naph | Naph |
| ppt-05 | Et | Bn | i-Pr | i-Pr |
| ppt-06 | Et | Bn | i-Bu | i-Bu |
| ppt-07 | Et | Bn | Bn | Bn |
| ppt-08 | Et | Bn | Naph | Naph |
| ppt-09 | Et | Me | i-Pr | i-Pr |
| ppt-10 | Et | Me | i-Bu | i-Bu |
| ppt-11 | Et | Me | Bn | Bn |
| ppt-12 | Et | Me | Naph | Naph |
| ppt-13 | i-Bu | i-Bu | i-Pr | i-Pr |
| ppt-14 | i-Bu | i-Bu | i-Bu | i-Bu |
| ppt-15 | i-Bu | i-Bu | Bn | Bn |
| ppt-16 | i-Bu | i-Bu | Naph | Naph |
| ppt-17 | i-Bu | Bn | i-Pr | i-Pr |
| ppt-18 | i-Bu | Bn | i-Bu | i-Bu |
| ppt-19 | i-Bu | Bn | Bn | Bn |
| ppt-20 | i-Bu | Bn | Naph | Naph |
| ppt-21 | i-Bu | Me | i-Pr | i-Pr |
| ppt-22 | i-Bu | Me | i-Bu | i-Bu |
| ppt-23 | i-Bu | Me | Bn | Bn |
| ppt-24 | i-Bu | Me | Naph | Naph |
| ppt-25 | Bn | i-Bu | i-Pr | i-Pr |
| ppt-26 | Bn | i-Bu | i-Bu | i-Bu |
| ppt-27 | Bn | i-Bu | Bn | Bn |
| ppt-28 | Bn | i-Bu | Naph | Naph |
| ppt-29 | Bn | Bn | i-Pr | i-Pr |
| ppt-30 | Bn | Bn | i-Bu | i-Bu |
| ppt-31 | Bn | Bn | Bn | Bn |
| ppt-32 | Bn | Bn | Naph | Naph |
| ppt-33 | Bn | Me | i-Pr | i-Pr |
| ppt-34 | Bn | Me | i-Bu | i-Bu |
| ppt-35 | Bn | Me | Bn | Bn |
| ppt-36 | Bn | Me | Naph | Naph |

Example 7. Selection and Activity Test of Alpha-Helix Mimetic Compound Inhibiting an Interaction Between BH3 Protein and MCL-1 Protein

7-1. Protein Purification

The expression vector encoding BH3-binding domain (172-320th amino acids) in Human Mcl-1$_{172-320}$ (172-320th amino acids) or human Bcl-xL$_{1-212}$ (1-212$^{th}$ amino acid) was tagged with GST, and introduced into BL21(DE3) E. coli cell. The cell was treated with 1 mM IPTG (isopropyl β-D-1-thiogalactopyranoside) to induce the protein expression. The cell pellet was resuspended with lysis buffer (20 mM Tris, pH 7.2, 250 mM NaCl, complete protease tablet (Roche)) and sonicated to be lysis. After centrifuging, the cell lysate was applied to a 5-mL GSTrap HP column (GE Life Sciences) and performed according to the manufacturer's instructions. Mcl-1$_{172-320}$ and Bcl-xL$_{1-212}$ protein were obtained by cleavage with thrombin protease, reloaded on the GSTrap HP column and performed by size exclusion chromatography to remove GST

7-2. Fluorescence Polarization Assay

In order to perform the competitive fluorescence polarization assay, MCL-1$_{172-320}$ was replaced with fluorescence-labeled BAK-BH3 peptide (FITC-BAK-BH3 peptide). Specifically, 10 nm of TAMRA-labeled Bak-BH3 (TAMRA-Abu-KALETLRRVGDGVQRNHETAF-NH$_2$) peptide was incubated for 30 minutes at dark with 0.8 μM of Mcl-1$_{172-320}$ at a final volume of 60 μL binding buffer (50 mM Tris, 100 mM NaCl, 20 nM of bovine serum albumin, pH 8.0) in black Costar 384-well plate. Various concentrations of phenyl-piperazine-triazine in 40 μL of buffer were added to the mixture. After incubating for 15 minutes, the Fluorescence polarization (mP units) was measured with Infinite®200 PRO Microplate Reader (Tecan). Excitation wavelength was 485 nm and emission was measured at 535 nm. Ki value was calculated according to the conventional method (Wang, G. P. et al., Abstr Pap Am Chem S 2004, 228, U926-U926).

7-3. Experimental Result

According to solid phase synthesis method in Example 6, a chemical library of phenyl-piperazine-triazine compound was constructed. In order to mimic three hydrophobic residues (Leu, Val, and Val) of BH3 helix peptide, the compounds introduced with various hydrophobic side chains at $R_2$, $R_3$ and $R_6$ position were synthesized. Among 36 species of library compounds, the compounds were selected to have inhibitory activity on the known interaction between Mcl-1$_{172-320}$ (deletion construct containing BH3-binding groove) and fluorescence-labeled BH3 peptides at two different concentrations of the compound (10 μM and 50 μM).

As shown in FIG. 16, PPT-31 had highest inhibitory effect on the Mcl-1/BH3 interaction at both concentrations of 10 μM and 50 μM. As shown in FIG. 17, PPT-31 includes phenyl group at each $R_2$, $R_3$ and $R_6$ (FIG. 17A), which are expected to be located at essential residues of Val$_{220}$, Val$_{216}$ and Leu$_{213}$ in BH3 alpha-helix being capable of binding to hydrophobic cleft of MCL-1 (FIG. 17B). The binding affinity of PPT-31 was determined by using the same competitive FP analysis ($K_i$=7.3 μM)(FIG. 17C).

Because BH3-binding pocket of MCL-1 is similar to BH3-binding pocket of Bcl-2 family proteins such as Bcl-xL, the present inventors tested the selectivity of PPT-31. As a result of testing the binding affinity of PPT-31 to Bcl-xL, PPT-31 did not inhibit the interaction between Bcl-xL$_{1-212}$ of BH3 (the deletion construct containing BH3-binding pocket) and BH3 (FIG. 17C). This result represents that PPT-31 is a selective inhibitor of MCL-1.

Preparation Example I. Synthesis of Compound Containing Triazine-Piperazine-Triazine Scaffold As shown in FIG. 3, Rink amide MBHA resin (100 mg, 93 μmol) was treated with DMF (2 mL) in a 5 mL fritted syringe for 1 hour. The Fmoc group was removed by treatment with 20% piperidine in DMF (2×10 min). The product was completely washed with DMF (3×), MeOH (2×), CH$_2$Cl$_2$ (2×) and DMF (3×) and monosubstituted dicholotriazine ("3") (5 equiv) in DMF (1 mL) was incubated with DIEA (5 equiv) at room temperature overnight to load monosubstituted dicholotriazine onto resin. In order to coupling piperazine derivative protected by 2-nitrobenzene sulfonyl(Ns) ("5")(10 equiv) with triazine derivative ("4") bound to resin, the product was reacted in the presence of Et$_3$N (5 equiv) in DMF at 60° C. overnight. Unless otherwise noted, the resin was thoroughly washed with DMF (3×), MeOH (2×), CH$_2$Cl$_2$ (2×) and DMF (3×) at the end of each reaction step. To remove N-Ns protecting group from the coupled compound ("6"), the product was reacted with 2-mercaptoethanol (20 equiv) and DBU (10 equiv) in DMF (10 equiv) at room temperature for 2 hours. Then, to introduce 2-ethylamino-4,6-dichloro-[1,3,5]triazine ("7") for preparing compound "8", compound (e) (5 equiv) and DIEA (5 equiv) were added to the bead in NMP at 60° C. overnight. The chloride position of prepared compound ("8") was replaced with various amine groups (R$_2$"R$_2$"NH). Finally, the cleavage reaction was performed with addition of TFA (trifluoroacetic acid), to obtain triazine-piperazine-triazine compound "9" functionalized with three functional groups.

The purity and identify of the compound prepared by the solid phase synthesis method were confirmed with LC-MS. The average purity of final product was 92% or higher, suggesting the efficiency of solid phase synthesis method. Then, the compound was purified with reverse-phase HPLC and identified with $^1$H-NMR, $^{13}$C-NMR and HRMS (high-resolution mass spectrometer).

Preparation Example 1. Preparation for Compound of Chemical Formula 4

6-(4-(4-amino-6-((benzo[d][1,3]dioxol-5-ylmethyl) amino)-1,3,5-triazin-2-yl)-2-benzylpiperazin-1-yl)-N$^2$-benzyl-N$^4$-ethyl-1,3,5-triazine-2,4-diamine TFA Yield: 25.8 mg (43%) from 100 mg of resin. $^1$H-NMR (500 MHz, methanol-d$_4$) δ 1.26 (m, 3H) 2.61-2.77 (m, 2H), 3.05-3.15 (m, 2H), 3.31-3.35 (m, 3H), 4.31 (m, 1H), 4.45-4.65 (m, 6H), 5.04 (m, 1H), 5.71 (d, J=36.0 Hz, 1H), 5.83 (d, J=3.5 Hz, 1H), 6.65-6.81 (m, 3H), 6.98-7.08 (m, 5H), 7.19 (m, 1H), 7.25-7.27 (m, 4H); $^{13}$C-NMR (126 MHz, CDCl$_3$) δ 14.4, 35.9, 39.1, 43.4, 44.3, 44.5, 44.7, 53.2, 53.5, 55.3, 101.2, 107.9, 108.4, 120.8, 121.1, 127.0, 127.5, 127.7, 128.5, 128.8, 129.2, 130.7, 136.9, 137.2, 147.2, 147.9, 155.7, 156.2, 157.5, 162.6; HRMS (ESI) calculated for C$_{34}$H$_{39}$N$_{12}$O$_2$[M+H]$^+$: 647.3319; Found: 647.3319.

Preparation Example 2. Preparation for Compound of Chemical Formula 5

6-(4-(4-amino-6-((cyclopropylmethyl)(propyl) amino)-1,3,5-triazin-2-yl)-2-benzylpiperazin-1-yl)-N$^2$-(benzo[d][1,3]dioxol-5-ylmethyl)-N$^4$-ethyl-1,3,5-triazine-2,4-diamine.TFA Yield: 18.8 mg (31%) from 100 mg of resin. $^1$H-NMR (500 MHz, methanol-d$_4$) δ 0.40 (m, 2H), 0.62 (m, 2H), 1.00 (m, 3H), 1.12 (br s, 1H), 1.25 (t, J=7.5 Hz, 3H), 1.72 (m, 2H), 2.91-3.00 (m, 2H), 3.33 (m, 2H), 3.49-3.56 (m, 7H), 4.46-4.61 (m, 4H), 4.73 (m, 1H), 5.19 (m, 1H), 5.91 (s, 1H), 5.94 (s, 1H). 6.76-6.88 (m, 3H), 7.13 (d, J=6.5 Hz, 1H), 7.20-7.25 (m, 4H); $^{13}$C-NMR (126 MHz, CDCl$_3$) δ 3.7, 9.3, 9.6, 10.7, 11.5, 14.4, 20.9, 35.9, 39.1, 43.4, 44.3, 49.4, 50.1, 51.8, 52.9, 55.4, 101.2, 107.6, 108.3, 120.4, 121.1, 127.1, 128.6, 129.2, 130.0, 130.8, 131.0, 136.9, 147.2, 148.1, 155.6, 156.0, 158.2, 162.6; HRMS (ESI) calculated for C$_{34}$H$_{45}$N$_{12}$O$_2$[M+H]+: 653.3788; Found: 653.3787.

Preparation Example 3. Preparation for Compound Shown in Chemical Formula 6

4-(2-((4-(4-(4-amino-6-((4-phenoxyphenyl)amino)-1,3,5-triazin-2-yl)-2-benzylpiperazin-1-yl)-6-(ethylamino)-1,3,5-triazin-2-yl)amino)ethyl)phenol.TFA Yield: 27.0 mg (41%) from 100 mg of resin. $^1$H-NMR (500 MHz, methanol-d$_4$) δ 1.25 (m, 3H), 2.82 (m, 2H), 2.91 (br s, 2H), 3.30 (m, 2H), 3.49 (m, 3H), 3.66 (m, 2H), 4.57-4.68 (m, 3H), 5.13 (m, 1H), 6.73 (m, 2H), 6.90 (br s, 1H), 7.03-7.07 (m, 6H), 7.17-7.24 (m, 5H) 7.41 (m, 3H), 7.58 (br s, 1H); $^{13}$C-NMR (126 MHz, DMSO-d$_6$) δ 14.6, 14.8, 34.2, 35.7, 36.0, 42.5, 43.2, 44.1, 53.9, 115.6, 118.7, 119.5, 122.9, 123.7, 126.7, 128.7, 129.2, 129.6, 130.0, 130.1, 130.5, 138.2, 152.5, 155.1, 155.4, 156.3, 157.6, 162.1, 163.8; HRMS (ESI) calculated for C$_{39}$H$_{43}$N$_{12}$O$_2$ [M+H]$^+$: 711.3632; Found: 711.3613.

Preparation Example 4. Preparation for Compound of Chemical Formula 7

6-(4-(4-amino-6-(4-phenoxyphenylamino)-1,3,5-triazin-2-yl)-2-benzylpiperazin-1-yl)-N$^2$-(benzo[d][1,3]dioxol-5-ylmethyl)-N$^4$-ethyl-1,3,5-triazine-2,4-diamine.TFA $^1$H-NMR (600 MHz, CDCl$_3$) δ 1.28 (m, 3H) 2.80-2.86 (m, 2H), 3.14-3.22 (m, 2H), 3.36-3.43 (m, 1H), 3.48-3.53 (m, 2H), 4.50-4.56 (m, 2H), 4.63-4.77 (m, 3H), 5.12 (bs, 1H), 5.93-5.98 (m, 2H), 6.76-6.89 (m, 4H), 7.01-7.20 (m, 7H), 7.26-7.29 (m, 1H), 7.38-7.41 (m, 3H), 7.58 (dd, J=3.0, 9.0 Hz, 1H), 7.76-7.82 (m, 1H), 8.05-8.16 (m, 1H), 10.58 (m, 1H), 14.59 (bs, 1H); $^{13}$C-NMR (150 MHz, CDCl$_3$) δ 14.3, 35.9, 36.2, 39.1, 39.2, 43.6, 44.2, 44.5, 53.4, 101.2, 107.6, 108.4, 118.9, 120.4, 121.0, 123.2, 123.7, 127.1, 128.6, 129.0, 129.3, 129.8, 131.3, 136.7, 147.2, 148.1, 154.2, 154.7, 155.8, 156.2, 157.0, 157.6, 162.5; HRMS (ESI) calculated for C$_{39}$H$_{41}$N$_{12}$O$_3$[M+H]$^+$: 725.3425; Found: 725.3427.

Preparation Example 5. Preparation for Compound of Chemical Formula 8

6-(4-(4-amino-6-(4-phenoxyphenylamino)-1,3,5-triazin-2-yl)-2-benzylpiperazin-1-yl)-N$^2$-(3,4-dimethoxybenzyl)-N$^4$-ethyl-1,3,5-triazine-2,4-diamine.TFA (Q2)

$^1$H-NMR (600 MHz, CDCl$_3$) δ 1.28 (m, 3H) 2.81-2.86 (m, 2H), 3.16-3.22 (m, 2H), 3.36-3.43 (m, 1H), 3.47-3.51 (m, 2H), 3.80-3.91 (m, 5H), 4.55-4.59 (m, 2H), 4.65-4.69 (m, 2H), 4.74-4.76 (m, 1H), 5.12 (bs, 1H), 6.81-6.89 (m, 4H), 7.00-7.21 (m, 7H), 7.26-7.29 (m, 1H), 7.38-7.41 (m, 3H), 7.58 (dd, J=3.0, 9.0 Hz, 1H), 7.69-7.77 (m, 1H), 8.23-8.30 (m, 1H), 10.58 (m, 1H), 14.31 (bs, 1H); $^{13}$C-NMR (150 MHz, CDCl$_3$) δ 14.3, 35.9, 36.3, 39.2, 43.6, 44.3, 44.5, 53.4, 55.9, 110.6, 110.1, 111.3, 118.9, 119.1, 119.4, 119.9, 123.2, 123.6, 127.1, 128.6, 129.0, 129.3, 129.9, 131.3, 136.7, 148.7, 149.3, 154.2, 154.7, 155.7, 156.0, 157.0, 157.5, 162.5; HRMS (ESI) calculated for C$_{40}$H$_{40}$N$_{12}$O$_3$[M+H]$^+$: 741.3748; Found: 741.3741.

Preparation Example 6. Preparation for Compound 9-Nc 6-(4-(4-amino-6-(ethylamino)-1,3,5-triazin-2-yl)piperazin-1-yl)-$N^2,N^4$-diethyl-1,3,5-triazine-2,4-diamine.TFA Yield: 18.0 mg (50%) from 100 mg of resin. $^1$H-NMR (500 MHz, methanol-$d_4$) δ 1.14 (t, J=7.0 Hz, 9H), 3.38 (m, 6H), 3.89 (br s, 8H); $^{13}$C-NMR (126 MHz, DMSO-$d_6$) δ 14.6, 35.7, 43.4, 155.8, 157.4, 162.1; HRMS (ESI) calculated for $C_{16}H_{29}N_{12}$ [M+H]$^+$: 389.2638; Found: 389.2631.

Preparation Example II. Synthesis of Phenyl-Piperazine-Triazine Scaffold Compound As shown in FIG. 15, Rink amide MBHA resin (100 mg, 93 μmol) was treated with DMF (2 mL) for 1 hour and treated with 20% piperidine in DMF (2×10 min) to remove the Fmoc group. Unless otherwise noted, the resin was thoroughly washed with DMF (3×), MeOH (2×), $CH_2Cl_2$ (2×) and DMF (3×) at the end of each reaction step.

The resin was added to 4-fluoro-3-nitrobenzoic acid (70 mg, 378 μmol), HATU (142 mg, 378 μmol) and DIEA (130 μL, 756 μmol) in DMF (1.5 mL) and the mixture was incubated at room temperature for 12 hours. To introduce Nosyl-protected piperazin)(4 equiv) onto the resin, the product was reacted with DIEA (10 equiv) in DMF at 95° C. for 12 hours to produce resin-bound piperazine derivative "4". To remove nosyl group from the derivative "4", the product was reacted with 2-mercaptoethanol (20 equiv) and DBU (10 equiv) in DMF at room temperature. To coupling 2-ethylamino-4,6-dichloro-[1,3,5]triazine (10 equiv) onto the resin, the product was reacted with DIEA (5 equiv) in THF at 60° C. for 3 hours, to obtain compound "6". To replace chloride position of compound "6" with various amine groups ($R_3NH_2$, 5 equiv), the compound was reacted with DIEA (10 equiv) in NMP at 80° C. overnight, to produce compound "7". $SnCl_2.2H_2O$ (60 equiv) in DMF was added to the resin and the mixture was agitated at room temperature for 24 hours. The amine ("8") bound to resin was treated with 0.4M of aldehyde solution (10 equiv) in mixed solution (CH(OMe)$_3$:DMF=9:1) and 20% (v/v) of acetic acid in methanol and then was reacted at 50° C. for 18 hours. Then, 5M of NaCNBH$_3$ (50 equiv) in TMF was added and the mixture was agitated at 50° C. for 6 hours to produce the alkylated product. When using an aliphatic aldehyde, benzotriazole (100 equiv) was added to prevent the formation of dialkylated by-product. Finally, the cleavage was performed with TFA to produce phenyl-piperazine-triazine derivatives functionalized with three substituents.

The purity and identification of the compounds prepared by the solid phase synthesis method was analyzed with LC-MS. As a result, the average purity of final product was 90% or higher, confirming the efficiency of the solid phase synthesis method. The compounds were purified with the reverse phase HPLC and identified with $^1$H-NMR, $^{13}$C-NMR and HRMS (high-resolution mass spectrometer).

Preparation Example 7. Preparation for PPT-3 Compound

2-{4-(2-aminoethyl-4-carbamoylphenyl)-2-isobutyl-piperazine}-4-aminoethyl-6-aminobenzyl-[1,3,5]triazine (PPT-3)

$^1$H NMR (300 MHz, CDCl$_3$) δ 0.92 (t, J=6.9 Hz, 3H), 0.97 (dd, J=6.3, 9.3 Hz, 3H), 1.20 (q, J=7.2 Hz, 3H), 1.33 (t, J=6.6 Hz, 3H), 1.55-1.62 (m, 1H), 1.76-1.91 (m, 2H), 2.60-2.84 (m, 2H), 3.05-3.32 (m, 5H), 3.42-3.48 (m, 2H), 4.61 (t, J=5.7 Hz, 2H), 4.84 (t, J=14.7 Hz, 1H), 4.98-5.03 (m, 1H), 6.93 (d, J=8.1 Hz, 1H), 7.07-7.13 (m, 2H), 7.24-7.37 (m, 4H), 7.60-7.62 (m, 1H), 7.97-8.00 (m, 1H); $^{13}$C NMR (75 MHz, CDCl$_3$) δ 16.1, 16.2, 16.6, 24.4, 24.5, 24.9, 26.7, 37.7, 40.4, 40.7, 41.8, 46.0, 46.1, 46.3, 52.0, 52.7, 55.9, 111.4, 117.9, 121.1, 129.0, 129.5, 129.8, 132.1, 139.2, 143.7, 145.0, 157.4, 157.9, 164.1, 173.0. HRMS (FAB) calculated for $C_{29}H_{42}N_9O$ [M+H]$^+$ 532.3512, found: 532.3509.

Preparation Example 8. Preparation for PPT-5 Compound

2-{4-(2-aminoethyl-4-carbamoylphenyl)-2-benzyl-piperazine}-4-aminoethyl-6-aminoisopropyl-[1,3,5]triazine (PPT-5)

$^1$H NMR (300 MHz, CDCl$_3$) δ 1.20-1.30 (m, 6H), 1.36 (t, J=6.9 Hz, 6H), 2.69-2.78 (m, 1H), 2.83 (dd, J=3.9, 12.0 Hz, 1H), 3.11-3.54 (m, 9H), 4.07-4.20 (m, 1H), 4.79-4.86 (m, 1H), 5.17 (brs, 1H), 6.94 (d, J=8.1 Hz, 1H), 7.05 (dd, J=1.8, 8.1 Hz, 1H), 7.16-7.43 (m, 6H); $^{13}$C NMR (75 MHz, CDCl$_3$) δ 16.1, 16.3, 16.8, 24.0, 24.2, 37.6, 40.2, 42.2, 45.1, 53.1, 54.6, 55.2, 111.4, 117.7, 121.2, 130.4, 130.9, 131.0, 131.6, 139.7, 143.5, 145.1, 156.6, 157.3, 164.3, 164.6, 172.7. HRMS (FAB) calculated for $C_{28}H_{39}N_9O$ [M+H]$^+$ 518.3356, found: 518.3355.

Preparation Example 9. Preparation for PPT-15 Compound

2-{4-(2-aminoisobutyl-4-carbamoylphenyl)-2-isobutyl-piperazine}-4-aminoethyl-6-aminobenzyl-[1,3,5]triazine (PPT-15)

$^1$H NMR (300 MHz, CDCl$_3$) δ 0.89 (dd, J=3, 6.6 Hz, 3H), 0.98 (t, J=6.9 Hz, 3H), 1.03 (dd, J=3, 6.6 Hz, 6H), 1.20-1.26 (m, 3H), 1.50-1.57 (m, 1H), 1.67-1.74 (m, 1H), 1.92-2.04 (m, 2H), 2.67-2.83 (m, 2H), 2.98-3.12 (m, 4H), 3.31-3.49 (m, 3H), 4.58-4.62 (m, 2H), 4.78 (t, J=15.0 Hz, 1H), 5.02-5.05 (m, 1H), 6.93 (d, J=8.1 Hz, 2H), 7.06-7.11 (m, 2H), 7.28-7.33 (m, 2H), 7.60-7.63 (m, 1H), 8.01-8.03 (m, 1H); $^{13}$C NMR (75 MHz, CDCl$_3$) δ 12.3, 12.4, 18.7, 20.8, 21.0, 22.8, 26.2, 33.9, 37.0, 38.0, 42.4, 42.6, 48.1, 48.2, 49.2, 49.8, 52.2, 107.6, 113.9, 117.4, 125.3, 125.7, 126.8, 127.1, 135.2, 135.4, 140.1, 141.5, 153.5, 153.8, 160.1, 169.8. HRMS (FAB) calculated for $C_{31}H_{46}N_9O$ [M+H]$^+$ 560.3825, found: 560.3827.

Preparation Example 10. Preparation for PPT-19 Compound

2-{4-(2-aminoisobutyl-4-carbamoylphenyl)-2-benzyl-piperazine}-4-aminoethyl-6-aminobenzyl-[1,3,5]triazine (PPT-19)

$^1$H NMR (300 MHz, CDCl$_3$) δ 1.06-1.08 (m, 6H), 1.20-1.26 (m, 3H), 1.96-2.05 (m, 1H), 2.57-2.68 (m, 2H), 2.84-2.94 (m, 1H), 3.06-3.23 (m, 5H), 3.35-3.49 (m, 3H), 4.50-4.65 (m, 2H), 4.78 (t, J=15.0 Hz, 1H), 5.10-5.16 (m, 1H), 6.90 (dd, J=1.8, 8.1 Hz, 2H), 6.98-7.04 (m, 2H), 7.11-7.34 (m, 7H), 7.57-7.65 (m, 1H), 7.96-8.03 (m, 1H); $^{13}$C NMR (75 MHz, CDCl$_3$) δ 13.9, 14.0, 20.2, 27.8, 35.4, 35.6, 40.1, 44.0, 51.1, 51.9, 109.0, 115.0, 118.8, 126.4, 127.1, 128.2, 128.3, 128.7, 129.8, 137.3, 140.8, 143.1, 155.6, 162.1, 169.9. HRMS (FAB) calculated for $C_{34}H_{43}N_9O$ [M+H]$^+$ 594.3669, found: 594.3665.

Preparation Example 11. Preparation for PPT-23 Compound

2-{4-(2-aminoisobutyl-4-carbamoylphenyl)-2-methyl-piperazine}-4-aminoethyl-6-aminobenzyl-[1,3,5]triazine (PPT-23)

$^1$H NMR (300 MHz, CDCl$_3$) δ 1.05 (q, J=3.3 Hz, 6H), 1.26 (t, J=7.2 Hz, 3H), 1.38 (dd, J=6.9, 25.5 Hz, 3H), 1.95-2.07 (m, 1H), 2.74-2.85 (m, 2H), 2.97-3.18 (m, 4H), 3.32-3.50 (m, 3H), 4.52-4.63 (m, 3H), 4.88-5.02 (m, 1H), 6.95 (d, J=8.1 Hz, 1H), 6.98-7.09 (m, 2H), 7.28 (d, J=2.7 Hz, 3H), 7.67-7.74 (m, 1H), 8.12-8.21 (m, 1H); $^{13}$C NMR (75 MHz, CDCl$_3$) δ 16.1, 17.3, 22.5, 30.1, 37.7, 41.6, 46.4, 49.4, 52.8, 53.5, 57.3, 111.2, 117.3, 120.8, 129.4, 130.5, 131.8, 143.3, 145.2, 172.1. HRMS (FAB) calculated for C$_{28}$H$_{40}$N$_9$O [M+H]$^+$ 518.3356, found: 518.3353.

Preparation Example 12. Preparation for PPT-28 Compound

2-{4-(2-aminobenzyl-4-carbamoylphenyl)-2-isobutyl-piperazine}-4-aminoethyl-6-amino-2-naphthylmethyl-[1,3,5]triazine (PPT-28)

$^1$H NMR (300 MHz, CDCl$_3$) δ 0.61 (dd, J=6.0, 14.7 Hz, 3H), 0.78 (dd, J=6.0, 14.7 Hz, 3H), 1.18-1.26 (m, 3H), 1.30-1.44 (m, 2H), 1.72-1.81 (m, 1H), 2.60-2.86 (m, 2H), 3.01-3.49 (m, 5H), 4.27-4.43 (m, 2H), 4.68-5.07 (m, 4H), 6.93 (dd, J=4.2, 7.8 Hz, 1H), 7.10-7.14 (m, 2H), 7.31-8.04 (m, 12H); $^{13}$C NMR (75 MHz, CDCl$_3$) δ 13.8, 22.1, 24.3, 35.5, 38.2, 38.3, 39.5, 41.3, 48.1, 49.7, 49.8, 50.5, 53.6, 53.9, 109.2, 116.1, 117.2, 118.9, 122.4, 122.6, 124.9, 125.6, 126.1, 127.4, 128.1, 128.5, 128.7, 130.6, 130.8, 131.8, 132.1, 133.5, 138.2, 141.7, 142.6, 155.1, 155.3, 155.5, 161.6, 161.7, 162.1, 171.0. HRMS (FAB) calculated for C$_{38}$H$_{46}$N$_9$O [M+H]$^+$ 644.3825, found: 644.3827.

Preparation Example 13. Preparation for PPT-31 Compound

2-{4-(2-aminobenzyl-4-carbamoylphenyl)-2-benzyl-piperazine}-4-aminoethyl-6-aminobenzyl-[1,3,5]triazine (PPT-31)

$^1$H NMR (300 MHz, CDCl$_3$) δ 1.18-1.25 (m, 3H), 2.63-3.14 (m, 6H), 3.22-3.31 (m, 1H), 3.36-3.45 (m, 2H), 4.45 (d, J=2.7 Hz, 2H), 4.53-4.64 (m, 2H), 4.76 (t, J=13.8 Hz, 1H), 5.06-5.12 (m, 1H), 6.91-7.37 (m, 16H), 7.57-7.68 (m, 1H), 7.96-8.03 (m, 1H); $^{13}$C NMR (75 MHz, CDCl$_3$) δ 14.4, 35.8, 40.4, 44.1, 44.2, 44.4, 48.1, 51.2, 51.3, 52.3, 52.4, 53.2, 53.3, 109.7, 116.3, 119.4, 126.7, 127.3, 127.6, 128.6, 128.9, 129.0, 130.0, 137.6, 138.9, 141.5, 143.0, 155.5, 156.0, 162.4, 170.4. HRMS (FAB) calculated for C$_{37}$H$_{42}$N$_9$O [M+H]$^+$ 628.3512, found: 628.3510.

Preparation Example 14. Preparation for PPT-36 Compound

2-{4-(2-aminobenzyl-4-carbamoylphenyl)-2-methyl-piperazine}-4-aminoethyl-6-amino-2-naphthylmethyl-[1,3,5]triazine (PPT-36)

$^1$H NMR (300 MHz, CDCl$_3$) δ 1.08-1.24 (m, 6H), 2.65-2.84 (m, 2H), 3.03-3.29 (m, 3H), 3.40 (quin, J=6.8 Hz, 2H), 4.28 (q, J=13.5 Hz, 2H), 4.65 (t, J=13.5 Hz, 1H), 4.87-5.10 (m, 3H), 6.93 (d, J=8.7 Hz, 1H), 7.09-7.12 (m, 2H), 7.30-7.52 (m, 8H), 7.76-7.87 (m, 1H), 8.01-8.17 (m, 1H); $^{13}$C NMR (75 MHz, CDCl$_3$) δ 16.0, 17.1, 37.8, 44.1, 49.4, 50.3, 52.6, 57.1, 111.4, 118.5, 120.9, 124.8, 127.2, 127.8, 128.0, 128.3, 129.5, 129.6, 130.4, 130.7, 130.8, 133.0, 134.4, 135.7, 140.4, 140.8, 144.1, 144.6, 157.6, 163.5, 163.6, 164.0, 173.5. HRMS (FAB) calculated for C$_{35}$H$_{40}$N$_9$O [M+H]$^+$ 602.3356, found: 602.3358.

The invention claimed is:
1. A compound or a pharmaceutically acceptable salt thereof, wherein the compound is selected from the group consisting of the compounds of Chemical formula 4 to Chemical formula 8:

[Chemical formula 4]

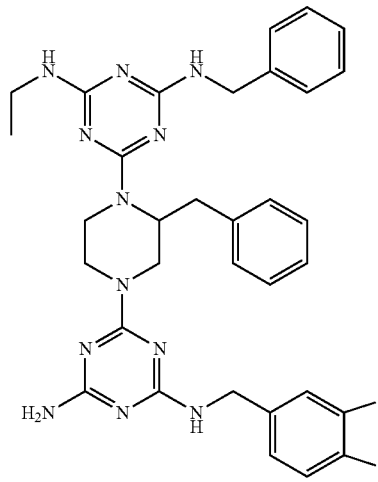

[Chemical formula 5]

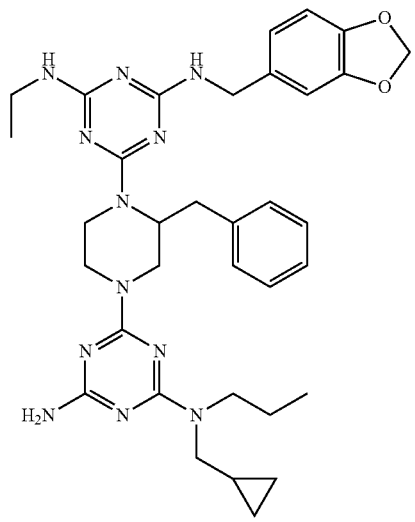

[Chemical formula 6]

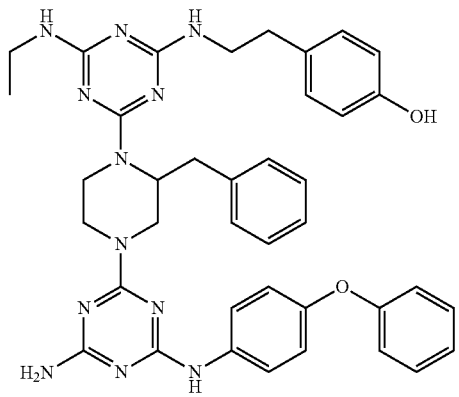

-continued

[Chemical formula 7]

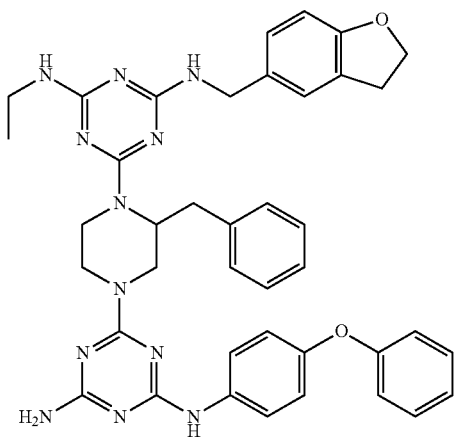

[Chemical formula 8]

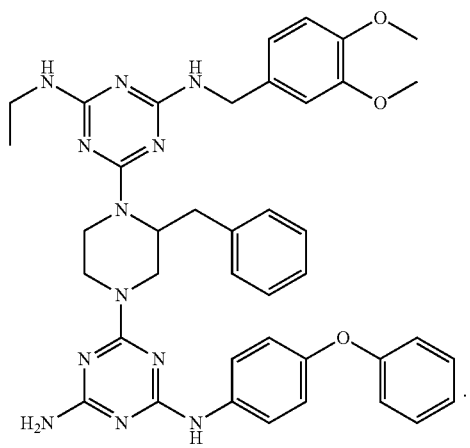

2. A compound or a pharmaceutically acceptable salt thereof,
wherein the compound is the compound of Chemical formula 9:

[Chemical formula 9]

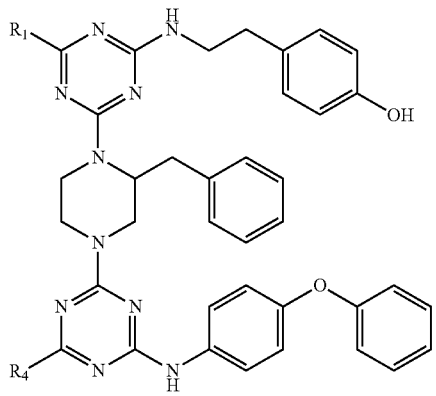

wherein, in Chemical formula 9,
$R_1$ and $R_4$ are independently —$NR_8R_9$,
$R_8$ and $R_9$ are independently hydrogen, ($C_1$-$C_6$) alkyl, —$(CH_2)_rNH_2$, —$(CH_2)_rN(H)C(=NH)NH_2$, —$(CH_2)_rC(=O)OH$, or —$(CH_2)_rOH$, and
r is an integer of 1 to 6.

3. A compound or a pharmaceutically acceptable salt thereof, wherein the compound is the compound of Chemical formula 3:

[Chemical formula 3]

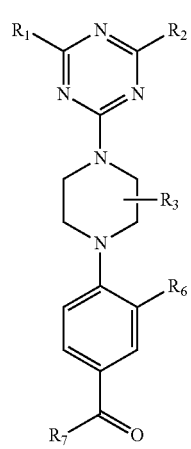

wherein $R_1$, $R_2$, $R_3$, $R_6$ and $R_7$ in Chemical formula 3 are independently selected from the groups represented by the following chemical structures:

| R1 | R2 | R3 | R6 | R7 |
|---|---|---|---|---|
| NHEt | NHiPr | iBu | NHEt | NH$_2$ |
| NHEt | NHiBu | iBu | NHEt | NH$_2$ |
| NHEt | NHBn | iBu | NHEt | NH$_2$ |
| NHEt | NHNaph | iBu | NHEt | NH$_2$ |
| NHEt | NHiPr | Bn | NHEt | NH$_2$ |
| NHEt | NHiBu | Bn | NHEt | NH$_2$ |
| NHEt | NHBn | Bn | NHEt | NH$_2$ |
| NHEt | NHNaph | Bn | NHEt | NH$_2$ |
| NHEt | NHiPr | Me | NHEt | NH$_2$ |
| NHEt | NHiBu | Me | NHEt | NH$_2$ |
| NHEt | NHBn | Me | NHEt | NH$_2$ |
| NHEt | NHNaph | Me | NHEt | NH$_2$ |
| NHEt | NHiPr | iBu | NHiBu | NH$_2$ |
| NHEt | NHiBu | iBu | NHiBu | NH$_2$ |
| NHEt | NHBn | iBu | NHiBu | NH$_2$ |
| NHEt | NHNaph | iBu | NHiBu | NH$_2$ |
| NHEt | NHiPr | Bn | NHiBu | NH$_2$ |
| NHEt | NHiBu | Bn | NHiBu | NH$_2$ |
| NHEt | NHBn | Bn | NHiBu | NH$_2$ |
| NHEt | NHNaph | Bn | NHiBu | NH$_2$ |
| NHEt | NHiPr | Me | NHiBu | NH$_2$ |
| NHEt | NHiBu | Me | NHiBu | NH$_2$ |
| NHEt | NHBn | Me | NHiBu | NH$_2$ |
| NHEt | NHNaph | Me | NHiBu | NH$_2$ |
| NHEt | NHiPr | iBu | NHBn | NH$_2$ |
| NHEt | NHiBu | iBu | NHBn | NH$_2$ |
| NHEt | NHBn | iBu | NHBn | NH$_2$ |
| NHEt | NHNaph | iBu | NHBn | NH$_2$ |
| NHEt | NHiPr | Bn | NHBn | NH$_2$ |
| NHEt | NHiBu | Bn | NHBn | NH$_2$ |
| NHEt | NHBn | Bn | NHBn | NH$_2$ |
| NHEt | NHNaph | Bn | NHBn | NH$_2$ |
| NHEt | NHiPr | Me | NHBn | NH$_2$ |
| NHEt | NHiBu | Me | NHBn | NH$_2$ |
| NHEt | NHBn | Me | NHBn | NH$_2$ |
| NHEt | NHNaph | Me | NHBn | NH$_2$ |

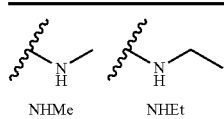

| R1 | R2 | R3 | R6 | R7 | |
|---|---|---|---|---|---|
| NHiPR, NHiBu, NHBn, NHNaph, Me, i-Bu, Bn | | | | | 5-30 |

4. The compound or a pharmaceutically acceptable salt thereof according to claim 3, wherein the compound is the compound of Chemical formula 10:

[Chemical formula 10]

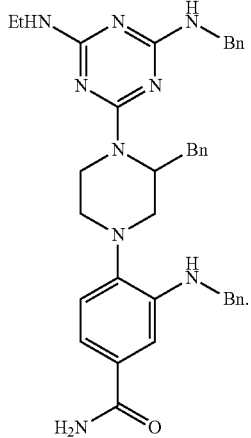

5. A composition, comprising a compound or a pharmaceutically acceptable salt thereof according to claim 1, and
pharmaceutically acceptable carriers, excipients or diluents.

6. A pharmaceutical composition, comprising:
pharmaceutically acceptable carriers, excipients or diluents; and
a compound selected from the group consisting of the compounds of Chemical formula 4 to Chemical formula 6, and Chemical formula 9 and Chemical formula 10, or a pharmaceutically acceptable salt thereof:

[Chemical formula 4]

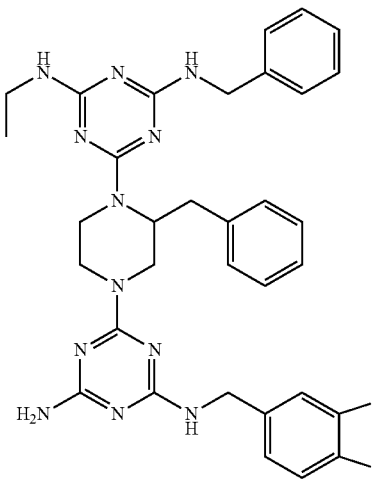

[Chemical formula 5]

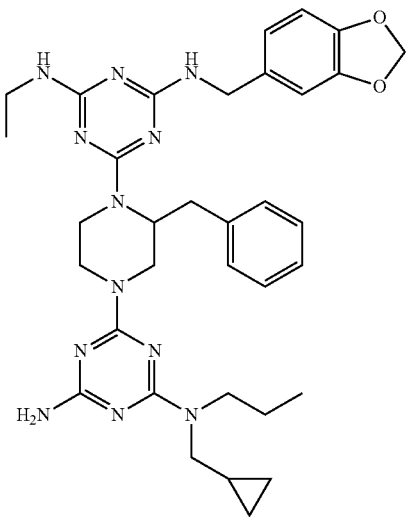

[Chemical formula 6]

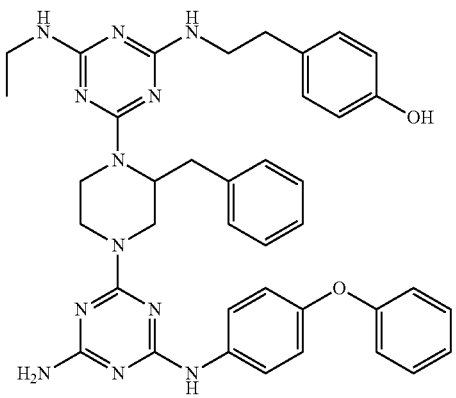

-continued

[Chemical formula 9]

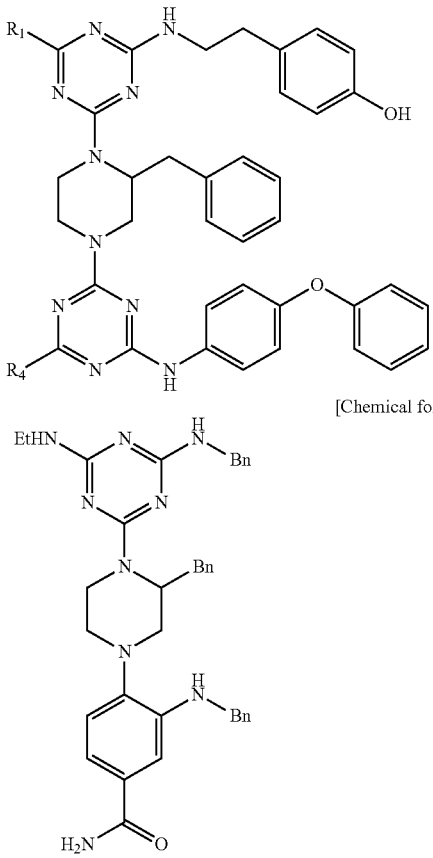

[Chemical formula 10]

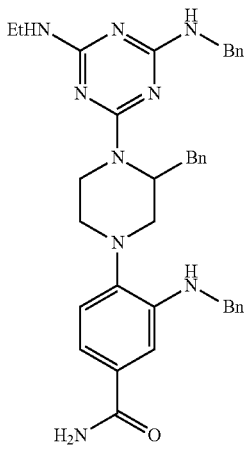

wherein in Chemical formula 9,
R$_1$ and R$_4$ are independently —NR$_8$R$_9$ where R$_8$ and R$_9$ are independently hydrogen, (C$_1$-C$_6$) alkyl, —(CH$_2$)$_r$NH$_2$, —(CH$_2$)$_r$N(H)C(=NH)NH$_2$, —(CH$_2$)$_r$C(=O)OH, or —(CH$_2$)$_r$OH, and
r is an integer of 1 to 6.

7. The pharmaceutical composition according to claim 6, wherein the compound is the compound of Chemical formula 9;

[Chemical formula 9]

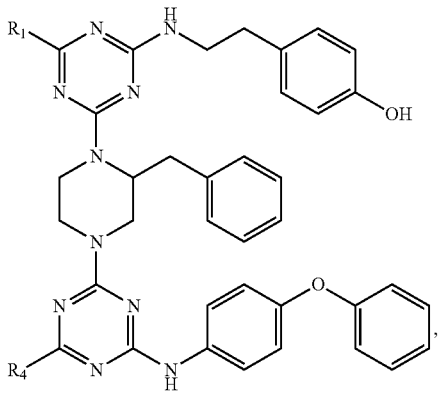

and
wherein in Chemical formula 9,
R$_1$ and R$_4$ are independently —NR$_8$R$_9$ where R$_8$ and R$_9$ are independently hydrogen, (C$_1$-C$_6$) alkyl, —(CH$_2$)$_r$NH$_2$, —(CH$_2$)$_r$N(H)C(=NH)NH$_2$, —(CH$_2$)$_r$C(=O)OH, or —(CH$_2$)$_r$OH, and
r is an integer of 1 to 6.

8. A pharmaceutical composition, comprising:
pharmaceutically acceptable carriers, excipients or diluents; and
a compound selected from the group consisting of the compounds of Chemical formula 7 to Chemical formula 8, or a pharmaceutically acceptable salt thereof:

[Chemical formula 7]

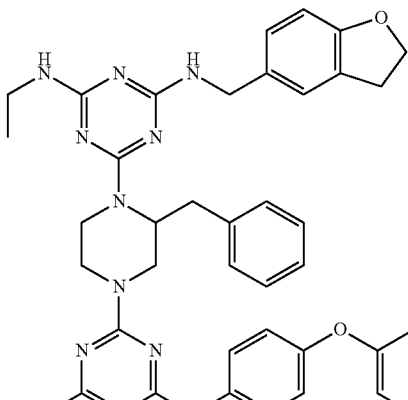

[Chemical formula 8]

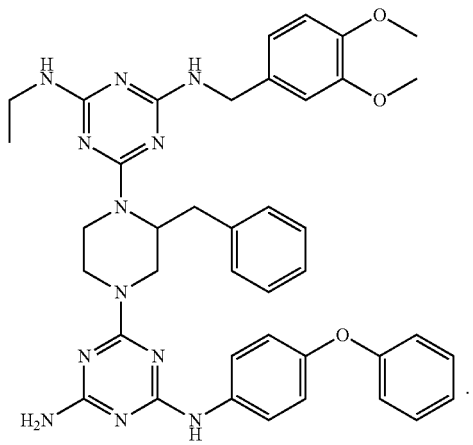

9. The pharmaceutical composition according to claim 6, wherein the compound is the compound of Chemical formula 10:

[Chemical formula 10]

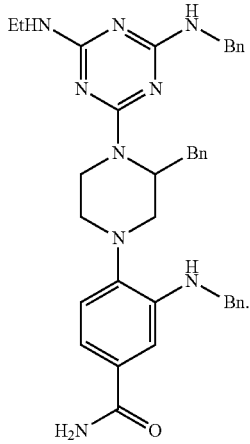

10. A composition, comprising a compound or a pharmaceutically acceptable salt thereof according to claim 2, and pharmaceutically acceptable carriers, excipients or diluents.

11. A composition, comprising a compound or a pharmaceutically acceptable salt thereof according to claim 3, and pharmaceutically acceptable carriers, excipients or diluents.

12. A composition, comprising a compound or a pharmaceutically acceptable salt thereof according to claim 4, and pharmaceutically acceptable carriers, excipients or diluents.

* * * * *